(12) United States Patent
Hodgson et al.

(10) Patent No.: US 6,573,091 B1
(45) Date of Patent: Jun. 3, 2003

(54) CHIMERIC VIRAL PACKAGING SIGNAL WITHOUT GAG GENE SEQUENCES

(75) Inventors: Clague Hodgson, Lincoln, NE (US); Mary Ann Zink, Lincoln, NE (US); Guoping Xu, Lincoln, NE (US)

(73) Assignee: Nature Technology Corporation, Lincoln, NE (US)

( * ) Notice: Subject to any disclaimer, the term of this patent is extended or adjusted under 35 U.S.C. 154(b) by 0 days.

(21) Appl. No.: 09/554,572

(22) Filed: Sep. 18, 2000

Related U.S. Application Data

(60) Provisional application No. 60/066,148, filed on Nov. 19, 1997.

(51) Int. Cl.[7] .............................................. C12N 15/00
(52) U.S. Cl. ............................... 435/320.1; 424/185.1; 424/187.1; 424/199.1; 435/69.1; 435/456; 514/44; 536/23.1; 536/23.4; 536/23.72
(58) Field of Search .......................... 424/185.1, 177.1, 424/199.1; 435/69.1, 91.2, 320.1, 456; 514/44; 536/23.1, 23.4, 23.72

(56) References Cited

U.S. PATENT DOCUMENTS 5,747,323 A   5/1998   Darlix et al.
5,925,565 A * 7/1999   Berlioz et al. ............... 435/325

FOREIGN PATENT DOCUMENTS

WO   WO 92/07950   5/1992
WO   WO 95/30763   11/1995
WO   WO 96/01324   1/1996

OTHER PUBLICATIONS

Torrent et al. Stable MLV–VL30 dicistronic retroviral vectors with a VL30 or MoMLV sequence promotion both packaging of genomic RNA and expression of the 3'cistron. Human Gene Therapy (1996) vol. 7, pp. 603–612.*

Adams et al., "Complete nucleotide sequences of a mouse VL30 retro–element," *Molecular Cell. Biol.*, 8:2989–2998 (1988).

Chakraborty et al., "Synthetic retrotransposon vectors for gene therapy—VL30 retro virus vector construction by gene amplification," *Faseb Journal*, 7:971–977 (1993).

Chakraborty, "Transmission of endogenous VL30 retrotransposons by helper cells used in gene therapy," *Cancer Gene Therapy*, 1:113–118 (1994).

Hatzoglou et al., "Efficient packaging of a specific VL30 retroelement by spi 2 cells which produe MoMLV recombinant retroviruses," *Human Gene Therapy*, 1:385–397 (1990).

Patience et al., "Packaging of endogenous retroviral sequences in retroviral vectors produced by murine and human packaging cells," *Journal of Virology*, 72:2671–2676 (1998).

* cited by examiner

*Primary Examiner*—James Housel
*Assistant Examiner*—Ulrike Winkler

(57) ABSTRACT

A chimeric viral packaging signal is described for the transmission of genetic materials via retrovirus. The packaging signal contains an essential packaging nucleic acid sequence and a non-essential nucleic acid sequence. The packaging signal lacks gag gene sequences, and has approximately one order of magnitude greater infectivity than retrovirus-derived packaging signals without gag gene sequences. The packaging signal of the invention can be used to transmit genetic material for gene therapy, cell therapy, or other biotechnological applications.

1 Claim, 19 Drawing Sheets

Figure 1
pVLSIB
pVLMB1,2
pBAG
pVLBIRY
pLN-B
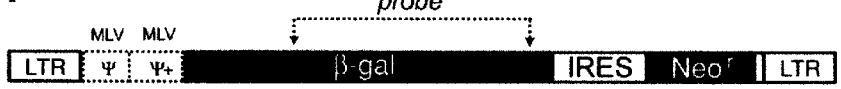
1KB

Figure 2

```
> MoMLV Ψ packaging signal (1-222)
          10         20         30         40         50         60         70         80         90        100
           *          *          *          *          *          *          *          *          *          *
  TTTGGGGGCT CGTCCGGGAT CGGGAGACCC CTGCCCAGGG ACCACCGACC CACCACCGGG AGGTAAGCTG GCCAGCAACT TATCTGTGTC TGTCCGATTG 110        120        130        140        150        160        170        180        190        200
           *          *          *          *          *          *          *          *          *          *
  TCTAGTGTCT ATGACTGATT TTATGCGCCT GCGTCGGTAC TAGTTAGCTA ACTAGCTCTG TATCTGGCGG ACCCGTGGTG GAACTGACGA GTTCGGAACA

|> VL30 Ψ+ packaging signal (224-900)
                   >AatII
         210        220    |   230        240        250        260        270        280        290        300
           *          *          *          *          *          *          *          *          *          *
  CCCGGCCGCA ACCCTGGGAG ACGTCCCAGG AGGAACAGGG GAGGATCAGG GACGCCTGGT GGACCCCTTT GAAGGCCAAG AGACCATTTG GGGTTGCGAG 310        320        330        340        350        360        370        380        390        400
           *          *          *          *          *          *          *          *          *          *
  ATCGTGGGTT CGAGTCCCAC CTCGTGCCCA GTTGCGAGAT CGTGGGTTCG AGTCCCACCT CGTGTTTTGT TCGAGTCCCC ACCTCGTTTG TGGTTCGAGT 410        420        430        440        450        460        470        480        490        500
           *          *          *          *          *          *          *          *          *          *
  CGTCTGGTCA CGGGATCGTG GGTTCGAGTC CCACCTCGTG TTTTGTTGCG AGATCGTGGG TTCGAGTCCC ACCTCGCGTC TGGTCACGGG ATCGTGGGTT 510        520        530        540        550        560        570        580        590        600
           *          *          *          *          *          *          *          *          *          *
  CGAGTCCCAC CTCGTGCAGA GGGTCTCAAT TGGCCGGGCC TAGAGAGGCC ATCTGATTCT CTTTTTGTCT TTCGAGTTCT CTGTGTTTCT GTGTGTGTCT TTTGTGTTCA GACTTGGACT 610        620        630        640        650        660        670        680        690        700
           *          *          *          *          *          *          *          *          *          *
  CGAGTCCCAC CTCGTGCAGA GGGTCTCAAT TGGCCGGGCC TAGAGAGGCC ATCTGATTCT CTTTTTGTCT TAGTCTCGTG TCCGCTCTTG 710        720        730        740        750        760        770        780        790        800
           *          *          *          *          *          *          *          *          *          *
  TTTGACTAC TGTTTTTCTA AAAATGGGAC AATCTGTGTC CACTCCCCTT TCTCTGACTC TGGTTCTGTC GCTTGGTAAT TTTGTTTGTT TACGTTTGTT End of pVLMB vector packaging signal>|
         810        820        830        840        850        860        870        880        890        900
           *          *          *          *          *          *          *          *          *          *
  TTTGTGAGTC GTCTATGTTG TCTGTTACTA TCTTGTTTTT GTTTGTGGTT TACGGTTTCT GTGTGTGTCT TGTGTGTGTT CA GACTTGGACT
  GATGACTGAC GACTGTTTTT AAGTTATGCC TTCTAAAATA AGCCTAAAAA TCCTGTCAGA TCCCTATGCT GACCACTTCC TTTCAGATCA ACAGCTGCCC
```

Figure 3
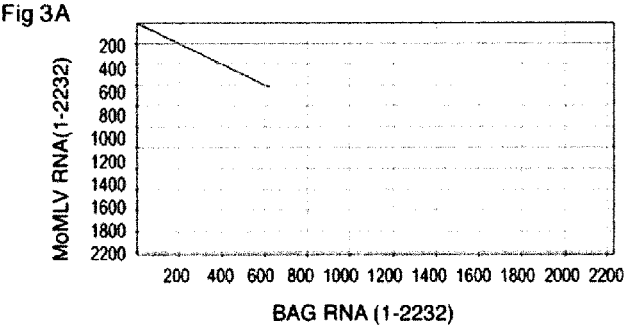
Fig 3A
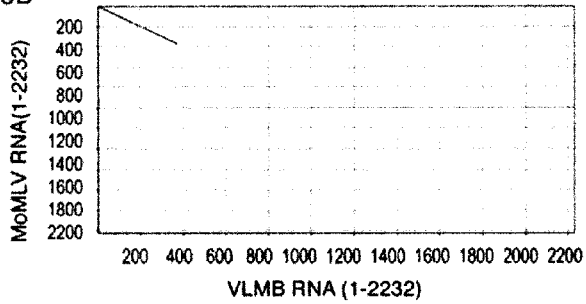
Fig 3B
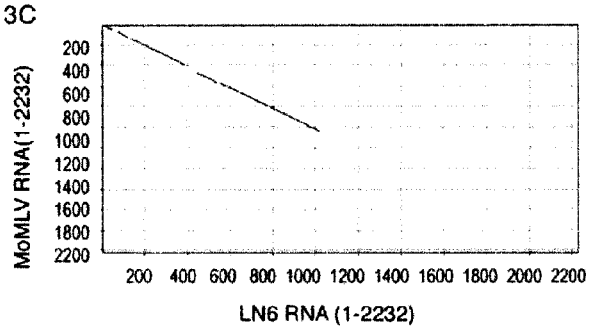
Fig 3C
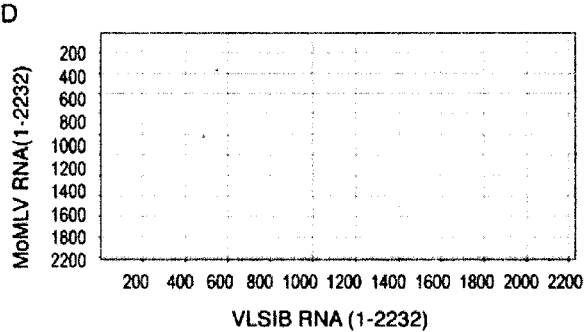
Fig 3D
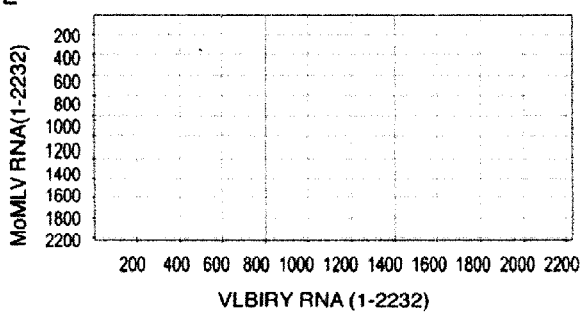
Fig 3E

Fig. 4A

CAP
↓                                                                    R◄─┬─►U₅
GCGCCAGUCCUCCGAUUGACUGAGUCGCCCGGGUACCCGUGUAUCCAAUAAACCCUCUUGCAGUUGCAUCCGACUUGUGGUCUCGCUGUU
                                                                                                                                        90

U₅◄─┐
CCUUGGGAGGGUCUCCUCUGAGUGAUUGACUACCCGUCAGCGGGGGUCUUUCAUUUGGGGGCUCGUCCGGGAUCGGGAGACCCCUGCCCA
                                        ⎵_____⎵⎵_____⎵              180
                                                I.R.                    P.B.S

GGGACCACCGACCCACCACCGGGAGGUAAGCUGGCCAGCAACUUAUCUGUGUCUGUCCGAUUGUCUAGUGUCUAUGACUGAUUUUAUGCG
            ⎵___⎵                                                                              270
             S.D.

LeuThrSerSerValSerGlyGlyProValValGluLeuThrSerSerGluHisProAlaAlaThrLeuGly
CCUGCGUCGGUACUAGUUAGCUAACUAGCUCUGUAUCUGGCGGACCCGUGGUGGAACUGACGAGUUCGGAACACCCGGCCGCAACCCUGG
                                                                                                                                        360

AspValProGlyThrSerGlyAlaValPheValAlaArgProGluSerLysAsnProAspArgPheGlyLeuPheGlyAlaProProLeu
GAGACGUCCCAGGGACUUCGGGGGCCGUUUUUGUGGCCCGACCUGAGUCCAAAAAUCCCGAUCGUUUUGGACUCUUUGGUGCACCCCCU
                                                                                                                                        450

GluGluGlyTyrValValLeuValGlyAspGluAsnLeuLysGlnPheProProProSerGluPheLeuLeuSerValTrpAspArgSer
UAGAGGAGGGAUAUGUGGUUCUGGUAGGAGACGAGAACCUAAAAACAGUUCCCGCCUCCGUCGAAUUUUUGCUUUCGGUUUGGGACCGAA
                                                                                                                                        540

┌──►p15
    ArgAlaAlaArgLeuValCysCysSerIleValLeuCysCysLeuCysLeuThrValPheLeuTyrLeuSerGluAsnMetGlyGlnThr
GCCGCGCCGCGCGUCUGUCUGCUGCAGCAUCGUUCUGUGUUGUCUCUGUCUGACUGUGUUUCUGUAUUUGUCGAGAAUAUGGGCCAGA
                                                                                                                                        630
                                                                                                                    └──►gag ValThrThrProLeuSerLeuThrLeuGlyHisTrpLysAspValGluArgIleAlaHisAsnGlnSerValAspValLysLysArgArg
CUGUUACCACUCCCUUAAGUUUGACCUUAGGUCACUGGAAAGAUGUCGAGCGGAUCGCUCACAACCAGUCGGUAGAUGUCAAGAAGAGAC
                                                                                                                                        720

TrpValThrPheCysSerAlaGluTrpProThrPheAsnValGlyTrpProArgAspGlyThrPheAsnArgAspLeuIleThrGlnVal
GUUGGGUUACUUUCUGCUCUGCAGAAUGGCCAACCUUUAACGUCGGAUGGCCGCGAGACGGCACCUUUAACCGAGACCUCAUCACCCAGG
                                                                                                                                        810

LysIleLysValPheSerProGlyProHisGlyHisProAspGlnValProTyrIleValThrTrpGluAlaLeuAlaPheAspProPro
UUAAGAUCAAGGUCUUUUCACCUGGCCCGCAUGGACACCCAGACCAGGUCCCCUACAUCGUGACCUGGGAAGCCUUGGCUUUUGACCCCC
                                                                                                                                        900

ProTrpValLysProPheValHisProLysProProProLeuProProSerAlaProSerLeuProLeuGluProProArgSerThr
CUCCCUGGGUCAAGCCCUUUGUACACCCUAAGCCUCCGCCUCCUCUUCCUCCAUCCGCCCCGUCUCUCCCCCUUGAACCUCCUCGUUCGA
                                                                                                                                        990 p15◄─┬─►p12
    ProProArgSerSerLeuTyrProAlaLeuThrProSerLeuGlyAlaLysProLysProGlnValLeuSerAspSerGlyGlyProLeu
CCCCGCCUCGAUCCUCCCUUUAUCCAGCCCUCACUCCUUCUCUAGGCGCCAAACCUAAACCUCAAGUUCUUUCUGACAGUGGGGGGCCGC
                                                                                                                                        1080

IleAspLeuLeuThrGluAspProProProTyrArgAspProArgProProProSerAspArgAspGlyAsnGlyGlyGluAlaThrPro
UCAUCGACCUACUUACAGAAGACCCCCCGCCUUAUAGGGACCCAAGACCACCCCCUUCCGACAGGGACGGAAAUGGUGGAGAAGCGACCC
                                                                                                                                        1170

AlaGlyGluAlaProAspProSerProMetAlaSerArgLeuArgGlyArgArgGluProProValAlaAspSerThrThrSerGlnAla
CUGCGGGAGAGGCACCGGACCCCUCCCCAAUGGCAUCUCGCCUACGUGGGAGACGGGAGCCCCCGUGGCCGACUCCACUACCUCGCAGG
                                                                                                                                        1260 p12◄─┬─►p30
    PheProLeuArgAlaGlyGlyAsnGlyGlnLeuGlnTyrTrpProPheSerSerSerAspLeuTyrAsnTrpLysAsnAsnAsnProSer
CAUUCCCCCUCCGCGCAGGAGGAAACGGACAGCUUCAAUACUGGCCGUUCUCCUCUUCUGACCUUUACAACUGGAAAAAUAAUAACCCUU
                                                                                                                                        1350

Fig. 4B

```
        PheSerGluAspProGlyLysLeuThrAlaLeuIleGluSerValLeuIleThrHisGlnProThrTrpAspAspCysGlnGlnLeuLeu
        CUUUUUCUGAAGAUCCAGGUAAACUGACAGCUCUGAUCGAGUCUGUUCUCAUCACCCAUCAGCCCACCUGGGACGACUGUCAGCAGCUGU
                                                                                              1440

GlyThrLeuLeuThrGlyGluGluLysGlnArgValLeuLeuGluAlaArgLysAlaValArgGlyAspAspGlyArgProThrGlnLeu
        UGGGGACUCUGCUGACCGGAGAAGAAAAACAACGGGUGCUCUUUAGAGGCUAGAAAGGCGGUGCGGGGCGAUGAUGGGCGCCCCACUCAAC
                                                                                              1530
                                                       N⁺B⁺
        ProAsnGluValAspAlaAlaPheProLeuGluArgProAspTrpAspTyrThrThrGlnAlaGlyArgAsnHisLeuValHisTyrArg
        UGCCCAAUGAAGUCGAUGCCGCUUUUCCCCUCGAGCGCCCAGACUGGGAUUACACCACCCAGGCAGGUAGGAACCACCUAGUCCACUAUC
                                                                                              1620

GlnLeuLeuLeuAlaGlyLeuGlnAsnAlaGlyArgSerProThrAsnLeuAlaLysValLysGlyIleThrGlnGlyProAsnGluSer
        GCCAGUUGCUCCUAGCGGGUCUCCAAAACGCGGGCAGAAGCCCCACCAAUUUGGCCAAGGUAAAAGGAAUAACACAAGGGCCCAAUGAGU
                                                                                              1710

ProSerAlaPheLeuGluArgLeuLysGluAlaTyrArgArgTyrThrProTyrAspProGluAspProGlyGlnGluThr AsnValSer
        CUCCCUCGGCCUUCCUAGAGAGACUUAAGGAAGCCUAUCGCAGGUACACUCCUUAUGACCCUGAGGACCCAGGGCAAGAAACUAAUGUGU
                                                                                              1800
                                                                         (Gly)
        MetSerPheIleTrpGlnSerAlaProAspIleGlyArgLysLeuGluArgLeuGluAspLeuLys AsnLysThr LeuGlyAspLeuVal
        CUAUGUCUUUCAUUUGGCAGUCUGCCCCAGACAUUGGGAGAAAGUUAGAGAGGUUAGAAGAUUUAAAAAACAAGACGCUUGGAGAUUUGG
                                                    ↑                                         1890

ArgGluAlaGluLysIlePheAsnLysArgGluThrProGluGluArgGluGluArgIleArgArgGluThrGluGluLysGluGluArg
        UUAGAGAGGCAGAAAAGAUCUUUAAUAAACGAGAAACCCCGGAAGAAAGAGAGGAACGUAUCAGGAGAGAAACAGAGGAAAAAGAAGAAC
                                                                                              1980
                                                                        p30 ←┬→ p10
        ArgArgThrGluAspGluGlnLysGluLysGluArgAspArgArgArgHisArgGluMetSerLysLeuLeuAlaThrValValSerGly
        GCCGUAGGACAGAGGAUGAGCAGAAAGAGAAAGAAAGAGAUCGUAGGAGACAUAGAGAGAUGAGCAAGCUAUUGGCCACUGUCGUUAGUG
                                                                                              2070

GlnLysGlnAspArgGlnGlyGlyGluArgArgArgSerGlnLeuAspArgAspGlnCysAlaTyrCysLysGluLysGlyHisTrpAla
        GACAGAAACAGGAUAGACAGGGAGGAGAACGAAGGAGGUCCCAACUCGAUCGCGACCAGUGUGCCUACUGCAAAGAAAAGGGGCACUGGG
                                                                                              2160
                                                       p10 ←┐          (Gln)
        LysAspCysProLysLysProArgGlyProArgGlyProArgGlnThrSerLeuLeuAspAsp***GlyGlyGlnGlyGln
        CUAAAGAUUGUCCCAAGAAACCACGAGGACCUCGGGGACCAAGACCCCAGACCCUCCCUCCUGACCCUAGAUGACUAGGGAGGUCAGGGUC
                                                                                              2250
                                                          ↳ pol      gag ←┘
        (Asp)
        GluProProProGluProArgIleThrLeuLysValGlyGlyGlnProValThrPheLeuValAspThrGlyAlaGlnHisSerValLeu
        AGGAGCCCCCCCCUGAACCCAGGAUAACCCUCAAAGUCGGGGGGCAACCCGUCACCUUCCUGGUAGAUACUGGGGCCCAACACUCCGUGC
         ↑                                                                                    2340

ThrGlnAsnProGlyProLeuSerAspLysSerAlaTrpValGlnGlyAlaThrGlyGlyLysArgTyrArgTrpThrThrAspArgLys
        UGACCCAAAAUCCUGGACCCCUAAGUGAUAAGUCUGCCUGGGUCCAAGGGGCUACUGGAGGAAAGCGGUAUCGCUGGACCACGGAUCGCA
                                                                                              2430

ValHisLeuAlaThrGlyLysValThrHisSerPheLeuHisValProAspCysProTyrProLeuLeuGlyArgAspLeuLeuThrLys
        AAGUACAUCUAGCUACCGGUAAGGUCACCCACUCUUUCCUCCAUGUACCAGACUGUCCCUAUCCUCUGUUAGGAAGAGAUUUGCUGACUA
                                                                                              2520
                                                                                   ┌→ RT
        LeuLysAlaGlnIleHisPheGluGlySerGlyAlaGlnValMetGlyProMetGlyGlnProLeuGlnValLeuThrLeuAsnIleGlu
        AACUAAAAGCCCAAAUCCACUUUGAGGGAUCAGGAGCUCAGGUUAUGGGACCAAUGGGGCAGCCCCUGCAAGUGUUGACCCUAAAUAUAG
                                                                                              2610
```

Fig. 4C

```
         AspGluHisArgLeuHisGluThrSerLysGluProAspValSerLeuGlySerThrTrpLeuSerAspPheProGlnAlaTrpAlaGlu
AAGAUGAGCAUCGGCUACAUGAGACCUCAAAAGAGCCAGAUGUUUCUCUAGGGUCCACAUGGCUGUCUGAUUUUCCUCAGGCCUGGGCGG
                                                                                         2700

ThrGlyGlyMetGlyLeuAlaValArgGlnAlaProLeuIleIleProLeuLysAlaThrSerThrProValSerIleLysGlnTyrPro
AAACCGGGGCAUGGGACUGGCAGUUCGCCAAGCUCCUCUGAUCAUACCUCUGAAAGCAACCUCUACCCCCGUGUCCAUAAAACAAUACC
                                                                                         2790

MetSerGlnGluAlaArgLeuGlyIleLysProHisIleGlnArgLeuLeuAspGlnGlyIleLeuValProCysGlnSerProTrpAsn
CCAUGUCACAAGAAGCCAGACUGGGGAUCAAGCCCCACAUACAGAGACUGUUGGACCAGGGAAUACUGGUACCCUGCCAGUCCCCUGGA
                                                                                         2880

ThrProLeuLeuProValLysLysProGlyThrAsnAspTyrArgProValGlnAspLeuArgGluValAsnLysArgValGluAspIle
ACACGCCCCUGCUACCCGUUAAGAAACCAGGGACUAAUGAUUAUAGGCCUGUCCAGGAUCUGAGAGAAGUCAACAAGCGGGUGGAAGACA
                                                                                         2970

HisProThrValProAsnProTyrAsnLeuLeuSerGlyLeuProProSerHisGlnTrpTyrThrValLeuAspLeuLysAspAlaPhe
UCCACCCCACCGUGCCCAACCCUUACAACCUCUUGAGCGGGCUCCCACCGUCCCACCAGUGGUACACUGUGCUUGAUUUAAAGGAUGCCU
                                                                                         3060

PheCysLeuArgLeuHisProThrSerGlnProLeuPheAlaPheGluTrpArgAspProGluMetGlyIleSerGlyGlnLeuThrTrp
UUUUCUGCCUGAGACUCCACCCCACCAGUCAGCCUCUCUUCGCCUUUGAGUGGAGAGAUCCAGAGAUGGGAAUCUCAGGACAAUUGACCU
                                                                                         3150

ThrArgLeuProGlnGlyPheLysAsnSerProThrLeuPheAspGluAlaLeuHisArgAspLeuAlaAspPheArgIleGlnHisPro
GGACCAGACUCCCACAGGGUUUCAAAAACAGUCCCACCCUGUUUGAUGAGGCACUGCACAGAGACCUAGCAGACUUCCGGAUCCAGCACC
                                                                                         3240

AspLeuIleLeuLeuGlnTyrValAspAspLeuLeuLeuAlaAlaThrSerGluLeuAspCysGlnGlnGlyThrArgAlaLeuLeuGln
CAGACUUGAUCCUGCUACAGUACGUGGAUGACUUACUGCUGGCCGCCACUUCUGAGCUAGACUGCCAACAAGGUACUCGGGCCCUGUUAC
                                                                                         3330

ThrLeuGlyAsnLeuGlyTyrArgAlaSerAlaLysLysAlaGlnIleCysGlnLysGlnValLysTyrLeuGlyTyrLeuLeuLysGlu
AAACCCUAGGGAACCUCGGGUAUCGGGCCUCGGCCAAGAAAGCCCAAAUUUGCCAGAAACAGGUCAAGUAUCUGGGGUAUCUUCUAAAAG
                                                                                         3420

GlyGlnArgTrpLeuThrGluAlaArgLysGluThrValMetGlyGlnProThrProLysThrProArgGlnLeuArgGluPheLeuGly
AGGGUCAGAGAUGGCUGACUGAGGCCAGAAAAGAGACUGUGAUGGGGCAGCCUACUCCGAAGACCCCUCGACAACUAAGGGAGUUCCUAG
                                                                                         3510

ThrAlaGlyPheCysArgLeuTrpIleProGlyPheAlaGluMetAlaAlaProLeuTyrProLeuThrLysThrGlyThrLeuPheAsn
GGACGGCAGGCUUCUGUCGCCUCUGGAUCCCUGGGUUUGCAGAAAUGGCAGCCCCCUUGUACCCUCUCACCAAAACGGGGACUCUGUUUA
                                                                                         3600

TrpGlyProAspGlnGlnLysAlaTyrGlnGluIleLysGlnAlaLeuLeuThrAlaProAlaLeuGlyLeuProAspLeuThrLysPro
AUUGGGGCCCAGACCAACAAAAGGCCUAUCAAGAAAUCAAGCAAGCUCUUCUAACUGCCCCAGCCCUGGGGUUGCCAGAUUUGACUAAGC
                                                                                         3690

PheGluLeuPheValAspGluLysGlnGlyTyrAlaLysGlyValLeuThrGlnLysLeuGlyProTrpArgArgProValAlaTyrLeu
CCUUUGAACUCUUUGUCGACGAGAAGCAGGGCUACGCCAAAGGUGUCCUAACGCAAAAACUGGGACCUUGGCGUCGGCCGGUGGCCUACC
                                                                                         3780

SerLysLysLeuAspProValAlaAlaGlyTrpProProCysLeuArgMetValAlaAlaIleAlaValLeuThrLysAspAlaGlyLys
UGUCCAAAAAGCUAGACCCAGUAGCAGCUGGGUGGCCCCCUUGCCUACGGAUGGUAGCAGCCAUUGCCGUACUGACAAAGGAUGCAGGCA
                                                                                         3870
```

Fig. 4D

```
          LeuThrMetGlyGlnProLeuValIleLeuAlaProHisAlaValGluAlaLeuValLysGlnProProAspArgTrpLeuSerAsnAla
          AGCUAACCAUGGGACAGCCACUAGUCAUUCUGGCCCCCCAUGCAGUAGAGGCACUAGUCAAACAACCCCCGACCGCUGGCUUUCCAACG
                                                                                              3960

ArgMetThrHisTyrGlnAlaLeuLeuLeuAspThrAspArgValGlnPheGlyProValValAlaLeuAsnProAlaThrLeuLeuPro
          CCCGGAUGACUCACUAUCAGGCCUUGCUUUUGGACACGGACCGGGUCCAGUUCGGACCGGUGGUAGCCCUGAACCCGGCUACGCUGCUCC
                                                                                              4050

LeuProGluGluGlyLeuGlnHisAsnCysLeuAspIleLeuAlaGluAlaHisGlyThrArgProAspLeuThrAspGlnProLeuPro
          CACUGCCUGAGGAAGGGCUGCAACACAACUGCCUUGAUAUCCUGGCCGAAGCCCACGGAACCCGACCCGACCUAACGGACCAGCCGCUCC
                                                                                              4140

AspAlaAspHisThrTrpTyrThrAspGlySerSerLeuLeuGlnGluGlyGlnArgLysAlaGlyAlaAlaValThrThrGluThrGlu
          CAGACGCCGACCACACCUGGUACACGGAUGGAAGCAGUCUCUUACAAGAGGGACAGCGUAAGGCGGGAGCUGCGGUGACCACCGAGACCG
                                                                                              4230

ValIleTrpAlaLysAlaLeuProAlaGlyThrSerAlaGlnArgAlaGluLeuIleAlaLeuThrGlnAlaLeuLysMetAlaGluGly
          AGGUAAUCUGGGCUAAAGCCCUGCCAGCCGGGACAUCCGCUCAGCGGGCUGAACUGAUAGCACUCACCCAGGCCCUAAAGAUGGCAGAAG
                                                                                              4320

LysLysLeuAsnValTyrThrAspSerArgTyrAlaPheAlaThrAlaHisIleHisGlyGluIleTyrArgArgArgGlyLeuLeuThr
          GUAAGAAGCUAAAUGUUUAUACUGAUAGCCGUUAUGCUUUUGCUACUGCCCAUAUCCAUGGAGAAAUAUACAGAAGGCGUGGGUUGCUCA
                                                                                              4410

SerGluGlyLysGluIleLysAsnLysAspGluIleLeuAlaLeuLeuLysAlaLeuPheLeuProLysArgLeuSerIleIleHisCys
          CAUCAGAAGGCAAAGAGAUCAAAAAUAAAGACGAGAUCUUGGCCCUACUAAAAGCCCUCUUUCUGCCCAAAAGACUUAGCAUAAUCCAUU
                                                                                              4500

ProGlyHisGlnLysGlyHisSerAlaGluAlaArgGlyAsnArgMetAlaAspGlnAlaAlaArgLysAlaAlaIleThrGluThrPro
          GUCCAGGACAUCAAAAGGGACACAGCGCCGAGGCUAGAGGCAACCGGAUGGCUGACCAAGCGGCCCGAAAGGCAGCCAUCACAGAGACUC
                                                                                              4590

AspThrSerThrLeuLeuIleGluAsnSerSerProTyrThrSerGluHisPheHisTyrThrValThrAspIleLysAspLeuThrLys
          CAGACACCUCUACCCUCCUCAUAGAAAAUUCAUCACCCUACACCUCAGAACAUUUUCAUUACACAGUGACUGAUAUAAAGGACCUAACCA
                                                                                              4680

LeuGlyAlaIleTyrAspLysThrLysLysTyrTrpValTyrGlnGlyLysProValMetProAspGlnPheThrPheGluLeuLeuAsp
          AGUUGGGGGCCAUUUAUGAUAAAACAAAGAAGUAUUGGGUCUACCAAGGAAAACCUGUGAUGCCUGACCAGUUUACUUUUGAAUUAUUAG
                                                                                              4770

PheLeuHisGlnLeuThrHisLeuSerPheSerLysMetLysAlaLeuLeuGluArgSerHisSerProTyrTyrMetLeuAsnArgAsp
          ACUUUCUUCAUCAGCUGACUCACCUCAGCUUCUCAAAAAUGAAGGCUCUCCUAGAGAGAAGCCACAGUCCCUACUACAUGCUGAACCGGG
                                                                                              4860

ArgThrLeuLysAsnIleThrGluThrCysLysAlaCysAlaGlnValAsnAlaSerLysSerAlaValLysGlnGlyThrArgValArg
          AUCGAACACUCAAAAAUAUCACUGAGACCUGCAAAGCUUGUGCACAAGUCAACGCCAGCAAGUCUGCCGUUAAACAGGGAACUAGGGUCC
                                                                                              4950

GlyHisArgProGlyThrHisTrpGluIleAspPheThrGluIleLysProGlyLeuTyrGlyTyrLysTyrLeuLeuValPheIleAsp
          GCGGGCAUCGGCCCGGCACUCAUUGGGAGAUCGAUUUCACCGAGAUAAAGCCCGGAUUGUAUGGCUAUAAAUAUCUUCUAGUUUUUAUAG
                                                                                              5040

ThrPheSerGlyTrpIleGluAlaPheProThrLysLysGluThrAlaLysValValThrLysLysLeuLeuGluGluIlePheProArg
          AUACCUUUUCUGGCUGGAUAGAAGCCUUCCCAACCAAGAAAGAAACCGCCAAGGUCGUAACCAAGAAGCUACUAGAGGAGAUCUUCCCCA
                                                                                              5130
```

Fig. 4E

```
           PheGlyMetProGlnValLeuGlyThrAspAsnGlyProAlaPheValSerLysValSerGlnThrValAlaAspLeuLeuGlyIleAsp
           GGUUCGGCAUGCCUCAGGUAUUGGGAACUGACAAUGGGCCUGCCUUCGUCUCCAAGGUGAGUCAGACAGUGGCCGAUCUGUUGGGGAUUG
                                                                                                5220

TrpLysLeuHisCysAlaTyrArgProGlnSerSerGlyGlnValGluArgMetAsnArgThrIleLysGluThrLeuThrLysLeuThr
           AUUGGAAAUUACAUUGUGCAUACAGACCCCAAAGCUCAGGCCAGGUAGAAAGAAUGAAUAGAACCAUCAAGGAGACUUUAACUAAAUUAA
                                                                                                5310

LeuAlaThrGlySerArgAspTrpValLeuLeuLeuProLeuAlaLeuTyrArgAlaArgAsnThrProGlyProHisGlyLeuThrPro
           CGCUUGCAACUGGCUCUAGAGACUGGGUGCUCCUACUCCCCUUAGCCCUGUACCGAGCCCGCAACACGCCGGGCCCCAUGGCCUCACCC
                                                                                                5400

TyrGluIleLeuTyrGlyAlaProProProLeuValAsnPheProAspProAspMetThrArgValThrAsnSerProSerLeuGlnAla
           CAUAUGAGAUCUUAUAUGGGGCACCCCCGCCCCUUGUAAACUUCCCUGACCCUGACAUGACAAGAGUUACUAACAGCCCCUCUCUCCAAG
                                                                                          ‾‾‾‾‾‾‾
                                                                                            S.A.
           HisLeuGlnAlaLeuTyrLeuValGlnHisGluValTrpArgProLeuAlaAlaAlaTyrGlnGluGlnLeuAspArgProValValPro
           CUCACUUACAGGCUCUCUACUUAGUCCAGCACGAAGUCUGGAGACCUCUGGCGGCAGCCUACCAAGAACAACUGGACCGACCGGUGGUAC
                                                                                                5580

HisProTyrArgValGlyAspThrValTrpValArgArgHisGlnThrLysAsnLeuGluProArgTrpLysGlyProTyrThrValLeu
           CUCACCCUUACCGAGUCGGCGACACAGUGUGGGUCCGCCGACACCAGACUAAGAACCUAGAACCUCGCUGGAAAGGACCUUACACAGUCC
                                                                                                5670

LeuThrThrProThrAlaLeuLysValAspGlyIleAlaAlaTrpIleHisAlaAlaHisValLysAlaAlaAspProGlyGlyGlyPro
           UGCUGACCACCCCCACCGCCCUCAAAGUAGACGGCAUCGCAGCUUGGAUACACGCCGCCCACGUGAAGGCUGCCGACCCCGGGGUGGAC
                                                                                                5760

MetAlaArgSerThrLeuSerLysProLeuLysAsnLysValAsnProArgGlyProLeuIleProLeuIleLeu
               SerSerArgLeuThrTrpArgValGlnArgSerGlnAsnProLeuLysIleArgLeuThrArgGluAlaPro***
           CAUCCUCUAGACUGACAUGGCGCGUUCAACGCUCUCAAAACCCCUUAAAAAUAAGGUUAACCCGCGAGGCCCCCUAAUCCCCUUAAUUCU
                     ↳env                                                                      5850
                          ┌→gp70                                                pol ↵

LeuMetLeuArgGlyValSerThrAlaSerProGlySerSerProHisGlnValTyr|AsnIleThr|TrpGluValThrAsnGlyAspArg
           UCUGAUGCUCAGAGGGGUCAGUACUGCUUCGCCCGGCUCCAGUCCUCAUCAAGUCUAUAAUAUCACCUGGGAGGUAACCAAUGGAGAUCG
                                                                                                5940

GluThrValTrpAlaThrSerGlyAsnHisProLeuTrpThrTrpTrpProAspLeuThrProAspLeuCysMetLeuAlaHisHisGly
           GGAGACGGUAUGGGCAACUUCUGGCAACCACCCUCUGUGGACCUGGUGGCCUGACCUUACCCCAGAUUUAUGUAUGUUAGCCCACCAUGG
                                                                                                6030

ProSerTyrTrpGlyLeuGluTyrGlnSerProPheSerSerProProGlyProProCysCysSerGlyGlySerSerProGlyCysSer
           ACCAUCUUAUGGGGGCUAGAAUAUCAAUCCCCUUUUUCUUCUCCCCCGGGGCCCCCUUGUUGCUCAGGGGGCAGCAGCCCAGGCUGUUC
                                                                                                6120

ArgAspCysGluGluProLeuThrSerLeuThrProArgCysAsnThrAlaTrpAsnArgLeuLysLeuAspGlnThrThrHisLysSer
           CAGAGACUGCGAAGAACCUUUAACCUCCCUCACCCCUCGGUGCAACACUGCCUGGAACAGACUCAAGCUAGACCAGACAACUCAUAAAUC
                                                                                                6210

AsnGluGlyPheTyrValCysProGlyProHisArgProArgGluSerLysSerCysGlyGlyProAspSerPheTyrCysAlaTyrTrp
           AAAUGAGGGAUUUUAUGUUUGCCCCGGGCCCCACCGCCCCGAGAAUCCAAGUCAUGUGGGGUCCAGAUCCUUCUACUGUGCCUAUUG
                                                                                                6300

GlyCysGluThrThrGlyArgAlaTyrTrpLysProSerSerSerTrpAspPheIleThrValAsnAsn|AsnLeuThr|SerAspGlnAla
           GGGCUGUGAGACAACCGGUAGAGCUUACUGGAAGCCCUCCUCAUCAUGGGAUUUCAUCACAGUAAACAACAAUCUCACCUCUGACCAGGC
                                                                                                6390
```

Fig. 4F

```
              ValGlnValCysLysAspAsnLysTrpCysAsnProLeuValIleArgPheThrAspAlaGlyArgArgValThrSerTrpThrThrGly
              UGUCCAGGUAUGCAAAGAUAAUAAGUGGUGCAACCCCUUAGUUAUUCGGUUUACAGACGCCGGGAGACGGGUUACUUCCUGGACCACAGG
                                                                                                      6480

HisTyrTrpGlyLeuArgLeuTyrValSerGlyGlnAspProGlyLeuThrPheGlyIleArgLeuArgTyrGlnAsnLeuGlyProArg
              ACAUUACUGGGGCUUACGUUUGUAUGUCUCCGGACAAGAUCCAGGGCUUACAUUUGGGAUCCGACUCAGAUACCAAAAUCUAGGACCCCG
                                                                                                      6570

ValProIleGlyProAsnProValLeuAlaAspGlnGlnProLeuSerLysProLysProValLysSerProSerValThrLysProPro
              CGUCCCAAUAGGGCCAAACCCCGUUCUGGCAGACCAACAGCCACUCUCCAAGCCCAAACCUGUUAAGUCGCCUUCAGUCACCAAACCACC
                                                                                                      6660

SerGlyThrProLeuSerProThrGlnLeuProProAlaGlyThrGluAsnArgLeuLeuAsnLeuValAspGlyAlaTyrGlnAlaLeu
              CAGUGGGACUCCUCUCUCCCUACCCAACUUCCACCGGCGGGAACGGAAAAUAGGCUGCUAAACUUAGUAGACGGAGCCUACCAAGCCCU
                                                                                                      6750

AsnLeuThrSerProAspLysThrGlnGluCysTrpLeuCysLeuValAlaGlyProProTyrTyrGluGlyValAlaValLeuGlyThr
              CAACCUCACCAGUCCUGACAAAACCCAAGAGUGCUGGUUGUGUCUAGUAGCGGGACCCCCCUACUACGAAGGGGUUGCCGUCCUGGGUAC
                                                                                                      6840

TyrSerAsnHisThrSerAlaProAlaAsnCysSerValAlaSerGlnHisLysLeuThrLeuSerGluValThrGlyGlnGlyLeuCys
              CUACUCCAACCAUACCUCUGCUCCAGCCAACUGCUCCGUGGCCUCCCAACACAAGUUGACCCUGUCCGAAGUGACCGGACAGGGACUCUG
                                                                                                      6930

IleGlyAlaValProLysThrHisGlnAlaLeuCysAsnThrThrGlnThrSerSerArgGlySerTyrTyrLeuValAlaProThrGly
              CAUAGGAGCAGUUCCCAAAACACAUCAGGCCCUAUGUAAUACCACCCAGACAAGCAGUCGAGGGUCCUAUUAUCUAGUUGCCCCUACAGG
                                                                                                      7020
                                                                              Gix
              ThrMetTrpAlaCysSerThrGlyLeuThrProCysIleSerThrThrIleLeuAsnLeuThrThrAspTyrCysValLeuValGluLeu
              UACCAUGUGGGCUUGUAGUACCGGGCUUACUCCAUGCAUCUCCACCACCAUACUGAACCUUACCACUGAUUAUUGUGUUCUUGUCGAACU
                                                                                                      7110
                                                                   ┌─ p15E
              TrpProArgValThrTyrHisSerProSerTyrValTyrGlyLeuPheGluArgSerAsnArgHisLysArgGluProValSerLeuThr
              CUGGCCAAGAGUCACCUAUCAUUCCCCCAGCUAUGUUUACGGCCUGUUUGAGAGAUCCAACCGACACAAAAGAGAACCGGUGUCGUUAAC
                                                                                                      7200

LeuAlaLeuLeuLeuGlyGlyLeuThrMetGlyGlyIleAlaAlaGlyIleGlyThrGlyThrThrAlaLeuMetAlaThrGlnGlnPhe
              CCUGGCCCUAUUAUUGGGUGGACUAACCAUGGGGGGAAUUGCCGCUGGAAUAGGAACAGGGACUACUGCUCUAAUGGCCACUCAGCAAUU
                                                                                                      7290

GlnGlnLeuGlnAlaAlaValGlnAspAspLeuArgGluValGluLysSerIleSerAsnLeuGluLysSerLeuThrSerLeuSerGlu
              CCAGCAGCUCCAAGCCGCAGUACAGGAUGAUCUCAGGGAGGUUGAAAAAUCAAUCUCUAACCUAGAAAAGUCUCUCACUUCCCUGUCUGA
                                                                                                      7380

ValValLeuGlnAsnArgArgGlyLeuAspLeuLeuPheLeuLysGluGlyGlyLeuCysAlaAlaLeuLysGluGluCysCysPheTyr
              AGUUGUCCUACAGAAUCGAAGGGGCCUAGACUUGUUAUUUCUAAAAGAAGGAGGGCUGUGUGCUGCUCUAAAAGAAGAAUGUUGCUUCUA
                                                                                                      7470

AlaAspHisThrGlyLeuValArgAspSerMetAlaLysLeuArgGluArgLeuAsnGlnArgGlnLysLeuPheGluSerThrGlnGly
              UGCGGACCACACAGGACUAGUGAGAGACAGCAUGGCCAAAUUGAGAGAGAGGCUUAAUCAGAGACAGAAACUGUUUGAGUCAACUCAAGG
                                                                                                      7560

TrpPheGluGlyLeuPheAsnArgSerProTrpPheThrThrLeuIleSerThrIleMetGlyProLeuIleValLeuLeuMetIleLeu
              AUGGUUUGAGGGACUGUUUAACAGAUCCCCUUGGUUUACCACCUUGAUAUCUACCAUUAUGGGACCCCUCAUUGUACUCCUAAUGAUUUU
                                                                                                      7650
```

Fig. 4G

```
                                                                                              p15E◄─┐
   LeuPheGlyProCysIleLeuAsnArgLeuValGlnPheValLysAspArgIleSerValValGlnAlaLeuValLeuThrGlnGlnTyr
   GCUCUUCGGACCCUGCAUUCUUAAUCGAUUAGUCCAAUUUGUUAAAGACAGGAUAUCAGUGGUCCAGGCUCUAGUUUUGACUCAACAAUA
                                                                                                 7740

HisGlnLeuLysProIleGluTyrGluPro***                                              ┌─►U3
   UCACCAGCUGAAGCCUAUAGAGUACGAGCCAUAGAUAAAAUAAAAGAUUUUAUUUAGUCUCCAGAAAAAGGGGGAAUGAAAGACCCCAC
                                env◄─┘                                                   I.R.

CUGUAGGUUUGGCAAGCUAGCUUAAGUAACGCCAUUUUGCAAGGCAUGGAAAAAUACAUAACUGAGAAUAGAGAAGUUCAGAUCAAGGUC
                                                                                                 7920
      ┌─►D.R.                                                              ┌─►D.R.  D.R.◄─┐
   AGGAACAGAUGGAACAGCUGAAUAUGGGCCAAACAGGAUAUCUGUGGUAAGCAGUUCCUGCCCCGGCUCAGGGCCAAGAACAGAUGGAAC
                                                                                                 8010
                                                                          D.R.◄─┐
   AGCUGAAUAUGGGCCAAACAGGAUAUCUGUGGUAAGCAGUUCCUGCCCCGGCUCAGGGCCAAGAACAGAUGGUCCCCAGAUGCGGUCCAG
                                                                                                 8100

CCCUCAGCAGUUUCUAGAGAACCAUCAGAUGUUUCCAGGGUGCCCCAAGGACCUGAAAUGACCCUGUGCCUUAUUUGAACUAACCAAUCA
                                                                       U3◄─┬─►R       CAT
   GUUCGCUUCUCGCUUCUGUUCGCGCGCUUCUGCUCCCCGAGCUCAAUAAAAGAGCCCACAACCCCUCACUCGGGGCGCCAGUCCUCCGAU
                                                      └──┬──┘                                    8280
                                                        TATA
   UGACUGAGUCGCCCGGGUACCCGUGUAUCCAAUAAACCCUCUUGCAGUUGCA
                                    └──┬──┘             ▲
                                    (A)n signal        (A)n
```

Fig. 5A pVLMB1

AATGAAAGACCCCACCTGTAGGTTTGGCAAGCTAGCTTAAGTAACGCCATTTTGCAAGGCATGGAAAAAT
ACATAACTGAGAATAGAGAAGTTCAGATCAAGGTCAGGAACAGATGGAACAGCTGAATATGGGCCAAACA
GGATATCTGTGGTAAGCAGTTCCTGCCCCGGCTCAGGGCCAAGAACAGATGGAACAGCTGAATATGGGCC
AAACAGGATATCTGTGGTAAGCAGTTCCTGCCCCGGCTCAGGGCCAAGAACAGATGGTCCCCAGATGCGG
TCCAGCCCTCAGCAGTTTCTAGAGAACCATCAGATGTTTCCAGGGTGCCCCAAGGACCTGAAATGACCCT
GTGCCTTATTTGAACTAACCAATCAGTTCGCTTCTCGCTTCTGTTCGCGCGCTTCTGCTCCCCGAGCTCA
ATAAAAGAGCCCACAACCCCTCACTCGGGGCGCCAGTCCTCCGATTGACTGAGTCGCCCGGGTACCCGTG
TATCCAATAAACCCTCTTGCAGTTGCATCCGACTTGTGGTCTCGCTGTTCCTTGGGAGGGTCTCCTCTGA
GTGATTGACTACCCGTCAGCGGGGGTCTTTCATTTGGGGGCTCGTCCGGGATCGGGAGACCCCTGCCCAG
GGACCACCGACCCACCACCGGGAGATAAGCTGGGTCGGAGACCCCTGCCCAGGGACCACCGACCCACCAC
CGGGAGGTAAGCTGGCCAGCAACTTATCTGTGTCTGTCCGATTGTCTAGTGTCTATGACTGATTTTATGC
GCCTGCGTCGGTACTAGTTAGCTAACTAGCTCTGTATCTGGCGGACCCGTGGTGGAACTGACGAGTTCGG
AACACCCGGCCGCAACCCTGGGAGACGTCCCAGGAGGAACAGGGGAGGATCAGGGACGCCTGGTGGACCC
CTTTGAAGGCCAAGAGACCATTTGGGGTTGCGAGATCGTGGGTTCGAGTCCCACCTCGTGCCCAGTTGCG
AGATCGTGGGTTCGAGTCCCACCTCGTGTTTTGTTGCGAGATCGTGGGTTCGAGTCCCACCTCGCGTCTG
GTCACGGGATCGTGGGTTCGAGTCCCACCTCGTGTTTTGTTGCGAGATCGTGGGTTCGAGTCCCACCTCG
CGTCTGGTCACGGGATCGTGGGTTCGAGTCCCACCTCGTGCAGAGGGTCTCAATTGGCCGGCCTTAGAGA
GGCCATCTGATTCTTCTGGTTTCTCTTTTTGTCTTAGTCTCGTGTCCGCTCTTGTTGTGACTACTGTTTT
TCTAAAAATGGGACAATCTGTGTCCACTCCCCTTTCTCTGACTCTGGTTCTGTCGCTTGGTAATTTTGTT
TGTTTACGTTTGTTTTTGTGAGTCGTCTATGTTGTCTGTTACTATCTTGTTTTTGTTTGTGGTTTACGGT
TTCTGTGTGTGTCTTGTGTGTCTCTTTGTGTTCAGACTTGGACTGATGACTGACGACTGTTTTTAAGTTA
TGCCTTCTAAAATAAGCCTAAAAATCCTGTCAGATCCCTATGCTGACCACTTCCTTTCAGATCAACAGCT
GCCCTTACGTATCGATGGATCCCTCGACTAACTAATAGCCCATTCTCCAAGGTCGAGCGGGATCAATTCC
GCCCCCCCCCTAACGTTACTGGCCGAAGCCGCTTGGAATAAGGCCGGTGTGCGTTTGTCTATATGTTATT
TTCCACCATATTGCCGTCTTTTGGCAATGTGAGGGCCCGGAAACCTGGCCCTGTCTTCTTGACGAGCATT
CCTAGGGGTCTTTCCCCTCTCGCCAAAGGAATGCAAGGTCTGTTGAATGTCGTGAAGGAAGCAGTTCCTC
TGGAAGCTTCTTGAAGACAAACAACGTCTGTAGCGACCCTTTGCAGGCAGCGGAACCCCCCACCTGGCGA
CAGGTGCCTCTGCGGCCAAAAGCCACGTGTATAAGATACACCTGCAAAGGCGGCACAACCCCAGTGCCAC
GTTGTGAGTTGGATAGTTGTGGAAAGAGTCAAATGGCTCTCCTCAAGCGTATTCAACAAGGGGCTGAAGG
ATGCCCAGAAGGTACCCCATTGTATGGGATCTGATCTGGGGCCTCGGTGCACATGCTTTACATGTGTTTA
GTCGAGGTTAAAAAAACGTCTAGGCCCCCGAACCACGGGACGTGGTTTTCCTTTGAAAAACACGATAA
TAATCATGGGCGCGGATCCGTCGTTTTACAACGTCGTGACTGGGAAAACCCTGGCGTTACCCAACTTAA
TCGCCTTGCAGCACATCCCCCTTTCGCCAGCTGGCGTAATAGCGAAGAGGCCCGCACCGATCGCCCTTCC
CAACAGTTGCGCAGCCTGAATGGCGAATGGCGCTTTGCCTGGTTTCCGGCACCAGAAGCGGTGCCGGAAA
GCTGGCTGGAGTGCGATCTTCCTGAGGCCGATACTGTCGTCGTCCCCTCAAACTGGCAGATGCACGGTTA
CGATGCGCCCATCTACACCAACGTAACCTATCCCATTACGGTCAATCCGCCGTTTGTTCCCACGGAGAAT
CCGACGGGTTGTTACTCGCTCACATTTAATGTTGATGAAAGCTGGCTACAGGAAGGCCAGACGCGAATTA
TTTTTGATGGCGTTAACTCGGCGTTTCATCTGTGGTGCAACGGGCGCTGGGTCGGTTACGGCCAGGACAG
TCGTTTGCCGTCTGAATTTGACCTGAGCGCATTTTTACGCGCCGGAGAAAACCGCCTCGCGGTGATGGTG
CTGCGTTGGAGTGACGGCAGTTATCTGGAAGATCAGGATATGTGGCGGATGAGCGGCATTTTCCGTGACG
TCTCGTTGCTGCATAAACCGACTACACAAATCAGCGATTTCCATGTTGCCACTCGCTTTAATGATGATTT
CAGCCGCGCTGTACTGGAGGCTGAAGTTCAGATGTGCGGCGAGTTGCGTGACTACCTACGGGTAACAGTT

Fig. 5B

```
TCTTTATGGCAGGGTGAAACGCAGGTCGCCAGCGGCACCGCGCCTTTCGGCGGTGAAATTATCGATGAGC
GTGGTGGTTATGCCGATCGCGTCACACTACGTCTGAACGTCGAAAACCCGAAACTGTGGAGCGCCGAAAT
CCCGAATCTCTATCGTGCGGTGGTTGAACTGCACACCGCCGACGGCACGCTGATTGAAGCAGAAGCCTGC
GATGTCGGTTTCCGCGAGGTGCGGATTGAAAATGGTCTGCTGCTGCTGAACGGCAAGCCGTTGCTGATTC
GAGGCGTTAACCGTCACGAGCATCATCCTCTGCATGGTCAGGTCATGGATGAGCAGACGATGGTGCAGGA
TATCCTGCTGATGAAGCAGAACAACTTTAACGCCGTGCGCTGTTCGCATTATCCGAACCATCCGCTGTGG
TACACGCTGTGCGACCGCTACGGCCTGTATGTGGTGGATGAAGCCAATATTGAAACCCACGGCATGGTGC
CAATGAATCGTCTGACCGATGATCCGCGCTGGCTACCGGCGATGAGCGAACGCGTAACGCGAATGGTGCA
GCGCGATCGTAATCACCCGAGTGTGATCATCTGGTCGCTGGGGAATGAATCAGGCCACGGCGCTAATCAC
GACGCGCTGTATCGCTGGATCAAATCTGTCGATCCTTCCCGCCCGGTGCAGTATGAAGGCGGCGGAGCCG
ACACCACGGCCACCGATATTATTTGCCCGATGTACGCGCGCGTGGATGAAGACCAGCCCTTCCCGGCTGT
GCCGAAATGGTCCATCAAAAAATGGCTTTCGCTACCTGGAGAGACGCGCCCGCTGATCCTTTGCGAATAC
GCCCACGCGATGGGTAACAGTCTTGGCGGTTTCGCTAAATACTGGCAGGCGTTTCGTCAGTATCCCCGTT
TACAGGGCGGCTTCGTCTGGGACTGGGTGGATCAGTCGCTGATTAAATATGATGAAAACGGCAACCCGTG
GTCGGCTTACGGCGGTGATTTTGGCGATACGCCGAACGATCGCCAGTTCTGTATGAACGGTCTGGTCTTT
GCCGACCGCACGCCGCATCCAGCGCTGACGGAAGCAAAACACCAGCAGCAGTTTTTCCAGTTCCGTTTAT
CCGGGCAAACCATCGAAGTGACCAGCGAATACCTGTTCCGTCATAGCGATAACGAGCTCCTGCACTGGAT
GGTGGCGCTGGATGGTAAGCCGCTGGCAAGCGGTGAAGTGCCTCTGGATGTCGCTCCACAAGGTAAACAG
TTGATTGAACTGCCTGAACTACCGCAGCCGGAGAGCGCCGGGCAACTCTGGCTCACAGTACGCGTAGTGC
AACCGAACGCGACCGCATGGTCAGAAGCCGGGCACATCAGCGCCTGGCAGCAGTGGCGTCTGGCGGAAAA
CCTCAGTGTGACGCTCCCCGCCGCGTCCCACGCCATCCCGCATCTGACCACCAGCGAAATGGATTTTTGC
ATCGAGCTGGGTAATAAGCGTTGGCAATTTAACCGCCAGTCAGGCTTTCTTTCACAGATGTGGATTGGCG
ATAAAAAACAACTGCTGACGCCGCTGCGCGATCAGTTCACCCGTGCACCGCTGGATAACGACATTGGCGT
AAGTGAAGCGACCCGCATTGACCCTAACGCCTGGGTCGAACGCTGGAAGGCGGCGGGCCATTACCAGGCC
GAAGCAGCGTTGTTGCAGTGCACGGCAGATACACTTGCTGATGCGGTGCTGATTACGACCGCTCACGCGT
GGCAGCATCAGGGGAAAACCTTATTTATCAGCCGGAAAACCTACCGGATTGATGGTAGTGGTCAAATGGC
GATTACCGTTGATGTTGAAGTGGCGAGCGATACACCGCATCCGGCGCGGATTGGCCTGAACTGCCAGCTG
GCGCAGGTAGCAGAGCGGGTAAACTGGCTCGGATTAGGGCCGCAAGAAAACTATCCCGACCGCCTTACTG
CCGCCTGTTTTGACCGCTGGGATCTGCCATTGTCAGACATGTATACCCCGTACGTCTTCCCGAGCGAAAA
CGGTCTGCGCTGCGGGACGCGCGAATTGAATTATGGCCCACACCAGTGGCGCGGCGACTTCCAGTTCAAC
ATCAGCCGCTACAGTCAACAGCAACTGATGGAAACCAGCCATCGCCATCTGCTGCACGCGGAAGAAGGCA
CATGGCTGAATATCGACGGTTTCCATATGGGGATTGGTGGCGACGACTCCTGGAGCCCGTCAGTATCGGC
GGAATTCCAGCTGAGCGCCGGTCGCTACCATTACCAGTTGGTCTGGTGTCAAAAATAATAATAACCGGGC
AGGGGGGATCCGAAGGCGGGGACAGCAGTGCAGTGGTGGACAGAAAGCAAGTGATCTAGGCCAGCAGCCT
CCCTAAAGGGACTTCAGCCCACAAAGCCAAACTTGTGGCTTTAATACAAGCTCTGTAAATGGTAAAAAAA
AAAAAGTCTACACGGACAGCAGGTATGCTCTTGCCACTGTACAGAGCAATATACAGACAAAGAGAACTGT
TGACATCTGCAGAGAAAGACCTAAGATGCTGTGGCTAAAAGAAATCAGATGGCAAATCTAACCGCCCAGG
CATCCTAAAGAGCAATGATCCTGACAGTCTGAAGACTATCAAGTTATAGACAAATTAAGACTGGTAAAAA
AAACCCTGTATAAAATAGTAAAAACTGAAAAAGAAAACTAGTCCTCTCATGAGAAGACAGACCTGACAT
CTACTGAAAAATAGACTTTACTGGAAAAAATATGTGTATGAATACCTTCTAGTTTTTGTGAACGTTCTCA
AGATGGATAAAAGCTTTTCCTTGTAAAACGAGACTGATCAGATAGTCATCAAGAAGATTGTTAAAGAAAA
TTTTCCAAGGTTCGGAGTGCCAAAAGCAATAGTGTCAGATAATGGTCCTGCCTTTGTTGCCCAGGTAAGT
CAGGGTGTGGCCAAGTATTTAGAGGTCAAATGAAAATTCCATTGTGTGTACAGACCTCAGAGCTCAGGAA
AGATAAAAAGAATAAATAAAACTCTAAACAGACCTTGACAAAATTAATCCTAGAGACTGGCACAGACTT
ACTTGGTACTCCTTCCCCTTGCCCTATTTAGAACTGAGAATACTCCCTCTTGATTCGGTTTTACTCTTTT
```

Fig. 5C

```
TAAGATCCTTTATGGGGCTCCTATGCCATCACTGTCTTAAATGATGTGTTTAAACCTATGTTGTTATAAT
AATGATCTATATGTTAAGTTAAAAGGCTTGCAGGTGGTGCAGAAAGAAGTCTGGTCACAACTGGCTACAG
TGAACAAGCTGGGTACCCCAAGGACATCTTACCAGTTCCAGCCAGAGATCTGATCTACGATCCCCGGGTC
GACCCGGGTCGACCCTGTGGAATGTGTGTCAGTTAGGGTGTGGAAAGTCCCCAGGCTCCCCAGCAGGCAG
AAGTATGCAAAGCATGCATCTCAATTAGTCAGCAACCAGGTGTGGAAAGTCCCCAGGCTCCCCAGCAGGC
AGAAGTATGCAAAGCATGCATCTCAATTAGTCAGCAACCATAGTCCCGCCCCTAACTCCGCCCATCCCGC
CCCTAACTCCGCCCAGTTCCGCCCATTCTCCGCCCCATGGCTGACTAATTTTTTTATTTATGCAGAGGC
CGAGGCCGCCTCGGCCTCTGAGCTATTCCAGAAGTAGTGAGGAGGCTTTTTTGGAGGCCTAGGCTTTTGC
AAAAAGCTTCACGCTGCCGCAAGCACTCAGGGCGCAAGGGCTGCTAAAGGAAGCGGAACACGTAGAAAGC
CAGTCCGCAGAAACGGTGCTGACCCCGGATGAATGTCAGCTACTGGGCTATCTGGACAAGGGAAAACGCA
AGCGCAAAGAGAAAGCAGGTAGCTTGCAGTGGGCTTACATGGCGATAGCTAGACTGGGCGGTTTTATGGA
CAGCAAGCGAACCGGAATTGCCAGCTGGGGCGCCCTCTGGTAAGGTTGGGAAGCCCTGCAAAGTAAACTG
GATGGCTTTCTTGCCGCCAAGGATCTGATGGCGCAGGGGATCAAGATCTGATCAAGAGACAGGATGAGGA
TCGTTTCGCATGATTGAACAAGATGGATTGCACGCAGGTTCTCCGGCCGCTTGGGTGGAGAGGCTATTCG
GCTATGACTGGGCACAACAGACAATCGGCTGCTCTGATGCCGCCGTGTTCCGGCTGTCAGCGCAGGGGCG
CCCGGTTCTTTTTGTCAAGACCGACCTGTCCGGTGCCCTGAATGAACTGCAGGACGAGGCAGCGCGGCTA
TCGTGGCTGGCCACGACGGGCGTTCCTTGCGCAGCTGTGCTCGACGTTGTCACTGAAGCGGGAAGGGACT
GGCTGCTATTGGGCGAAGTGCCGGGGCAGGATCTCCTGTCATCTCACCTTGCTCCTGCCGAGAAAGTATC
CATCATGGCTGATGCAATGCGGCGGCTGCATACGCTTGATCCGGCTACCTGCCCATTCGACCACCAAGCG
AAACATCGCATCGAGCGAGCACGTACTCGGATGGAAGCCGGTCTTGTCGATCAGGATGATCTGGACGAAG
AGCATCAGGGGCTCGCGCCAGCCGAACTGTTCGCCAGGCTCAAGGCGCGCATGCCCGACGGCGAGGATCT
CGTCGTGACCCATGGCGATGCCTGCTTGCCGAATATCATGGTGGAAAATGGCCGCTTTTCTGGATTCATC
GACTGTGGCCGGCTGGGTGTGGCGGACCGCTATCAGGACATAGCGTTGGCTACCCGTGATATTGCTGAAG
AGCTTGGCGGCGAATGGGCTGACCGCTTCCTCGTGCTTTACGGTATCGCCGCTCCCGATTCGCAGCGCAT
CGCCTTCTATCGCCTTCTTGACGAGTTCTTCTGAGCGGGACTCTGGGGTTCGAAATGACCGACCAAGCGA
CGCCCAACCTGCCATCACGAGATTTCGATTCCACCGCCGCCTTCTATGAAAGGTTGGGCTTCGGAATCGT
TTTCCGGGACGGAATTCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACATACCTCGCTC
TGCTAATCCTGTTACCAGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACAGCCCAGCTTGGAGCGA
ACGACCTACACCGAACTGAGATACCTACAGCGTGAGCATTGAGAAAGCGCCACGCTTCCCGAAGGGAGAA
AGGCGGACAGGTATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTGTGATGCTCG
TCAGGGGGCGGAGCCTATGGAAAAACGCCAGCAACGCCGAGATGCGCCGCCTCGAGAACCCTGGCCCTA
TTATTGGGTGGACTAACCATGGGGGAATTGCCGCTGGAATAGGAACAGGGACTACTGCTCTAATGGCCA
CTCAGCAATTCCAGCAGCTCCAAGCCGCAGTACAGGATGATCTCAGGGAGGTTGAAAAATCAATCTCTAA
CCTAGAAAGTCTCTCACTTCCCTGTCTGAAGTTGTCCTACAGAATCGAAGGGCCTAGACTTGTTATTT
CTAAAAGAAGGAGGGCTGTGTGCTGCTCTAAAAGAAGAATGTTGCTTCTATGCGGACCACACAGGACTAG
TGAGAGACAGCATGGCCAAATTGAGAGAGAGGCTTAATCAGAGACAGAAACTGTTTGAGTCAACTCAAGG
ATGGTTTGAGGGACTGTTTAACAGATCCCCTTGGTTTACCACCTTGATATCTACCATTATGGGACCCCTC
ATTGTACTCCTAATGATTTTGCTCTTCGGACCCTGCATTCTTAATCGATTAGTCCAATTTGTTAAAGACA
GGATATCAGTGGTCCAGGCTCTAGTTTTGACTCAACAATATCACCAGCTGAAGCCTATAGAGTACGAGCC
ATAGATAAAATAAAAGATTTTATTTAGTCTCCAGAAAAAGGGGGG
```

Fig. 6A

PVLMB2

AATGAAAGACCCCACCTGTAGGTTTGGCAAGCTAGCTTAAGTAACGCCATTTTGCAAGGCATGGAAAAATA
CATAACTGAGAATAGAGAAGTTCAGATCAAGGTCAGGAACAGATGGAACAGCTGAATATGGGCCAAACAGG
ATATCTGTGGTAAGCAGTTCCTGCCCCGGCTCAGGGCCAAGAACAGATGGAACAGCTGAATATGGGCCAAA
CAGGATATCTGTGGTAAGCAGTTCCTGCCCCGGCTCAGGGCCAAGAACAGATGGTCCCCAGATGCGGTCCA
GCCCTCAGCAGTTTCTAGAGAACCATCAGATGTTTCCAGGGTGCCCCAAGGACCTGAAATGACCCTGTGCC
TTATTTGAACTAACCAATCAGTTCGCTTCTCGCTTCTGTTCGCGCGCTTCTGCTCCCCGAGCTCAATAAAA
GAGCCCACAACCCCTCACTCGGGGCGCCAGTCCTCCGATTGACTGAGTCGCCCGGGTACCCGTGTATCCAA
TAAACCCTCTTGCAGTTGCATCCGACTTGTGGTCTCGCTGTTCCTTGGGAGGGTCTCCTCTGAGTGATTGA
CTACCCGTCAGCGGGGGTCTTTCATTTGGGGGCTCGTCCGGGATCGGGAGACCCCTGCCCAGGGACCACCG
ACCCACCACCGGGAGGTAAGCTGGCCAGCAACTTATCTGTGTCTGTCCGATTGTCTAGTGTCTATGACTGA
TTTTATGCGCCTGCGTCGGTACTAGTTAGCTAACTAGCTCTGTATCTGGCGGACCCGTGGTGGAACTGACG
AGTTCGGAACACCCGGCCGCAACCCTGGGAGACGTCCCAGGAGGAACAGGGGAGGATCAGGGACGCCTGGT
GGACCCCTTTGAAGGCCAAGAGACCATTTGGGGTTGCGAGATCGTGGGTTCGAGTCCCACCTCGTGCCCAG
TTGCGAGATCGTGGGTTCGAGTCCCACCTCGTGTTTTGTTGCGAGATCGTGGGTTCGAGTCCCACCTCGCG
TCTGGTCACGGGATCGTGGGTTCGAGTCCCACCTCGTGTTTTGTTGCGAGATCGTGGGTTCGAGTCCCACC
TCGCGTCTGGTCACGGGATCGTGGGTTCGAGTCCCACCTCGTGCAGAGGGTCTCAATTGGCCGGCCTTAGA
GAGGCCATCTGATTCTTCTGGTTTCTCTTTTTGTCTTAGTCTCGTGTCCGCTCTTGTTGTGACTACTGTTT
TTCTAAAAATGGGACAATCTGTGTCCACTCCCCTTTCTCTGACTCTGGTTCTGTCGCTTGGTAATTTTGTT
TGTTTACGTTTGTTTTTGTGAGTCGTCTATGTTGTCTGTTACTATCTTGTTTTTGTTTGTGGTTTACGGTT
TCTGTGTGTGTCTTGTGTGTCTCTTTGTGTTCAGACTTGGACTGATGACTGACGACTGTTTTAAGTTATG
CCTTCTAAAATAAGCCTAAAAATCCTGTCAGATCCCTATGCTGACCACTTCCTTTCAGATCAACAGCTGCC
CTTACGTATCGATGGATCCCTCGACTAACTAATAGCCCATTCTCCAAGGTCGAGCGGGATCAATTCCGCCC
CCCCCCTAACGTTACTGGCCGAAGCCGCTTGGAATAAGGCCGGTGTGCGTTTGTCTATATGTTATTTTCCA
CCATATTGCCGTCTTTTGGCAATGTGAGGGCCCGGAAACCTGGCCCTGTCTTCTTGACGAGCATTCCTAGG
GGTCTTTCCCCTCTCGCCAAAGGAATGCAAGGTCTGTTAATGTCGTGAAGGAAGCAGTTCCTCTGGAAGC
TTCTTGAAGACAAACAACGTCTGTAGCGACCCTTTGCAGGCAGCGGAACCCCCCACCTGGCGACAGGTGCC
TCTGCGGCCAAAAGCCACGTGTATAAGATACACCTGCAAAGGCGGCACAACCCCAGTGCCACGTTGTGAGT
TGGATAGTTGTGGAAAGAGTCAAATGGCTCTCCTCAAGCGTATTCAACAAGGGGCTGAAGGATGCCCAGAA
GGTACCCCATTGTATGGGATCTGATCTGGGGCCTCGGTGCACATGCTTTACATGTGTTTAGTCGAGGTTAA
AAAAACGTCTAGGCCCCCGAACCACGGGGACGTGGTTTTCCTTTGAAAAACACGATAATAATCATGGGCG
CGGATCCCGTCGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAACAGTTGCGCAG
CCTGAATGGCGAATGGCGCTTTGCCTGGTTTCCGGCACCAGAAGCGGTGCCGGAAAGCTGGCTGGAGTGCG
ATCTTCCTGAGGCCGATACTGTCGTCGTCCCCTCAAACTGGCAGATGCACGGTTACGATGCGCCCATCTAC
ACCAACGTAACCTATCCCATTACGGTCAATCCGCCGTTTGTTCCCACGGAGAATCCGACGGGTTGTTACTC
GCTCACATTTAATGTTGATGAAAGCTGGCTACAGGAAGGCCAGACGCGAATTATTTTTGATGGCGTTAACT
CGGCGTTTCATCTGTGGTGCAACGGGCGCTGGGTCGGTTACGGCCAGGACAGTCGTTTGCCGTCTGAATTT
GACCTGAGCGCATTTTTACGCGCCGGAGAAAACCGCCTCGCGGTGATGGTGCTGCGTTGGAGTGACGGCAG
TTATCTGGAAGATCAGGATATGTGGCGGATGAGCGGCATTTTCCGTGACGTCTCGTTGCTGCATAAACCGA
CTACACAAATCAGCGATTTCCATGTTGCCACTCGCTTTAATGATGATTTCAGCCGCGCTGTACTGGAGGCT
GAAGTTCAGATGTGCGGCGAGTTGCGTGACTACCTACGGGTAACAGTTTCTTTATGGCAGGGTGAAACGCA
GGTCGCCAGCGGCACCGCGCCTTTCGGCGGTGAAATTATCGATGAGCGTGGTGGTTATGCCGATCGCGTCA

Fig. 6B

```
CACTACGTCTGAACGTCGAAAACCCGAAACTGTGGAGCGCCGAAATCCCGAATCTCTATCGTGCGGTGGTT
GAACTGCACACCGCCGACGGCACGCTGATTGAAGCAGAAGCCTGCGATGTCGGTTTCCGCGAGGTGCGGAT
TGAAAATGGTCTGCTGCTGCTGAACGGCAAGCCGTTGCTGATTCGAGGCGTTAACCGTCACGAGCATCATC
CTCTGCATGGTCAGGTCATGGATGAGCAGACGATGGTGCAGGATATCCTGCTGATGAAGCAGAACAACTTT
AACGCCGTGCGCTGTTCGCATTATCCGAACCATCCGCTGTGGTACACGCTGTGCGACCGCTACGGCCTGTA
TGTGGTGGATGAAGCCAATATTGAAACCCACGGCATGGTGCCAATGAATCGTCTGACCGATGATCCGCGCT
GGCTACCGGCGATGAGCGAACGCGTAACGCGAATGGTGCAGCGCGATCGTAATCACCCGAGTGTGATCATC
TGGTCGCTGGGGAATGAATCAGGCCACGGCGCTAATCACGACGCGCTGTATCGCTGGATCAAATCTGTCGA
TCCTTCCCGCCCGGTGCAGTATGAAGGCGGCGGAGCCGACACCACGGCCACCGATATTATTTGCCCGATGT
ACGCGCGCGTGGATGAAGACCAGCCCTTCCCGGCTGTGCCGAAATGGTCCATCAAAAAATGGCTTTCGCTA
CCTGGAGAGACGCGCCCGCTGATCCTTTGCGAATACGCCCACGCGATGGGTAACAGTCTTGGCGGTTTCGC
TAAATACTGGCAGGCGTTTCGTCAGTATCCCCGTTTACAGGGCGGCTTCGTCTGGGACTGGGTGGATCAGT
CGCTGATTAAATATGATGAAAACGGCAACCCGTGGTCGGCTTACGGCGGTGATTTTGGCGATACGCCGAAC
GATCGCCAGTTCTGTATGAACGGTCTGGTCTTTGCCGACCGCACGCCGCATCCAGCGCTGACGGAAGCAAA
ACACCAGCAGCAGTTTTTCCAGTTCCGTTTATCCGGGCAAACCATCGAAGTGACCAGCGAATACCTGTTCC
GTCATAGCGATAACGAGCTCCTGCACTGGATGGTGGCGCTGGATGGTAAGCCGCTGGCAAGCGGTGAAGTG
CCTCTGGATGTCGCTCCACAAGGTAAACAGTTGATTGAACTGCCTGAACTACCGCAGCCGGAGAGCGCCGG
GCAACTCTGGCTCACAGTACGCGTAGTGCAACCGAACGCGACCGCATGGTCAGAAGCCGGGCACATCAGCG
CCTGGCAGCAGTGGCGTCTGGCGGAAAACCTCAGTGTGACGCTCCCCGCCGCGTCCCACGCCATCCCGCAT
CTGACCACCAGCGAAATGGATTTTTGCATCGAGCTGGGTAATAAGCGTTGGCAATTTAACCGCCAGTCAGG
CTTTCTTTCACAGATGTGGATTGGCGATAAAAAACAACTGCTGACGCCGCTGCGCGATCAGTTCACCCGTG
CACCGCTGGATAACGACATTGGCGTAAGTGAAGCGACCCGCATTGACCCTAACGCCTGGGTCGAACGCTGG
AAGGCGGCGGGCCATTACCAGGCCGAAGCAGCGTTGTTGCAGTGCACGGCAGATACACTTGCTGATGCGGT
GCTGATTACGACCGCTCACGCGTGGCAGCATCAGGGGAAAACCTTATTTATCAGCCGGAAAACCTACCGGA
TTGATGGTAGTGGTCAAATGGCGATTACCGTTGATGTTGAAGTGGCGAGCGATACACCGCATCCGGCGCGG
ATTGGCCTGAACTGCCAGCTGGCGCAGGTAGCAGAGCGGGTAAACTGGCTCGGATTAGGGCCGCAAGAAAA
CTATCCCGACCGCCTTACTGCCGCCTGTTTTGACCGCTGGGATCTGCCATTGTCAGACATGTATACCCCGT
ACGTCTTCCCGAGCGAAAACGGTCTGCGCTGCGGGACGCGCGAATTGAATTATGGCCCACACCAGTGGCGC
GGCGACTTCCAGTTCAACATCAGCCGCTACAGTCAACAGCAACTGATGGAAACCAGCCATCGCCATCTGCT
GCACGCGGAAGAAGGCACATGGCTGAATATCGACGGTTTCCATATGGGGATTGGTGGCGACGACTCCTGGA
GCCCGTCAGTATCGGCGGAATTCCAGCTGAGCGCCGGTCGCTACCATTACCAGTTGGTCTGGTGTCAAAAA
TAATAATAACCGGGCAGGGGGATCCGAAGGCGGGACAGCAGTGCAGTGGTGGACAGAAAGCAAGTGATC
TAGGCCAGCAGCCTCCCTAAAGGGACTTCAGCCCACAAAGCCAAACTTGTGGCTTTAATACAAGCTCTGTA
AATGGTAAAAAAAAAAAAGTCTACACGGACAGCAGGTATGCTCTTGCCACTGTACAGAGCAATATACAGAC
AAAGAGAACTGTTGACATCTGCAGAGAAAGACCTAAGATGCTGTGGCTAAAAGAAATCAGATGGCAAATCT
AACCGCCCAGGCATCCTAAAGAGCAATGATCCTGACAGTCTGAAGACTATCAAGTTATAGACAAATTAAGA
CTGGTAAAAAAACCCTGTATAAAATAGTAAAACTGAAAAAGAAAACTAGTCCTCTCATGAGAAGACAG
ACCTGACATCTACTGAAAAATAGACTTTACTGGAAAAAATATGTGTATGAATACCTTCTAGTTTTTGTGAA
CGTTCTCAAGATGGATAAAAGCTTTTCCTTGTAAAACGAGACTGATCAGATAGTCATCAAGAAGATTGTTA
AAGAAAATTTTCCAAGGTTCGGAGTGCCAAAAGCAATAGTGTCAGATAATGGTCCTGCCTTTGTTGCCCAG
GTAAGTCAGGGTGTGGCCAAGTATTTAGAGGTCAAATGAAAATTCCATTGTGTGTACAGACCTCAGAGCTC
AGGAAAGATAAAAAGAATAAATAAAACTCTAAACAGACCTTGACAAAATTAATCCTAGAGACTGGCACAG
ACTTACTTGGTACTCCTTCCCCTTGCCCTATTTAGAACTGAGAATACTCCCTCTTGATTCGGTTTTACTCT
TTTTAAGATCCTTTATGGGGCTCCTATGCCATCACTGTCTTAAATGATGTGTTTAAACCTATGTTGTTATA
```

Fig. 6C

```
ATAATGATCTATATGTTAAGTTAAAAGGCTTGCAGGTGGTGCAGAAAGAAGTCTGGTCACAACTGGCTACA
GTGAACAAGCTGGGTACCCCAAGGACATCTTACCAGTTCCAGCCAGAGATCTGATCTACGATCCCCGGGTC
GACCCGGGTCGACCCTGTGGAATGTGTGTCAGTTAGGGTGTGGAAAGTCCCCAGGCTCCCCAGCAGGCAGA
AGTATGCAAAGCATGCATCTCAATTAGTCAGCAACCAGGTGTGGAAAGTCCCCAGGCTCCCCAGCAGGCAG
AAGTATGCAAAGCATGCATCTCAATTAGTCAGCAACCATAGTCCCGCCCCTAACTCCGCCCATCCCGCCCC
TAACTCCGCCCAGTTCCGCCCATTCTCCGCCCCATGGCTGACTAATTTTTTTATTTATGCAGAGGCCGAG
GCCGCCTCGGCCTCTGAGCTATTCCAGAAGTAGTGAGGAGGCTTTTTTGGAGGCCTAGGCTTTTGCAAAAA
GCTTCACGCTGCCGCAAGCACTCAGGGCGCAAGGGCTGCTAAAGGAAGCGGAACACGTAGAAAGCCAGTCC
GCAGAAACGGTGCTGACCCCGGATGAATGTCAGCTACTGGGCTATCTGGACAAGGGAAAACGCAAGCGCAA
AGAGAAAGCAGGTAGCTTGCAGTGGGCTTACATGGCGATAGCTAGACTGGGCGGTTTTATGGACAGCAAGC
GAACCGGAATTGCCAGCTGGGGCGCCCTCTGGTAAGGTTGGGAAGCCCTGCAAAGTAAACTGGATGGCTTT
CTTGCCGCCAAGGATCTGATGGCGCAGGGGATCAAGATCTGATCAAGAGACAGGATGAGGATCGTTTCGCA
TGATTGAACAAGATGGATTGCACGCAGGTTCTCCGGCCGCTTGGGTGGAGAGGCTATTCGGCTATGACTGG
GCACAACAGACAATCGGCTGCTCTGATGCCGCCGTGTTCCGGCTGTCAGCGCAGGGGCGCCCGGTTCTTTT
TGTCAAGACCGACCTGTCCGGTGCCCTGAATGAACTGCAGGACGAGGCAGCGCGGCTATCGTGGCTGGCCA
CGACGGGCGTTCCTTGCGCAGCTGTGCTCGACGTTGTCACTGAAGCGGGAAGGGACTGGCTGCTATTGGGC
GAAGTGCCGGGGCAGGATCTCCTGTCATCTCACCTTGCTCCTGCCGAGAAAGTATCCATCATGGCTGATGC
AATGCGGCGGCTGCATACGCTTGATCCGGCTACCTGCCCATTCGACCACCAAGCGAAACATCGCATCGAGC
GAGCACGTACTCGGATGGAAGCCGGTCTTGTCGATCAGGATGATCTGGACGAAGAGCATCAGGGGCTCGCG
CCAGCCGAACTGTTCGCCAGGCTCAAGGCGCGCATGCCCGACGGCGAGGATCTCGTCGTGACCCATGGCGA
TGCCTGCTTGCCGAATATCATGGTGGAAAATGGCCGCTTTTCTGGATTCATCGACTGTGGCCGGCTGGGTG
TGGCGGACCGCTATCAGGACATAGCGTTGGCTACCCGTGATATTGCTGAAGAGCTTGGCGGCGAATGGGCT
GACCGCTTCCTCGTGCTTTACGGTATCGCCGCTCCCGATTCGCAGCGCATCGCCTTCTATCGCCTTCTTGA
CGAGTTCTTCTGAGCGGGACTCTGGGGTTCGAAATGACCGACCAAGCGACGCCCAACCTGCCATCACGAGA
TTTCGATTCCACCGCCGCCTTCTATGAAAGGTTGGGCTTCGGAATCGTTTTCCGGGACGGAATTCGTAATC
TGCTGCTTGCAAACAAAAAAACCACCGCTACCAGCGGTGGTTTGTTTGCCGGATCAAGAGCTACCAACTCT
TTTTCCGAAGGTAACTGGCTTCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAGGCGCAGCGGTC
GGGCTGAACGGGGGGTTCGTGCACACAGCCCAGCTTGGAGCGAACGACCTACACCGAACTGAGATACCTAC
AGCGTGAGCATTGAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGTCCTGTCGGGTT
TCGCCACCTCTGACTTGAGCGTCGATTTTTGTGATGCTCGTCAGGGGGCGGAGCCTATGGAAAAACGCCA
GCAACGCCGAGATGCGCCGCCTCGAGAACCCTGGCCCTATTATTGGGTGGACTAACCATGGGGGAATTGC
CGCTGGAATAGGAACAGGGACTACTGCTCTAATGGCCACTCAGCAATTCCAGCAGCTCCAAGCCGCAGTAC
AGGATGATCTCAGGGAGGTTGAAAAATCAATCTCTAACCTAGAAAAGTCTCTCACTTCCCTGTCTGAAGTT
GTCCTACAGAATCGAAGGGGCCTAGACTTGTTATTTCTAAAAGAAGGAGGGCTGTGTGCTGCTCTAAAAGA
AGAATGTTGCTTCTATGCGGACCACACAGGACTAGTGAGAGACAGCATGGCCAAATTGAGAGAGAGGCTTA
ATCAGAGACAGAAACTGTTTGAGTCAACTCAAGGATGGTTTGAGGGACTGTTTAACAGATCCCCTTGGTTT
ACCACCTTGATATCTACCATTATGGGACCCCTCATTGTACTCCTAATGATTTTGCTCTTCGGACCCTGCAT
TCTTAATCGATTAGTCCAATTTGTTAAAGACAGGATATCAGTGGTCCAGGCTCTAGTTTTGACTCAACAAT
ATCACCAGCTGAAGCCTATAGAGTACGAGCCATAGATAAAATAAAAGATTTTATTTAGTCTCCAGAAAAAG
GGGGG
```

Fig. 7A

PVLMB3

AATGAAAGACCCCACCTGTAGGTTTGGCAAGCTAGCTTAAGTAACGCCATTTTGCAAGGCATGGAAAAA
TACATAACTGAGAATAGAGAAGTTCAGATCAAGGTCAGGAACAGATGGAACAGCTGAATATGGGCCAAA
CAGGATATCTGTGGTAAGCAGTTCCTGCCCCGGCTCAGGGCCAAGAACAGATGGAACAGCTGAATATGG
GCCAAACAGGATATCTGTGGTAAGCAGTTCCTGCCCCGGCTCAGGGCCAAGAACAGATGGTCCCCAGAT
GCGGTCCAGCCCTCAGCAGTTTCTAGAGAACCATCAGATGTTTCCAGGGTGCCCCAAGGACCTGAAATG
ACCCTGTGCCTTATTTGAACTAACCAATCAGTTCGCTTCTCGCTTCTGTTCGCGCGCTTCTGCTCCCCG
AGCTCAATAAAAGAGCCCACAACCCCTCACTCGGGGCGCCAGTCCTCCGATTGACTGAGTCGCCCGGGT
ACCCGTGTATCCAATAAACCCTCTTGCAGTTGCATCCGACTTGTGGTCTCGCTGTTCCTTGGGAGGGTC
TCCTCTGAGTGATTGACTACCCGTCAGCGGGGTCTTTCATTTGGGGCTCGTCCGGGATCGGAGACC
CCTGCCCAGGGACCACCGACCCACCACCGGGAGATAAGCTGGGTCGGAGACCCCTGCCCAGGGACCACC
GACCCACCACCGGGAGGTAAGCTGGCCAGCAACTTATCTGTGTCTGTCCGATTGTCTAGTGTCTATGAC
TGATTTTATGCGCCTGCGTCGGTACTAGTTAGCTAACTAGCTCTGTATCTGGCGGACCCGTGGTGGAAC
TGACGAGTTCGGAACACCCGGCCGCAACCCTGGGAGACGTCCCAGGAGGAACAGGGGAGGATCAGGGAC
GCCTGGTGGACCCCTTTGAAGGCCAAGAGACCATTTGGGGTTGCGAGATCGTGGGTTCGAGTCCCACCA
TCGATGGTTACGTATCGATGGATCCCTCGACTAACTAATAGCCCATTCTCCAAGGTCGAGCGGGATCAA
TTCCGCCCCCCCCTAACGTTACTGGCCGAAGCCGCTTGGAATAAGGCCGGTGTGCGTTTGTCTATATG
TTATTTTCCACCATATTGCCGTCTTTTGGCAATGTGAGGGCCCGGAAACCTGGCCCTGTCTTCTTGACG
AGCATTCCTAGGGTCTTTCCCCTCTCGCCAAAGGAATGCAAGGTCTGTTGAATGTCGTGAAGGAAGCA
GTTCCTCTGGAAGCTTCTTGAAGACAAACAACGTCTGTAGCGACCCTTTGCAGGCAGCGGAACCCCCA
CCTGGCGACAGGTGCCTCTGCGGCCAAAAGCCACGTGTATAAGATACACCTGCAAAGGCGGCACAACCC
CAGTGCCACGTTGTGAGTTGGATAGTTGTGGAAAGAGTCAAATGGCTCTCCTCAAGCGTATTCAACAAG
GGGCTGAAGGATGCCCAGAAGGTACCCCATTGTATGGGATCTGATCTGGGGCCTCGGTGCACATGCTTT
ACATGTGTTTAGTCGAGGTTAAAAAAACGTCTAGGCCCCCGAACCACGGGGACGTGGTTTTCCTTTGA
AAAACACGATAATAATCATGGGCGCGGATCCCGTCGTTTTACAACGTCGTGACTGGGAAAACCCTGGCG
TTACCCAACTTAATCGCCTTGCAGCACATCCCCCTTTCGCCAGCTGGCGTAATAGCGAAGAGGCCCGCA
CCGATCGCCCTTCCCAACAGTTGCGCAGCCTGAATGGCGAATGGCGCTTTGCCTGGTTTCCGGCACCAG
AAGCGGTGCCGGAAAGCTGGCTGGAGTGCGATCTTCCTGAGGCCGATACTGTCGTCGTCCCCTCAAACT
GGCAGATGCACGGTTACGATGCGCCCATCTACACCAACGTAACCTATCCCATTACGGTCAATCCGCCGT
TTGTTCCCACGGAGAATCCGACGGGTTGTTACTCGCTCACATTTAATGTTGATGAAAGCTGGCTACAGG
AAGGCCAGACGCGAATTATTTTTGATGGCGTTAACTCGGCGTTTCATCTGTGGTGCAACGGGCGCTGGG
TCGGTTACGGCCAGGACAGTCGTTTGCCGTCTGAATTTGACCTGAGCGCATTTTTACGCGCCGGAGAAA
ACCGCCTCGCGGTGATGGTGCTGCGTTGGAGTGACGGCAGTTATCTGGAAGATCAGGATATGTGGCGGA
TGAGCGGCATTTTCCGTGACGTCTCGTTGCTGCATAAACCGACTACACAAATCAGCGATTTCCATGTTG
CCACTCGCTTTAATGATGATTTCAGCCGCGCTGTACTGGAGGCTGAAGTTCAGATGTGCGGCGAGTTGC
GTGACTACCTACGGGTAACAGTTTCTTTATGGCAGGGTGAAACGCAGGTCGCCAGCGGCACCGCGCCTT
TCGGCGGTGAAATTATCGATGAGCGTGGTGGTTATGCCGATCGCGTCACACTACGTCTGAACGTCGAAA
ACCCGAAACTGTGGAGCGCCGAAATCCCGAATCTCTATCGTGCGGTGGTTGAACTGCACACCGCCGACG
GCACGCTGATTGAAGCAGAAGCCTGCGATGTCGGTTTCCGCGAGGTGCGGATTGAAAATGGTCTGCTGC
TGCTGAACGGCAAGCCGTTGCTGATTCGAGGCGTTAACCGTCACGAGCATCATCCTCTGCATGGTCAGG
TCATGGATGAGCAGACGATGGTGCAGGATATCCTGCTGATGAAGCAGAACAACTTTAACGCCGTGCGCT
GTTCGCATTATCCGAACCATCCGCTGTGGTACACGCTGTGCGACCGCTACGGCCTGTATGTGGTGGATG

Fig. 7B

```
AAGCCAATATTGAAACCCACGGCATGGTGCCAATGAATCGTCTGACCGATGATCCGCGCTGGCTACCGG
CGATGAGCGAACGCGTAACGCGAATGGTGCAGCGCGATCGTAATCACCCGAGTGTGATCATCTGGTCGC
TGGGGAATGAATCAGGCCACGGCGCTAATCACGACGCGCTGTATCGCTGGATCAAATCTGTCGATCCTT
CCCGCCCGGTGCAGTATGAAGGCGGCGGAGCCGACACCACGGCCACCGATATTATTTGCCCGATGTACG
CGCGCGTGGATGAAGACCAGCCCTTCCCGGCTGTGCCGAAATGGTCCATCAAAAAATGGCTTTCGCTAC
CTGGAGAGACGCGCCCGCTGATCCTTTGCGAATACGCCCACGCGATGGGTAACAGTCTTGGCGGTTTCG
CTAAATACTGGCAGGCGTTTCGTCAGTATCCCCGTTTACAGGGCGGCTTCGTCTGGGACTGGGTGGATC
AGTCGCTGATTAAATATGATGAAAACGGCAACCCGTGGTCGGCTTACGGCGGTGATTTTGGCGATACGC
CGAACGATCGCCAGTTCTGTATGAACGGTCTGGTCTTTGCCGACCGCACGCCGCATCCAGCGCTGACGG
AAGCAAAACACCAGCAGCAGTTTTTCCAGTTCCGTTTATCCGGGCAAACCATCGAAGTGACCAGCGAAT
ACCTGTTCCGTCATAGCGATAACGAGCTCCTGCACTGGATGGTGGCGCTGGATGGTAAGCCGCTGGCAA
GCGGTGAAGTGCCTCTGGATGTCGCTCCACAAGGTAAACAGTTGATTGAACTGCCTGAACTACCGCAGC
CGGAGAGCGCCGGGCAACTCTGGCTCACAGTACGCGTAGTGCAACCGAACGCGACCGCATGGTCAGAAG
CCGGGCACATCAGCGCCTGGCAGCAGTGGCGTCTGGCGGAAAACCTCAGTGTGACGCTCCCCGCCGCGT
CCCACGCCATCCCGCATCTGACCACCAGCGAAATGGATTTTTGCATCGAGCTGGGTAATAAGCGTTGGC
AATTTAACCGCCAGTCAGGCTTTCTTTCACAGATGTGGATTGGCGATAAAAAACAACTGCTGACGCCGC
TGCGCGATCAGTTCACCCGTGCACCGCTGGATAACGACATTGGCGTAAGTGAAGCGACCCGCATTGACC
CTAACGCCTGGGTCGAACGCTGGAAGGCGGCGGGCCATTACCAGGCCGAAGCAGCGTTGTTGCAGTGCA
CGGCAGATACACTTGCTGATGCGGTGCTGATTACGACCGCTCACGCGTGGCAGCATCAGGGGAAAACCT
TATTTATCAGCCGGAAAACCTACCGGATTGATGGTAGTGGTCAAATGGCGATTACCGTTGATGTTGAAG
TGGCGAGCGATACACCGCATCCGGCGCGGATTGGCCTGAACTGCCAGCTGGCGCAGGTAGCAGAGCGGG
TAAACTGGCTCGGATTAGGGCCGCAAGAAAACTATCCCGACCGCCTTACTGCCGCCTGTTTTGACCGCT
GGGATCTGCCATTGTCAGACATGTATACCCCGTACGTCTTCCCGAGCGAAACGGTCTGCGCTGCGGGA
CGCGCGAATTGAATTATGGCCCACACCAGTGGCGCGGCGACTTCCAGTTCAACATCAGCCGCTACAGTC
AACAGCAACTGATGGAAACCAGCCATCGCCATCTGCTGCACGCGGAAGAAGGCACATGGCTGAATATCG
ACGGTTTCCATATGGGGATTGGTGGCGACGACTCCTGGAGCCCGTCAGTATCGGCGGAATTCCAGCTGA
GCGCCGGTCGCTACCATTACCAGTTGGTCTGGTGTCAAAAATAATAATAACCGGGCAGGGGGGATCCGA
AGGCGGGGACAGCAGTGCAGTGGTGGACAGAAAGCAAGTGATCTAGGCCAGCAGCCTCCCTAAAGGGAC
TTCAGCCCACAAAGCCAAACTTGTGGCTTTAATACAAGCTCTGTAAATGGTAAAAAAAAAAAAGTCTAC
ACGGACAGCAGGTATGCTCTTGCCACTGTACAGAGCAATATACAGACAAAGAGAACTGTTGACATCTGC
AGAGAAAGACCTAAGATGCTGTGGCTAAAAGAAATCAGATGGCAAATCTAACCGCCCAGGCATCCTAAA
GAGCAATGATCCTGACAGTCTGAAGACTATCAAGTTATAGACAAATTAAGACTGGTAAAAAAACCCTG
TATAAAATAGTAAAAACTGAAAAAGAAAACTAGTCCTCTCATGAGAAGACAGACCTGACATCTACTGA
AAAATAGACTTTACTGGAAAAAATATGTGTATGAATACCTTCTAGTTTTTGTGAACGTTCTCAAGATGG
ATAAAAGCTTTTCCTTGTAAAACGAGACTGATCAGATAGTCATCAAGAAGATTGTTAAAGAAAATTTTC
CAAGGTTCGGAGTGCCAAAAGCAATAGTGTCAGATAATGGTCCTGCCTTTGTTGCCCAGGTAAGTCAGG
GTGTGGCCAAGTATTTAGAGGTCAAATGAAAATTCCATTGTGTGTACAGACCTCAGAGCTCAGGAAAGA
TAAAAAGAATAAATAAAACTCTAAACAGACCTTGACAAAATTAATCCTAGAGACTGGCACAGACTTAC
TTGGTACTCCTTCCCCTTGCCCTATTTAGAACTGAGAATACTCCCTCTTGATTCGGTTTTACTCTTTTT
AAGATCCTTTATGGGGCTCCTATGCCATCACTGTCTTAAATGATGTGTTTAAACCTATGTTGTTATAAT
AATGATCTATATGTTAAGTTAAAAGGCTTGCAGGTGGTGCAGAAAGAAGTCTGGTCACAACTGGCTACA
GTGAACAAGCTGGGTACCCCAAGGACATCTTACCAGTTCCAGCCAGAGATCTGATCTACGATCCCCGGG
TCGACCCGGGTCGACCCTGTGGAATGTGTGTCAGTTAGGGTGTGGAAAGTCCCCAGGCTCCCCAGCAGG
```

Fig. 7C

```
CAGAAGTATGCAAAGCATGCATCTCAATTAGTCAGCAACCAGGTGTGGAAAGTCCCCAGGCTCCCCAGC
AGGCAGAAGTATGCAAAGCATGCATCTCAATTAGTCAGCAACCATAGTCCCGCCCCTAACTCCGCCCAT
CCCGCCCCTAACTCCGCCCAGTTCCGCCCATTCTCCGCCCCATGGCTGACTAATTTTTTTATTTATGC
AGAGGCCGAGGCCGCCTCGGCCTCTGAGCTATTCCAGAAGTAGTGAGGAGGCTTTTTTGGAGGCCTAGG
CTTTTGCAAAAAGCTTCACGCTGCCGCAAGCACTCAGGGCGCAAGGGCTGCTAAAGGAAGCGGAACACG
TAGAAAGCCAGTCCGCAGAAACGGTGCTGACCCCGGATGAATGTCAGCTACTGGGCTATCTGGACAAGG
GAAAACGCAAGCGCAAAGAGAAAGCAGGTAGCTTGCAGTGGGCTTACATGGCGATAGCTAGACTGGGCG
GTTTTATGGACAGCAAGCGAACCGGAATTGCCAGCTGGGGCGCCCTCTGGTAAGGTTGGGAAGCCCTGC
AAAGTAAACTGGATGGCTTTCTTGCCGCCAAGGATCTGATGGCGCAGGGGATCAAGATCTGATCAAGAG
ACAGGATGAGGATCGTTTCGCATGATTGAACAAGATGGATTGCACGCAGGTTCTCCGGCCGCTTGGGTG
GAGAGGCTATTCGGCTATGACTGGGCACAACAGACAATCGGCTGCTCTGATGCCGCCGTGTTCCGGCTG
TCAGCGCAGGGGCGCCCGGTTCTTTTTGTCAAGACCGACCTGTCCGGTGCCCTGAATGAACTGCAGGAC
GAGGCAGCGCGGCTATCGTGGCTGGCCACGACGGGCGTTCCTTGCGCAGCTGTGCTCGACGTTGTCACT
GAAGCGGGAAGGGACTGGCTGCTATTGGGCGAAGTGCCGGGGCAGGATCTCCTGTCATCTCACCTTGCT
CCTGCCGAGAAAGTATCCATCATGGCTGATGCAATGCGGCGGCTGCATACGCTTGATCCGGCTACCTGC
CCATTCGACCACCAAGCGAAACATCGCATCGAGCGAGCACGTACTCGGATGGAAGCCGGTCTTGTCGAT
CAGGATGATCTGGACGAAGAGCATCAGGGGCTCGCGCCAGCCGAACTGTTCGCCAGGCTCAAGGCGCGC
ATGCCCGACGGCGAGGATCTCGTCGTGACCCATGGCGATGCCTGCTTGCCGAATATCATGGTGGAAAAT
GGCCGCTTTTCTGGATTCATCGACTGTGGCCGGCTGGGTGTGGCGGACCGCTATCAGGACATAGCGTTG
GCTACCCGTGATATTGCTGAAGAGCTTGGCGGCGAATGGGCTGACCGCTTCCTCGTGCTTTACGGTATC
GCCGCTCCCGATTCGCAGCGCATCGCCTTCTATCGCCTTCTTGACGAGTTCTTCTGAGCGGGACTCTGG
GGTTCGAAATGACCGACCAAGCGACGCCCAACCTGCCATCACGAGATTTCGATTCCACCGCCGCCTTCT
ATGAAAGGTTGGGCTTCGGAATCGTTTTCCGGGACGGAATTCGTAATCTGCTGCTTGCAAACAAAAAAA
CCACCGCTACCAGCGGTGGTTTGTTTGCCGGATCAAGAGCTACCAACTCTTTTTCCGAAGGTAACTGGC
TTCAGCAGAGCGCAGATACCAAATACTGTCCTTCTAGTGTAGCCGTAGTTAGGCCACCACTTCAAGAAC
TCTGTAGCACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTGAACGGGG
GGTTCGTGCACACAGCCCAGCTTGGAGCGAACGACCTACACCGAACTGAGATACCTACAGCGTGAGCAT
TGAGAAAGCGCCACGCTTCCCGAAGGGAGAAAGGCGGACAGGTATCCGGTAAGCGGCAGGGTCGGAACA
GGAGAGCGCACGAGGGAGCTTCCAGGGGAAACGCCTGGTATCTTTATAGTCCTGTCGGGTTTCGCCAC
CTCTGACTTGAGCGTCGATTTTTGTGATGCTCGTCAGGGGGCGGAGCCTATGGAAAACGCCAGCAAC
GCCGAGATGCGCCGCCTCGAGAACCCTGGCCCTATTATTGGGTGGACTAACCATGGGGGAATTGCCGC
TGGAATAGGAACAGGGACTACTGCTCTAATGGCCACTCAGCAATTCCAGCAGCTCCAAGCCGCAGTACA
GGATGATCTCAGGGAGGTTGAAAAATCAATCTCTAACCTAGAAAAGTCTCTCACTTCCCTGTCTGAAGT
TGTCCTACAGAATCGAAGGGGCCTAGACTTGTTATTTCTAAAAGAAGGAGGGCTGTGTGCTGCTCTAAA
AGAAGAATGTTGCTTCTATGCGGACCACACAGGACTAGTGAGAGACAGCATGGCCAAATTGAGAGAGAG
GCTTAATCAGAGACAGAAACTGTTTGAGTCAACTCAAGGATGGTTTGAGGGACTGTTTAACAGATCCCC
TTGGTTTACCACCTTGATATCTACCATTATGGGACCCCTCATTGTACTCCTAATGATTTTGCTCTTCGG
ACCCTGCATTCTTAATCGATTAGTCCAATTTGTTAAAGACAGGATATCAGTGGTCCAGGCTCTAGTTTT
GACTCAACAATATCACCAGCTGAAGCCTATAGAGTACGAGCCATAGATAAATAAAGATTTTATTTAG
TCTCCAGAAAAGGGGGG
```

CHIMERIC VIRAL PACKAGING SIGNAL WITHOUT GAG GENE SEQUENCES

CROSS REFERENCE TO RELATED APPLICATIONS

The complete disclosure set forth in the U.S. provisional patent application entitled "Chimeric Packaging Signal Without gag Gene Sequences," Ser. No. 60/066,148, filed with the United States Patent and Trademark Office on Nov. 19, 1997, is incorporated herein. The applications are commonly owned.

STATEMENT OF GOVERNMENT RIGHTS

This invention was made with support under grants from National Institutes of Health (NIH) Grant No. 2R55 GM41314-08. The U.S. Government has certain rights in this invention.

BACKGROUND OF THE INVENTION

The employment of retrovirus derived vectors in biotechnological applications has been standard practice for many years. For example, early retrovirus-derived vectors are described in Wei et al., *J. Virol.*, 39:935–44 (1980) and Shimotohno et al., *Cell*, 26:67–77 (1981). Retroviruses are single-stranded RNA viruses. During an infection process in a host subject, such as a human, the RNA viruses are reverse transcribed into double stranded DNA. The double stranded DNA is subsequently integrated into the host cell DNA, and the virus becomes a permanent part of the host cell DNA. Once integrated, the virus is capable of expression of more viral RNA as well as the proteins that make up the virion. As retroviruses are usually not lytic, the retrovirus can continue to produce virus particles that bud from the surface of the cell.

Typically, modern retroviral vectoring systems consist of (1) RNA molecule(s) bearing cis-acting vector sequences needed for transcription, reverse-transcription, integration, translation and packaging of viral RNA into the viral particles, and (2) helper virus particles, budding from vector producer cells (VPCs), which express the trans-acting retroviral gene sequences (as proteins) needed for production of virus particles. By separating the cis- and trans-acting vector sequences completely, the virus is unable to maintain replication for more than one cycle of infection. The trans-acting vector sequences make empty virions (viral particles), whereas cis-acting vector sequences are capable of perpetuation or duration, only in the presence of the helper particles. Thus, cis-acting vector sequences and retroviral helper cells are the two essential components of modern retroviral vectoring systems.

Retrovirus-derived vectors (RVs) have been used in the majority of gene therapy clinical trials for a variety of reasons. For example, RVs can permanently integrate and express foreign genes, thus overcoming the problem of transient (short-term) expression, which is a significant problem of DNA transfection. Retroviruses, however, also suffer from several significant drawbacks. For example, retroviruses usually infect only dividing cells, and have a lower titer than some DNA viruses, such as adenovirus 5-derived vectors having titers of $>10^{11}$ transducing units/milliliter (TU)/ml. In addition, genetic recombination or "cross-over" can occur during replication (or at the DNA level), which can lead to outbreaks of replication competent retrovirus ("RCR"). RCRs occur as a result of regenerating the complete viral genome by genetic recombination. There are at least two different mechanisms by which this can occur. First, similar or identical overlapping nucleic acid sequences present on two separate DNA molecules (i.e., vector and helper sequences) can genetically recombine. Second, two separate RNA strands can serve as templates for cDNA synthesis during replication of the vector/virus, and genetic recombination can occur during DNA synthesis, leading to RCR. An additional confounding factor are the endogenous retroviral gene sequences that are present in the genome of the cells in which the virus is replicating. These retroviral gene sequences provide an additional source for generating RCR. Thus, it is important to separate the cis- and trans-acting sequences completely (i.e., no sequence overlap), and to provide a host cell genome that is devoid of closely related endogenous viral genes.

Unfortunately for most genetic therapies, RCR outbreaks have been detected in >15% of all lots of manufactured vectors tested prior to clinical trials. RCR are potentially lethal to primates and humans, and are therefore prohibited by the regulatory authorities. Significantly, the cost for detecting RCR can reach up to $100,000 per clinical batch. Often, however, RCR outbreaks often occur late in a vector production run as the VPCs are expanded. This suggests that a last minute outbreak might not be detected unless all of the clinical supernatant was tested. Thus, there is an 'uncertainty principle' that prevents complete assurance of catching the outbreak.

Still more unfortunately, many genetic therapy patients are immunecompromised (such as AIDS patients), and have reduced host defenses against oncogenic viruses, should an outbreak of RNA tumor virus occur. Clearly, this result presents many potential dangers. For example, an onco-retrovirus vector and the HIV retrovirus could infect the same cell. This mixed infection would most likely result in hybrid retrovirus particles containing both HIV-tropic and murine leukemia virus ("MLV")-tropic particles (ie., the hybrid particles can share their host ranges, enabling a broader scope of infection). Such mixed pseudotype infections have the expected, expanded cellullar tropism (Lusso et al., *Science*, 247:848–852 (1990)). MLV-tropisms include the so-called amphotropic (or 4070A strain) and gibbon ape leukemia virus (GALV)-tropic viruses, which are each capable of infecting a wide variety of human cells (as opposed to the primarily T-cell tropism of the native HIV-1 virus). Thus, a mixed virus infection could lead to HIV-1 infection of an expanded human cell repertoire, and possibly to a situation where the virus spreads like a common infection.

Of equal concern would be a genetic recombination event between MLV and HIV-1, wherein the HIV-1 envelope acquires a recombinant tropism, such as amphotropism or GALV-tropism. This could potentially provide a new HIV virus that could spread easily between humans, infecting most cells. It might be possible for only a small portion of the murine envelope glycoprotein gene to be present in order for this situation to occur (thus it might not disrupt other essential HIV-1 genes).

Therefore, a need exists for safe and efficient vectors for the transmission of genetic materials in a mammal. The genetic elements utilized in such vectors should be able to transmit genetic material that can be employed in gene therapy and cell therapy protocols as well as other biotechnological applications.

SUMMARY OF THE INVENTION

The present invention provides a chimeric viral packaging signal that can be employed in a vector for transmission of genetic material. The packaging signal contains an essential packaging nucleic acid sequence isolated from a mammalian type C retrovirus that is functionally joined to at least one non-essential packaging nucleic acid sequence that is isolated from a murine VL30 nucleic acid sequence. Additionally, the non-essential packaging nucleic acid sequence lacks a gag gene sequence.

Preferably, a murine leukemia virus is the mammalian type C retrovirus source for the essential packaging nucleic acid sequence. Additionally, the packaging signal can further contain at least one long terminal repeat nucleic acid sequence. The long terminal repeat nucleic acid sequence can be isolated from several possible sources, such as, a murine VL30 element, a retrovirus or a retrotransposon. Preferably, a packaging signal of the invention is employed in a retroviral vector.

The invention also provides a chimeric viral packaging signal that contains a long terminal repeat nucleic acid sequence isolated from a type C retrovirus or retrotransposon and operably linked to an essential packaging nucleic acid sequence. The essential packaging sequence is typically isolated from a mammalian type C leukemia virus and is operably linked to at least one non-essential packaging nucleic acid sequence. Preferably, the non-essential nucleic acid sequence is isolated from a murine VL30 nucleic acid sequence and lacks a gag gene sequence. Additionally, the prepared packaging signal is capable of packaging viral RNA or vector RNA into a retroviral capsid.

In one embodiment, the long terminal repeat nucleic acid sequence employed in a packaging signal of the invention is isolated from a murine retrovirus, a murine VL30 nucleic acid sequence, a retrotransposon, a simian retrovirus, an avian retrovirus, a feline retrovirus, a lentivirus, an avian retrovirus or a bovine retrovirus. The essential packaging nucleic acid sequence is isolated from a murine leukemia virus and contains at least a portion of SEQ ID NO: 22. Typically, the non-essential packaging nucleic acid sequence is isolated from a VL30 element that is obtained from either NVL-1, NVL-2, NVL-3, BVL-1, VL3, VM1, TLEV, VLSI, PB10, PA2, VL11, VLOV1 or VLOV2. Preferably, the non-essential packaging nucleic acid sequence contains at least a portion of SEQ ID NO: 23.

The invention also provides a packaging signal that contains an essential packaging nucleic acid sequence having a 52 basepair duplication between a minus strand primer binding site and a splice donor site. An exemplary vector containing this packaging signal is the vector, pVLMB1 (FIG. 5).

A. Definitions

A retrovirus is a single stranded, diploid RNA virus that replicates by means of reverse transcriptase and a retroviral virion. A retrovirus can be replication-competent or non-replication competent.

A retrotransposon (RTN) is a cellular mobile genetic element with long terminal repeats.

A VL30 is a virus-like, 30S RNA (retrotransposon) expressed in the cells of various vertebrate species. It is typified by LTRs, primer binding sites, and encapsidation signals. Although it does not contain intact viral genes, it is a viral parasite, or 'selfish DNA' that uses retroviral infections to be transmitted from cell to cell or from organism to organism. VL30s are usually found as integrated, 5 kb DNA sequences found in multiple copies within the cell genome. The 5 kb genomic DNA sequence consisting of LTRs and a stuffer fragment that can be replaced by foreign genes. VL30 vectors use cis-elements from the VL30 genome, or a synthetic equivalent.

An LTR is a long terminal repeat. LTRs are sequences found flanking i.e., positioned 5' and 3', retroviruses and retrotransposons such as VL30. The LTR sequence is typically at least several hundred bases long, bearing inverted repeats at its termini (often starting with TGAA . . . and ending with TTCA), and flanked with short direct repeats duplicated within the cell DNA sequences flanking the insertion site. The short inverted repeats are involved in integrating the full length viral, retrotransposon, or vector DNA into the host genome. The integration sequence is sometimes called att, for attachment. Inside the LTRs reside three distinct subregions: U3 (the enhancer and promoter region, transcribed from the 5'-LTR), R (repeated at both ends of the RNA), and U5 (transcribed from the 5'-LTR). The LTR and its associated flanking sequences (primer binding sites, splice sites, dimerization linkage and encapsidation sequences) comprise the cis-acting sequences of the retro-element or vector. Sources of LTR nucleic acid sequences, i.e., nucleic acid fragments or segments, include, but are not limited to murine retroviruses, murine VL30 sequences, retrotransposons, simian retroviruses, avian retroviruses, feline retroviruses, lentiviruses, avian retroviruses and bovine retroviruses.

A virion is a virus particle. In the case of retrovirus particles, the virion consists of an envelope with its characteristic envelope glycoprotein (capable of attaching to the recipient [target] cells) and a proteinaceous capsid, enclosing the viral or vector RNA together with its associated nucleocapsid protein. Also at the core of the virion is the RNA dimer, together with two copies of tRNA (primer) hydrogen-bonded to the viral or vector RNA. In addition to these virion-associated nucleic acid molecules, additional molecules of reverse transcriptase (an RNA directed DNA polymerase) catalyze replication, RNAse H [hybrid] activity, and integration [into cell DNA] via an integrase activity associated with the carboxyl terminus of the protein.

Murine leukemia virus (MLV) is a simple onco-retrovirus (a mammalian type C retrovirus), having three structural genes: gag (core particle), pol (reverse transcriptase), and env (envelope glycoprotein). These genes reside within the 10 kb backbone provirus, flanked by LTRs, primer binding sites, and a packaging signal.

Mammalian Type C retroviruses are viruses that are capable of infecting mammals and are a subgroup of the family retro viridae.

Retroviral helper cells are cultured cells engineered so as to produce retroviral virions, but not to package or transmit the RNA "helper" sequences which encode the viral proteins. Thus, a retroviral or retrotransposon vector (or a chimeric vector) can be transmitted by the helper cells.

Vector producer cells (VPCs): helper cells that are expressing vector particles.

Packaging signals (encapsidation signals or Ψ, for Packaging) contain both essential and non-essential nucleic acid sequences that are responsible for packaging (into virions) viral, retrotransposon, or vector derived RNA, and for transmission efficiency. Although this function is poorly understood, it is known to consist of multiple sites. One site is near to (or overlapping with) a canonical splice donor-like sequence near the (−)PBS. Another potentially important site is the dimerization linkage site (dl) which is responsible for the non-covalent joining of two copies of the RNA near the 5'-LTR. Yet another potentially important site is the packaging hairpin, or GACG loop. This sequence, together with several palindromic bases adjoining it, are highly conserved. Occasionally, an Aat2 restriction endonuclease site located asymmetrically within the loop is also conserved (as in the case of MLV and VL30). This serves as a site for artificially joining the MLV Ψ and the VL30 Ψ+ sequences. Yet another important sequence is the extended 3'-region known as Ψ+. In the case of MLV, this is the first approximate one-third of the retroviral gag gene sequence. In mouse VL30, it usually consists of some direct, overlapping repeats and other sequences 3' in direction from the Aat2 site. At least in lentiviruses, LTR sequences may also be involved in packaging, and in onco-retroviruses (such as ASLV), some packaging sequences may be located elsewhere in the genome. It is considered axiomatic that all sequences included in a retrovirus, retrotransposon or vector may also affect packaging through other mechanisms, such as size, protein binding affinity or secondary structure.

A gag gene sequence is a linear piece of DNA encoding at least one viral structural protein. FIG. 4 shows a particular gag gene sequence ( basepairs 621 to basepairs 2237).

An "essential packaging nucleic acid sequence", is a nucleic acid sequence isolated from a mammalian type C retrovirus. The essential packaging sequence contains a splice donor site, a dimerization sequence and a region of secondary structure, such as a stem loop structure. The stem loop structure typically contains the sequence GACG in the loop portion and is usually referred to as an essential packaging loop. In some instances, the highly conserved essential packaging loop, or Ψ loop, also contains an Aat2 restriction enzyme site, enabling the essential packaging loop to be joined or operably linked to a non-essential packaging sequence at the Aat2 restriction enzyme, which is a common site between these two sequences. A preferred essential packaging nucleic acid sequence is isolated from a murine leukemia virus ("MLV"), and more preferably from the Moloney strain MLV ("MoMLV").

A "non-essential packaging nucleic acid sequence" is composed of a nucleic acid sequence that extends beyond the 3'-terminus of the essential packaging loop that are not required for specific packaging into virus particles, but which enhance or add to the infectious titer of a virus or vector when present. Because these nucleic acid sequences are non-essential, the Ψ+ sequences are more variable than Ψ sequences, and there is no distinct 3'-terminus sequence boundary. For example, in MLV, the Ψ+ sequences are thought to extend from about basepairs 620 to about basepairs 1040 of the MLV genome (Bender et al., *J. Virol.*, 61:1639–1646 (1987)). These Ψ+ sequences include about a third of the gag gene sequence. In mouse VL30, the 3'-terminus of the Ψ+ region has not been completely defined, but it may include regions extending from the GACG loop to the end of the VL30 genome. However, the region within 700 basepairs of the GACG loop is of particular interest as it appears to contain powerful Ψ+ sequences as well as inhibitory sequences that can be removed to improve the titer of a packaging signal. The non-essential packaging nucleic acid sequence is typically an isolated VL30 nucleic acid sequence obtained from a rat or mouse. Preferably, an isolated mouse VL30 nucleic acid sequence is employed in a packaging signal of the invention.

Isolated, as used herein, means that a naturally occurring nucleic acid sequence, DNA fragment, DNA molecule, coding sequence, or oligonucleotide is removed from its natural environment, or is a synthetic molecule or cloned product. Preferably, the nucleic acid sequence, DNA fragment, DNA molecule, coding sequence, or oligonucleotide is purified, i.e., essentially free from any other nucleic acid sequence, DNA fragment, DNA molecule, coding sequence, or oligonucleotide and associated cellular products or other impurities.

Vector designations preceded by a lower case 'p' indicate plasmid DNA (transfection), whereas vectors designated by all upper case letters indicate the virus (transduced) form.

BRIEF DESCRIPTION OF THE DRAWINGS

FIG. 1 shows vector constructs: pVLSIB, pVLMB1,2, pBAG, pVLBIRY, and LN-β.

FIG. 2 shows a chimeric packaging signal: MoMLV Ψ packaging nucleic acid sequence (SEQ ID NO: 22) and VL30 Ψ+ packaging nucleic acid sequence (SEQ ID NO: 23). Sequence starts with the first base after the CA dinucleotide, which terminates the LTR.

FIGS. 3A–3E shows Matrix comparison plots: Moloney strain of MLV vs: A) BAG; B) VLMB2; C) LNL6; D) VLSIB; E) VLBIRY. All sequences start from RNA base 1 and extend to base 2232. Pustell DNA matrix in the MacVector program was used (Oxford Molecular, Campbell, Calif.).

FIGS. 4A–4G shows the complete gene sequence for the MoMLV virus, the gag gene sequence is indicated as the nucleic acid sequence extending from basepair 621 to basepair 2237.

FIGS. 5A–5C shows the nucleic acid sequence for vector pVLMB1 (SEQ ID NO: 1).

FIGS. 6A–6C shows the nucleic acid sequence for vector pVLMB2 (SEQ ID NO: 2)

FIGS. 7A–7C shows the nucleic acid sequence for vector pVLMB3 (SEQ ID NO: 3).

DETAILED DESCRIPTION OF THE INVENTION

The present invention relates to viral chimeric packaging signals that provide efficient and less harmful transmission of genetic vectors by retroviral particles. The packaging signal, described in detail below, typically contains at least one essential packaging nucleic acid sequence operably linked to at least one non-essential packaging nucleic acid sequence. Advantageously and preferably, the chimeric packaging signal employed in a vector lacks gag gene sequences. By eliminating gag gene sequences from a packaging signal of the invention, the packaging signal when employed in a vector, is less harmful when administered to a mammal and therefor can be used in a variety of biotechnological applications. Thus, the present invention also relates to gene transfer and gene therapy generally, and to the safety of retrovirus-derived and retrotransposon vectors, and combination or viral chimeric vectors.

Packaging signals of the present invention employed in a vector, are useful for the delivery of genetic material, i.e., gene sequences, either in vivo or by ex vivo methods. Importantly, vectors employing packaging signals of the invention can be delivered permanently and efficiently when compared to existing vectors, into cells and tissues for use in gene therapy or cell therapy in a mammal, and particularly in a human. For example, by employing a packaging signal of the invention in a vector for genetic therapy in a human, the generation of replication competent retrovirus ("RCR") may be reduced and perhaps even eliminated, while the increased efficiency of the vector can facilitate the effectiveness of a gene therapy protocol.

Packaging signals of the invention may also be used in agriculture, for example, for the production of proteins in animals, as in milk, meat, or egg protein (also called pharming). In pharmaceuticals, packaging signals of the invention may also be used to insert and/or express genes in cultured cells, or in bio-reactors. In industry, the packaging signals may be used to produce enzymes, antibiotics, antibodies, antisense RNA, ribozymes, cytokine molecules, or substitute human proteins, nucleic acids or hormones. In short, all the functions to which retroviral or retrotransposon vectors or combinations thereof possess, are also functions to which the packaging signals of the instant invention can be applied.

A. Packaging Signals of the Invention

Packaging signals of the invention and methods of using the packaging signals in a vector, provide multiple advantages over traditional vector systems. One advantage is that the infectious titer of a vector employing a packaging signal of the invention is significantly higher than a retrovirus-derived vector lacking the instant packaging signal. As used herein, the "infectious titer" refers to the number of infectious units or transducing units per milliliter of solution, i.e., (TU)/ml. Preferably, the infectious titer of a vector containing a packaging signal of the invention provides a vector that demonstrates an infectivity of about $10^6$ transducing units/milliliter (TU/ml) which is at least about one to about three times greater than similar retroviral vectors without gag gene sequences, and approximately equivalent to retroviral vectors containing gag gene sequences. Another significant advantage is that by employing the packaging signal of the invention in a vector, the vector lacks certain recombination-prone gag gene sequences found in currently used retrovirus vectors that have a similar high titer. Thus, the packaging signal of the present invention provides less hazardous vectors for genetic therapies and further reduces gag gene genetic recombination events that could potentially generate RCR outbreaks or occurrences. A packaging signal of the invention preferably lacks viral gag gene sequences, and may further include a splice acceptor site, a multiple cloning site for the insertion of a foreign gene sequence, a linker, an adapter, and a joining site, such as the Aat2 site.

As described herein, it is desirable to reduce gag gene sequences from a packaging signal and replace the gag gene sequence with a Ψ+ nucleic acid sequence isolated from a mammalian VL30 nucleic acid sequence. Preferably, the source of the Ψ+ nucleic acid sequence is an isolated nucleic acid sequence from a mouse VL30 nucleic acid sequence. Although Ψ+ nucleic acid sequences from other mammalian VL30 sources can be utilized, potential disadvantages may exist. For example, a possible disadvantage of a Ψ+ nucleic acid sequence isolated from a rat VL30 sequence is that these sequences can potentially be involved in 3-way recombination events between ras oncogenes, the MLV genome, and the rat VL30 sequences. This recombination can lead to oncogenic retroviruses characterized by acute transforming capability (e.g., the Harvey, Kirsten, and Rasheed sarcoma viruses), and it is known that these viruses can generate sarcomas quickly when re-injected into animals. In the present invention, however, and in contrast to the problems observed with Ψ+ nucleic acid sequences isolated from rat VL30 sequences and MLV sequences, a Ψ+ nucleic acid sequence isolated from a mouse VL30 sequence has not been implicated in either oncogene activation or in acute transforming capability (acquisition of growth-transforming sequences by a virus or vector). This result indicates a low level of transforming capability associated with a Ψ+ nucleic acid sequence isolated from a mouse VL30 sequence when compared to MLV Ψ+ or rat VL30 Ψ+.

Recently, however, a recombinant virus was reported wherein a mouse VL30-like element recombined with a murine retrovirus, resulting in a RCR (Wolgamot et al., *J. Virol.*, 72:74559–7466 (1998)). This apparently resulted from two recombination events. The first recombination event apparently took place in a region of homology between the VL30 sequence that contained a gag coding region similar to that of MLV, and an equivalent region of MLV. The recombinogenic gag coding region of the mouse VL30 is absent in some VL30 sequences and therefore provides a desirable VL30 backbone that has already been utilized to provide VL30 vectors. The mouse VL30 backbone is therefore a good candidate for a non-recombinogenic vector that does not contribute to the generation of a functional gag gene sequence. The second recombination event appeared to occur in the last few base pairs of the mouse VL30 genome located before the LTR, and possibly positioned in or in close proximity to the polypurine tract (plus strand primer binding site).

In view of the recombination events described above, it is therefore desirable to employ the Ψ+ nucleic acid sequence of a non gag-containing mouse VL30 into a retroviral vector, in lieu of the problematic gag gene. The resulting chimeric vector would be especially desirable if the titer of the chimeric vector of the combination of the Ψ+ nucleic acid sequence of a non gag-sequence containing mouse VL30 and retroviral vector were high, i.e., typically, about $10^6$ transducing units/milliliter (TU/ml) or greater. The higher titer chimeric vector would thus provide an efficient gene transfer mechanism that is less hazardous when employed in a genetic therapy application. By employing a non-gag gene sequence containing mouse VL30 Ψ+ nucleic acid sequence in a vector, such as a retroviral vector, packaging signals of the invention can provide higher titers than conventional non-gag gene sequence containing vectors and approximating or equal to titers of gag-gene sequence containing vectors. Therefore, the substitution of an equivalent, non-gag Ψ+ nucleic acid sequence from mouse VL30, is a significant advantage of the present invention. A potential non-gag gene sequence includes, for example SEQ ID NO: 23. The uniqueness of this advantage, however, depends upon the structure of the nucleic acid backbone. For example, in a nucleic acid backbone, such as the one described above, there are both primary (the nucleic acid sequence(s) themselves) and secondary (folding) aspects to the structure of the nucleic acid backbone. Thus, although very little nucleic acid sequence homology exists between MLV and mouse VL30 encapsidation signals, MLV and mouse VL30 (like other mammalian type C retrovirus elements) do share a 'hairpin', or stem-"loop" type nucleic acid sequence (containing a GACG loop). In some mammalian type C retrovirus-elements, there is also an Aat2 restriction endonuclease digestion site in the hairpin. This stem-loop type nucleic acid sequence can serve as a convenient place to operably link or functionally join the nucleic acid sequences that make up a packaging signal. This can be accomplished by means of standard recombinant DNA technology. Additionally, the hairpin sequence in retroviruses is thought to be a potential protein binding site responsible for virus packaging, although the mechanism is not well-understood.

As used herein, the term "operably linked" or "functionally joined," is defined to mean that at least one nucleic acid sequence is placed in a functional relationship with at least one other nucleic acid sequence (e.g., an essential packaging signal nucleic acid sequence and a non-essential nucleic acid sequence). For example, a promoter or enhancer is "operably linked" to a coding sequence if it affects the transcription of the sequence if it is positioned so as to facilitate translation. Generally, "operably linked" means that nucleic acid sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

In one embodiment, the present invention provides a packaging signal having a VL30 Ψ+ nucleic acid sequence operably linked to a MLV Ψ nucleic acid sequence. Preferably, the VL30 Ψ+ nucleic acid sequence is isolated from a mouse. This packaging signal combination, a VL30 Ψ+ nucleic acid sequence and a MLV Ψ nucleic acid sequence, provides a vector possessing high infectivity without the use of a gag gene sequence. When there is no gag gene sequence, the VL30 Ψ+ sequence has only a moderate titer ($10^3$–$10^5$ (TU/ml)) when it is used as a part of VL30 vectors. Thus, it was unexpected to find that the mouse VL30 Ψ+ region, in combination with the MLV Ψ region results in a high infectivity without employing gag gene sequences.

Thus, the present invention provides vectors that are less harmful to a mammalian subject treated with a vector containing the packaging signals of the invention. Packaging signals of the invention are less harmful, and therefore improved, as there are no gag gene sequences in the cis-acting sequences of a vector system. There is improvement in vectors of the invention in that resulting vectors containing the packaging signals of the invention vector cannot undergo gag gene sequence recombination with helper virus or with endogenous viruses in the helper cell. Additionally, the mouse VL30 Ψ+ nucleic acid sequences used in the vector have not led to acute transforming retroviruses, and therefore the Ψ+ portions of VL30 vectors are useful substitutes for functionally equivalent retroviral sequences.

C. Preparing Packaging Signals of the Invention

In general, the chimeric vectors employing packaging signals of the invention are prepared by selecting suitable sources for the essential, non-essential, and other optional nucleic acid sequences employed in the invention. These sources include, for example plasmids pNVL3 (Carter et al., *Nucleic Acids Res.*, 18:6243–6254( 1983)), pHa7 (Harvey Sarcoma Virus, courtesy of Dr. P. Duesberg, UCB, Berkeley, Calif.), and pBAG, (courtesy of Dr. C. Cepko (Price et al., *Proc. Natl. Acad. Sci.* 84:156–160 (1987)). Although other sources are readily available, the above described sources provide many of the components necessary for preparing the packaging signals of the invention, and fro assembling complete vectors.

When preparing a packaging signal of the invention, it is important, as stated above, to reduce the presence of potential gag gene sequence sources. Potential sources of gag gene sequences include the vector employed, e.g., MLV-derived vector sequences, helper sequences (where the gag gene is obligatory), VPCs (murine cells have many MLV-related retroviruses embedded in the genome, and these can sometimes be activated), and the target cell (the human genome contains defective retroviruses, but not murine retroviruses). It is preferable to reduce potential gag gene sequences from each of these potential sources except the helper virus. To do this effectively, the sequences must be absent from the vector backbone. This can be accomplished either by truncating the packaging sequences prior to the start of the gag gene sequences, or by substituting a Ψ+ sequences, such as the VL30 Ψ+ sequences of the instant invention, that contain no gag gene sequences.

For most known retroviruses, the cis-acting vector sequences and trans-acting helper sequences contain sequence overlap. This sequence overlap is a result of the overlap between the non-essential packaging nucleic acid sequence, which can greatly increase the efficiency of transmission of a vector, and the viral gag gene sequence, which is responsible for production of the viral core particle, or capsid. By eliminating the viral gag gene sequence, sometimes referred to as the 'half-gag' or 'Ψ+') from the packaging signal employed in a vector, the vector becomes less hazardous to use as RCR are essentially eliminated.

Packaging signals that lack the viral gag gene sequences may demonstrate a reduced titer, i.e., the number of infectious units. This reduction of titer has been examined. For example, Dougherty et al., *J. Virol.*, 63:3209–3212, (1989), employed two related viruses, spleen necrosis virus (SNV) and reticuloendotheliosis virus (REV) to prepare vectors that contained very little nucleic acid sequence homology. Although this approach eliminated some of the sequence similarity between the components of the vector system, the vectors were capable of generating RCR. Hodgson et al., U.S. Pat. No. 5,354,674 used retrotransposons ("RTNs"), such as the virus-like, 30S elements (VL30) of mice. VL30 genetic elements are cellular parasites that use retrovirus infections to transmit the VL30 genome between hosts and have little nucleic acid sequence homology to MLV or other retroviruses. Additionally, vectors that employ VL30 derived sequences, lack viral genes and possess little nucleic acid sequence similarity to their retroviral hosts. Presently, vectors employing VL30 derived sequences, have not resulted in any RCR. In addition, VL30 packaging signal regions are known to contain sites capable of internal ribosome entry (Chakraborty et al., *FASEB J.*, 7:971–977, (1983)), thus permitting translation to take place downstream from numerous ATG codons in the packaging signal. Although, less harmful than traditional vectors, the RTN vectors described by Hodgson et al., supra, were not as efficient as MLV Ψ+ vectors, such as those described by Armentano et al., *J. Virol.*, 61:1647–1650, (1987), and by Bender et al., *J. Virol.*, 61:1639–1646 (1987). For example, when transmitted by conventional retroviral helper cells, vectors employing VL30 derived nucleic acid sequences, generally possess titers in the range of about $10^3$ to about $10^5$ transducing units/milliliter (TU/ml) compared to $10^5$–$10^7$ TU/ml of MLV Ψ+ vectors containing half-gag gene sequences.

Thus, in one embodiment of the invention, at least one MLV nucleic acid sequence is employed to prepare a packaging signal. A source for MLV nucleic acid sequences, as stated above, are type C leukemia viruses. Preferably, at least one MLV nucleic acid sequence is a Moloney MLV derived nucleic acid sequence as shown in SEQ ID NO: 22. Representative vectors of the invention that contain at least one MLV nucleic acid sequence in the packaging signal are pVLMB1 (FIG. 5, SEQ ID NO: 1), pVLMB2 (FIG. 6, SEQ ID NO: 2) and pVLMB3 (FIG. 7, SEQ ID NO: 3). Each of the these exemplary vectors contain an LTR, (–)-primer binding site ((–)PBS), splice donor and Ψ from MLV. Optionally, an internal ribosome entry site ("IRES") may be included. For example, Torrent et al., *J. Virol.*, 68:661–667 (1994) and Torrent et al., *Human Gene Therapy*, 7:605–612, (1996), have described a region of the rat VL30 gene, approximately 65–180 bp, that is capable of acting both as an IRES and as the essential Ψ region, conferring a titer comparable to some MLV vectors.

In preferred embodiment of the invention, a packaging signal contains an [LTR(–) PBS-Aat2] sequence and Aat2+

678 bp sequence. The [LTR(−) PBS-Aat2] is derived from MLV. The [LTR(−) PBS-Aat2] nucleic acid sequence corresponds to the first 222 basepairs (bp) after the LTR terminal 'CA dinucleotide' of the published Moloney MLV sequence (Weiss et al., RNA Tumor Viruses, Cold Spring Harbor Laboratory Press, pp. 770 (1985)). The Aat2+678 bp is a mouse VL30 element from NVL-3 (Adams et al., *Mol. Cell. Biol.* 8:2989–2998 (1988)). Elements of the base structure of a vector containing a packaging signal of the invention is shown in Formula 1 below:

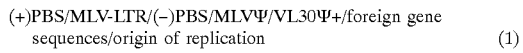

(+)PBS/MLV-LTR/(−)PBS/MLVΨ/VL30Ψ+/foreign gene sequences/origin of replication    (1)

As shown in Formula 1, (+)PBS represents a plus strand primer binding site, the MLV-LTR is a murine leukemia virus long terminal repeat nucleic acid sequence (murine MLV-LTR), the (−)PBS represents the minus strand primer binding site which is complementary to a cellular tRNA; the MLVΨ element is the murine leukemia virus basal packaging signal that is derived from the tRNA primer binding site up to and including the essential packaging hairpin region; the VL30Ψ+ element is isolated from the mouse VL30 packaging enhancer region. Referring now to FIG. 2, the VL30Ψ+ element extends from the essential packaging stem-loop structure (Aat2 site), through a series of tandemly repeated sequences (characterized by Dra3 restriction sites) that are found in the 3'-half of the sequence. If desired, all or a portion of the tandem repeat region may be eliminated or truncated, or the tandem repeat region may be modified by the substitution and/or insertion of additional nucleic acid sequences into the Dra3 sites. Lastly, the packaging signal can be operably linked to at least one foreign nucleic acid sequence. The foreign nucleic acid sequence can be any foreign gene or regulatory sequence, for example, full-length or portions of a therapeutic gene, including, but not limited to those encoding hormones, cytokines, growth factors, enzymes, antibodies, ligands, receptors, inhibitors, agonists, abyzymes, ribozymes, antisense sequences, and the like. These foreign nucleic acid sequences can further include marker and/or reporter genes, triple helix-forming sequences, an origin of replication (ori) for a second host (i.e., a plasmid origin of replication) or an internal ribosome entry site (IRES).

In another preferred embodiment, Formula 1 is a circular sequence wherein the foreign nucleic acid sequences terminate with a prokaryotic origin of replication (ori) and form a circle, followed by the (+)PBS sequence. In this preferred embodiment, the packaging signal has a single LTR located at the 5'-end of the packaging signal, and employs a plasmid origin of replication within the bounds of the vector. This arrangement allows for the efficient propagation of the vector construct in a prokaryotic cell, such as *Escherichia coli*. In this embodiment, transmission by retrovirus results in an integrated form of the vector construct that is flanked by long terminal repeats ("LTRs"). Alternatively, the nucleic acid sequences positioned between the (−)PBS and the (+)PBS sequences are flanked by LTRs, and the prokaryotic origin of replication is located on outside the retroviral LTRs, in the plasmid portion of the vector. It should be noted, however, that typically any standard retroviral vector construct employing or requiring a packaging signal, can readily be employed as a vector backbone for the present invention.

In another preferred embodiment, the packaging signal of the invention is conserved, and the vector derived sequences are modified and/or contain substitutions. For example, any LTR may be switched for a different LTR (from another VL30 element such as: NVL-1, NVL-2, NVL-3, BVL-1, VL3, VM1, TLEV, VLSI, PB10, PA2, VL11, VLOV1, and VLOV2), or for the LTR of a non-MLV retrovirus, or for a synthetic LTR or promoter. Additionally, the tRNA primer binding site (−)PBS can be readily exchanged for an alternative primer binding site. Importantly, the interchangeability of the elements described above that make up a chimeric vector containing a packaging signal of the invention, is not limited to the use of conventional restriction enzymes and ligation procedures. See, for example, WO 98/38326.

As set forth above, an LTR derived from a NVL-3 VL30 element can be employed in a packaging signal of the invention. The nucleic acid sequence of the NVL-3 element was first reported by Adams et al., *Mol. Cell. Biol.* 8:2989–2998 (1989)). Additionally, an LTR derived from BVL-1 can also be employed, however, this VL30 sequence is known to contain an additional gag gene sequence region. (Hodgson et al., Nucleic Acids Res. 18:673 (1990)). Thus, a VL30 nucleic acid sequence derived from a BVL-1 element is less preferred, as it contains gag-like gene sequences. It is thought that sequences derived from the BVL-I element may recombine with retroviral homologues thus generating RCR. The repeat region in the preferred VL30 element is typically characterized by the presence of Dra3 restriction endonuclease sites in each copy of the repeat. In preferred embodiment, at least one of the Dra3 repeat sequences are removed by digestion with Dra3, followed by religation (preferably with a linker, such as a Cla1 8 bp linker, inserted into the Dra3 site to disrupt the repeat. Significantly, the Dra3 repeat, similar to a 'B Box' transcription factor binding site, is disrupted by the insertion of a linker.

Additional preferred embodiments of the present invention include, but are not limited to, a packaging signal having: 1) an MLV Ψ sequence that extends from the 3'-terminus of the LTR to the Aat2 site (SEQ ID NO: 22); and 2) a mouse VL30 Ψ+ sequence derived from NVL-3, that is contiguous with and extends from the Aat2 site through the overlapping tandem repeat region (SEQ ID NO: 23). In this embodiment, 678 basepairs (bp) of NVL-3 extending from the Aat2 are incorporated into the packaging signal (SEQ ID NO: 23). In this embodiment, the Aat2 site is conveniently used to join or operably link these two elements of the packaging signal. The vector construct pVLMB2, FIGS. 1 and 6, (SEQ. ID. 2), is a representative example of this embodiment.

D. Administration of Vectors of the Invention

It should be appreciated that vectors prepared with the packaging signals of the present invention can be readily utilized for the same purposes as other known retro-vectors. A variety of administration routes for genetic material are well known in the literature. For human genetic therapy, the route of administration can be in vitro (also called ex vivo), wherein cultured cells are administrated to a patient after insertion of a vector(s) into a cell population by retroviral infection (Anderson et al., U.S. Pat. No. 5,399,346). A variety of different cell populations or cell types can be employed. For example, a cell population can be fibroblasts taken from patient skin, or they can be VPCs producing vectors (for example, injected into a tumor site). Alternatively, vectors can be administered in vivo (directly to the patient). An in-vivo route of administration includes, but is not limited to, intra-venous, intra-arterial, intra-muscular, intra-peritoneal. The vectors can also be administered by aerosol, for example, into the lung, or by suppository (or gastrointestinal lavage) into the digestive system.

To use any of these methods, the vector (virus) is first harvested by removing the cell culture media from the VPCs after exposing the VPCs to the media for at least about 12 hours. The media is then sterile filtered (0.45 micron, Nalgene) to remove cell debris, and the virus-containing filtrate may be further concentrated, if necessary, by centrifugation or by Microcon filtration (Microcon, Inc., Beverly, Mass.). The method and materials used preparing the virus and infecting cells are well known, and production of vector material has been extensively described in the literature (Ausubel et al., Current Protocols in Molecular Biology, Section III, pp. 9.9.1–9.17.3(1995–1998)). Briefly, a recombinant DNA molecule can be introduced into a cell population, e.g., helper cells, either by transfection, or by transduction (viral transfer). Once inside the helper cell (now a VPC), the virions produced by the cell are secreted into the cell growth media. The media can be filtered (for example, by tangential flow filtration) or centrifuged to concentrate or purify the vector virus preparation. The virus preparations can be frozen or freeze-dried for preservation prior to use, after which the virus is reconstituted and directly contacted with the target cells. The virus attaches by means of the envelope glycoprotein, and cellular receptors (such as the retroviral amphotropic receptor, or the Gibbon ape leukemia virus ("GALV") receptor. The env protein is a ligand which attaches the virion to the cellular protein receptor. The env protein complex also contracts, forcing the cytoplasm to come into direct contact with the capsid.

Some envelope glycoproteins appear to mediate direct entry into the cytoplasm, while others appear to stimulate endosomal uptake. Once the capsid is free inside the cell, replication begins or continues. The RNA is reverse transcribed as double-stranded DNA which can be either linear or circular. The DNA is then integrated into the chromosomal DNA of the recipient cell by means of the reverse transcriptase-associated integrase activity. In order for this to happen, retroviral DNA (or retro-vector DNA) must come into contact with the cell DNA without passing through the nuclear pore, because the pre-integration complex is presumably too big and is not actively transported inside the nucleus. This means (in the case of type C retroviral vectors, but not lentiviruses) that the cell must divide, temporarily dissolving the nuclear membrane and permitting the vector DNA to come into contact with the nucleus. The viral integrase enzyme activity that is associated with the reverse transcriptase then digests the termini of the virus or vector RNA molecule and also the cell DNA, permitting the virus or vector genome to be integrated into the cell. In the case of lentivirus vectors, for example, active transport permits the virus nucleic acid to enter the nucleus. In both lentivirus and simple retrovirus infections, the integration event is both highly specific with respect to the ends of virus or vector sequences, and less specific or even very non-specific with respect to the chromosomal loci. Thus, there are many chromosomal loci into which the vector can insert. The degree of specificity (or lack thereof) of insertion is an important determinant of positional targeting.

The efficiency of viral infection is dependent upon the efficiency of the packaging signal, and also upon other factors, such as the charge on the surface of the cell and virus (usually negative in both cases). As used herein, "efficiency," refers to the ability of the vector sequences to package efficiently in VPCs. The surface charge can be reduced by pre-treating the virus with a polycation such as polybrene (hexadimethrine bromide), or preferably a lipopolycation such as DOSPA:DOPE (Lipofectamine™, Life Technologies, Gaithersburg, Md.) (Hodgson et al., Nature Biotechnol., 14:339–42 (1996)). For in vivo use, proprietary lipids have been developed which are more compatible with human serum and tissues (Porter et al., J. Virol., 72:4832–4840 (1998)); Themis et al., Gene Ther., 5:1180–1186 (1998)). Another preferred reagent such as polyamidoamine (PAMAM) dendrimers can also be used (Hodgson et al., J. Mol. Med., 75:249–258, (1997) and Hodgson et al., WO 96/26745)). These pre-treatments can increase infectivity of a vector of the invention by as much as about 30 to about 200 fold increase, preferably about 40 to about 100 fold, and more preferably about 50 to 70, or more. Once integrated or incorporated into a cell, the vector can be targeted to express the genes in specific cells by means of transcriptional promoters recruited into the LTR, the so-called promoter rescue technique (Hodgson et al., WO 98/38326).

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The following examples are intended to illustrate but not limit the invention.

EXAMPLE 1

Vector Design and Construction: Singe LTR Vectors

Plasmids pNVL3 (Carter et al., Nucleic Acids Res., 18:6243–6254(1983)), pHa7 (Harvey Sarcoma Virus, courtesy of Dr. P. Duesberg, UCB, Berkeley, Calif.), and pBAG, (courtesy of Dr. C. Cepko (Price et al., Proc. Natl. Acad. Sci. 84:156–160 (1987)), were used as sources for mouse VL30, rat VL30 and MLV vector sequences, respectively. Vector construct DNA was transformed into E. coli SCS110 (dam-, dcm-) competent cells (Stratagene Corp., LaJolla, Calif.), and colonies were grown in LB broth supplemented with kanamycin, 75 micrograms/milliliter ($\mu$g/ml). Vector DNA was isolated using Qiagen™ kits (Qiagen Corp., Chatsworth, Calif.). Junctions of the constructed vectors were confirmed by DNA sequencing. All vector constructs are shown in FIG. 1. Each of the vectors shown in Table 1 were constructed by standard recombinant DNA techniques (Ausubel et al., Current Protocols in Molecular Biology, Section III, pp. 9.9.1–9.17.3(1995–1998)). DNA cloning was performed according to standard protocols described in Ausubel et al., Current Protocols in Molecular Biology, Section III, pp. 9.9.1–9.17.3 (1995–1998). All enzymes employed herein were obtained from either Boehringer Mannheim GmbH, Indianapolis, Ind.) or New England BioLabs (Natick, Mass.).

pVLSIB

A Xho I fragment (4.2 kilobases (kb)) from pNVL3 was isolated from a 1% agarose gel, purified with Geneclean (BIO101, Inc., LaJolla, Calif.), and was circularized. The resulting product was subsequently linearized with Sna B1. A Xho I-Bam HI fragment (2.3 kilobases (kb)), containing the prokaryotic pBR322 origin of replication (ori) and the neomycin phosphotransferase gene (Neo) expressed by the SV40 virus early promoter from the plasmid pBAG, was blunted using T4 DNA polymerase and dephosphorylated (using calf intestinal alkaline phosphatase). The NVL-3 and BAG fragments were ligated, forming pVLSNO2. Two fragments (57 basepairs (bp) and 1,564 basepairs (bp)) were removed from this construct by Bpm I digestion, resulting in the final product (pVLSIB). The encephalomyocarditis virus (EMCV) internal ribosome entry site (IRES) and the β-galactosidase (β-gal) gene were inserted into a unique Bam HI site. The resulting vector has the LTR, Ψ, and Ψ+ regions derived entirely from mouse VL30 (Table 1).

pVLMB1, pVLMB2, and pVLMB3

The plasmid pBAG was digested with Xba I, and the resulting plasmid fragment was then circularized, giving rise to a single LTR rendition of the pBAG vector. The fragment Rsr II-Aat2, including the LTR and the minimal Ψ signal up to the Aat2 site (located in the GACG loop), was isolated and inserted into the same complementary site of pVLSIB. The resulting construct pVLMB1 (FIG. 5, SEQ ID NO: 1) contained the LTR, (−)-primer binding site, splice donor and Ψ from MLV. The Ψ+ region (678 basepairs (bp)) was derived from mouse VL30 (Table 1). During sequence validation of VLMB1, it was discovered that this vector contained an additional 52 basepair (bp) duplication of a nucleic acid sequence extending from the end of the [−]-strand primer binding site to the splice donor site of MLV. This was apparently the result of a mutation.

Vector pVLMB2 (FIG. 6, SEQ ID NO: 2) can be prepared in the same manner as pVLMB1, except the vector lacks the additional 52 basepairs (bp) duplication of sequences which occurred as a mutation in pVLMB1.

Vector pVLMB3 (FIG. 7, SEQ ID NO: 3) is also prepared in the same manner as pVLMB1, but further contains a deletion in the Ψ+ (VL30-derived region). The deletion is made by substituting the 108 basepair (bp)Aat2-Cla1 sequence of VLCN (Hodgson et al., *Retro-vectors for Human Gene Therapy*, Chapman and Hall, New York, Springer-Verlag, Berlin, Heidelberg (1996)) for the 678 bp Ψ+ region of VL30 that is found in pVLMB1 and VLMB2.

pLN-β

To prepare the pLN-β vector, the vector G1IL2EN (Triesman et al., *Blood*, 85:139–145 (1995)) was digested with XhoI and NotI to remove inserts. The resulting 6 kilobase (kb) vector fragment was treated with mung bean exonuclease and calf intestinal alkaline phosphatase. The vector fragment was subsequently ligated to a 3.2 kb SspBI-ApaI fragment containing the β-gal sequence from pVLMB1, which had also been treated with mung bean exonuclease.

pVLBIRY

The rat VL30 packaging signal (161 basepairs (bp), from base 190 to base 351 of HaMSV (Torrent et al., *J. Virol.* 68:661–667 (1994)) was recovered by polymerase chain reaction (PCR) from Harvey sarcoma virus (pHa7) using the primers Ha1 (SEQ ID NO: 4) and Ha2 (SEQ ID NO: 5), shown below, to generate a fragment with complementary Ppu MI and Aat2 restriction endonuclease sites on the 5' and 3' termini, respectively. The PCR product was subsequently digested with the Ppu MI and Aat2 enzymes, and the resulting fragment was introduced into the Ppu MI-Aat2 deletion site of the mouse VL30 vector pVLSNOGMIS (Hodgson et al., WO 98/38326). The Apa I-Rsr II fragment (containing green fluorescent protein (GFP)) of pVLSNOGMIS, was replaced with the Apa I-Rsr II fragment (β-gal) of pVLSIB, producing pVLBIRY. The pVLBIRY. vector has the LTR and (−) primer binding site from mouse VL30. The canonical splice donor site, dimerization linkage site, and the remainder of the essential packaging signal were from rat VL30, and the Ψ+ region was derived from mouse VL30.

Primers:
Ha1 (SEQ ID NO: 4):
    5'-CACCCAGAGGTCCTAGACCCACCACCGGGA GGCAAGCCGGCCGG-3'
Ha2 (SEQ ID NO: 5):
    5'-TCCAACCACGCTTGGGACGTCTCCCAGGGCT GCGGGGGAGAA-3' pVLMCB

The technique of Gene Self-Assembly (GENSA™, as described in Hodgson et al., WO 98/38326) can be used to insert the packaging signal of the instant invention into any chimeric retro-vector. For example, using three vector templates VLMB1, VLCN, and the retroviral BAG vector (Price et al., *Proc. Natl. Acad. Sci.* 84:156–160 (1987)) and sixteen primers (SEQ ID NOS: 6–21), it is possible to assemble the vector pVLMCB from eight fragments, comprising a prokaryotic plasmid origin of replication, a mouse VL30 (NVL-3) LTR, the Ψ signal from MLV, the Ψ+ from VLCN, the selectable neo gene, the EMCV IRES, the β-gal reporter gene, and the 3'-LTR of the mouse VL30 (NVL-3). The primers (SEQ ID NOS: 6–21) employ the class IIS restriction enzyme Sap1 to create unique, non-palindromic overlapping ends that can ligate to only one other terminus in the complex mixture of eight fragments. Equimolar quantities of the Sap1-digested, gel-purified fragments are combined by ligating at 16° C., for 16 hours at a concentration of about 1 micromolar ($\mu$M) to about 2 micromolar ($\mu$M) 5'-ends using T4 DNA ligase (Boehringer Mannheim GmbH, Indianapolis, Ind.). Using similar methods, the packaging signals of the instant invention can be combined with any retro-vector.

EXAMPLE 2

Primers and Templates

The nucleic acid sequences below are representative primers and templates below for preparing a packaging signal of the invention. The SapI sites are in "bold" print, 3 base digestion site overlaps and one base jumps are indicated by "spaces" between the sequences. A hybridizing section of the primer is underlined.

A. Fragment 1, PBR ori (VLCN Template)
SEQ ID NO: 6:
    P1- GATTCCA GCTCTTC G T AATCTGCTGCTTGCAAACAAAAAAACCACC-3'
SEQ ID NO: 7:
    P2- GATTCCA GCTCTTC A TCT GGCGTTGCTGGCGTTTTTCCATAGG-3'

B. Fragment 2, NVL-3 LTR/(−)pbs (VLCN Template)
SEQ ID NO: 8:
    P3- GATTCCA GCTCTTC C AGA GCATGCCTGCAGGTCGACTCTAGAGGA-3'
SEQ ID NO: 9:
    P4- GATTCCA GCTCTTC A CCG TTCCCGGCCAATGCACCAAATGAA-3'

C. Fragment 3, MLV-Ψ (BAG Template)
SEQ ID NO: 10:
    P5- GATTCCA GCTCTTC T CGG GAGACCCCTGCCCAGGGACCA-3'

SEQ ID NO: 11:
P6- GATTCCA GCTCTTC A CGT CTCCCAGGGTTGCGGCCGGGT-3'

D. Fragment 4, VLCN Ψ+/neo Fragment A, (VLCN Template)

SEQ ID NO: 12:
P7- GATTCCA GCTCTTC G ACG TCCCAGGAGGAACAGGGGATCA-3'

SEQ ID NO: 13:
P8- GATTCCA GCTCTTC G TCC AGATCATCCTGATCGAC-3'

E. Fragment 5, neo Fragment B, (VLCN Template)
5 SEQ ID NO: 14:
P9- GATTCCA GCTCTTC A GGA CGAG GAGCATCAGGGGCTCGCGCCAGCC-3'

SEQ ID NO: 15:
P10- GATTCCA GCTCTTC A GCA ATATCACGGGTAGCCAAC-3'

F. Fragment 6, neo Fragment C, (VLCN Template)
SEQ ID NO: 16:
P11- GATTCCA GCTCTTC T TGCTGAGGAGCTTGGCGGCGAATGGOCTGAC CG-3'

SEQ ID NO: 17:
P12- GATTCCA GCTCTTC A GAC AAATAATTCTAATCTTAGAATTTCAGAAGTCTA GCG-3'

G. Fragment 7, IRES-β-gal, (VLMB1 Template)
SEQ ID NO: 18:
P13 GATTCCA GCTCTTC G GTC GAGCGGGATCAATTCCGCCCC-3'

SEQ ID NO: 19:
P14- GATTCCA GCTCTTC T GCCCGGTTATTATTATTTTTGACACCAGAC-3'

H. Fragment 8, (+)pbs/NVL-3 LTR, (VLCN template)
SEQ ID NO: 20:
P15- GATTCCA GCTCTTC A GG CTGAAATTCTAAGATTAGAATTATTTACAAGAA GAA-3'

SEQ ID NO: 21:
P16- GATTCCA GCTCTTC A GGGAGACCGGAATTCGAGCTCGGTACC-3'

EXAMPLE 3

Cell Lines and cell Culture

Cell lines NIH 3T3, PG13, MOLT-4 and PA317 were obtained from the American Type Culture Collection, Rockville, Md. The GP+E-86 cell line was provided by Dr. Arthur Bank, Columbia University, New York, N.Y.). All Cells were grown in Dulbecco's modified Eagle's medium (DMEM) (Life Technologies, Gaithersburg, Md.), supplemented with 10% (v/v) fetal bovine serum (FBS) and 1% antibiotic-antimycotic solution (Life Technologies). PA317, PG13 and GP+E-86 helper cells were pre-selected in HAT media (Miller et al., *Mol. Cell. Biol.*, 6:2895–2902 (1986)), or HXM media (Markowitz et al., *J. Virol.*, 62:1120–1124 (1988)), respectively, as specified. MOLT-4 cells were grown in RPMI 1640 medium (Life Technologies), supplemented with 10% fetal bovine serum and 1% antibiotic-antimycotic solution (Life Technologies).

Establishment of Vector Producer Cell Lines

Plasmid vectors were transfected into PA317 helper cells using generation 6 polyamidoamine (PAMAM) dendrimers as described (Hodgson et al., *J. Mol. Med.*, 75:249–258 (1997)). After 48 hours incubation, the supernatant from vector producer cells was filtered through a 0.45 micron Nalgene™ filter (Rochester, N.Y.) and used to transduce GP+E-86 and PG13 helper cell lines, respectively. Lipofectamine™ (Life Technologies) was used to enhance retroviral transduction as described (Hodgson et al., *Nature Biotechnol.*, 14:339–42, 1996)) for a 48 hour period. After the 48 hour period, he transduced cells were selected in cell culture media containing 800 µg/ml G418 (Life Technologies) for 2 weeks. After selection, transduced cells were trypsinized and grown as mass cultures. The supernatants were used for titer determination.

Titering Procedure

Vector producer cells (VPCs) were grown to approximately 90% confluence, and supernatants were removed to transduce target cells. NIH 3T3 or HT1080 cells (American Type Culture Collection, Rockville, Md., ATCC #CCL121) were plated in 6-well plates at a density of $1.0 \times 10^5$/well. Transduction was done using the Lipofectamine™ procedure described in (Hodgson et al., *Nature Biotechnol.*, 14:339–42, 1996)). After 48 hours, the cells were selected in media containing the drug G418 at a 800 µg/ml active concentration (Life Technologies, Gaithersburg, Md.,) for two weeks, and the G418-resistant 10 colonies were counted. Alternatively, and in addition to cell selection with G418, cells were stained with the X-gal procedure (Price et al., supra), and blue-stained cells were counted, and titers were calculated according to dilution factors. These two procedures produced comparable results.

For transient titering, the supernatant medium in which transiently transfected GP+E-86 cells and PA317 helper cells were incubated for 48 hours, was used to transduce NIH 3T3 or HT1080 cells using Lipofectamine™. After 48 hours, the transduced cells were stained with X-gal procedure (Price et al., supra), and blue cells were counted.

CD4+ T-cell Transduction and Selection

MOLT-4 cells were maintained at a density of $1–2 \times 10^6$ cells/ml in RPMI 1640 [SOURCE?] that contained 10% FBS, 200 IU/ml IL-2 (R & D Systems, Minneapolis, Minn.), and 1% antibiotic-antimycotic solution (Life Technologies). Rapidly growing cells were treated overnight with 5 milliliters (ml) of filtered supernatants (containing 8 µl/ml Lipofectamine™) from transiently transfected PA317 cells or stably transduced PG13 cells, and were changed to media without Lipofectamine™ for another 24 hours. G418 (400 µg/ml active concentration) was added to cultures 48 hours after the transduction. Cultures were drug-selected until non-transduced control cells were completely killed (approximately 7 days).

Similarity of Packaging Elements

Dot matrix comparisons were prepared using the Pustell DNA Matrix Analysis Program, (MacVector, Oxford Molecular). (FIG. 3).

EXAMPLE 4

Transfection, Transient Expression and Vector Titers Employing Packaging Signals from Different Sources Four vector DNA constructs were prepared that employed alternative packaging signals and LTR sequences from different sources. The LTR sequences and packaging signals were obtained from Moloney strain MLV, mouse VL30, and rat VL30 sequences and prepared as indicated above. The prepared vector DNA constructs were designated pVLSIB, pVLMB1 (lacking all gag gene sequences), pBAG, pLN-β, and pVLBIRY (FIG. 1, Table 1). The pBAG vector was constructed with two LTRs from MLV (Price et al., supra). Vector DNA constructs were transfected into three different packaging cell lines: GP+E-86 (provided by Dr. Arthur Bank) PG13 (American Type Culture Collection, Rockville, Md.), and PA317 (American Type Culture Collection (ATCC, Rockville, Md.). To determine the percentage of cells that were successfully transfected, cells were stained with the X-gal staining procedure to reveal transduced cells. (Price et al., supra). Approximately 10% to about 30% of the transfected cells stained blue after the X-gal staining procedure (Table 2). The blue staining indicated that transfected vectors in the cells containing LTR sequences were successfully transcribed into mRNA and that the β-gal marker gene of the vector was expressed as protein in the cells. The darker the blue is an indication that more RNA and protein were expressed.

Approximately 48 hours after transfection, cell culture media was harvested from VPCs expressing the vectors. Infectious virus particles were titered (by X-gal staining) on NIH 3T3 (American Type Culture Collection, Rockville, Md.) or HTI 080 cells (American Type Culture Collection, Rockville, Md., Accession number CCL121), and were utilized for transduction of GP+E-86 and PG13 cells to establish stable vector producer cells.

Results

The pVLMB1 vector demonstrated transient titers of approximately $0.5-1.0 \times 10^5$ TU/ml in all three packaging cell lines. These titers were about 1.5 to about 3.5 fold lower than the titers observed for the pBAG vector. The pBAG vector demonstrated transient titers ranging from about $1.0-3.5 \times 10^5$ TU/ml in all three tested cell lines. Although the pVLSIB vector demonstrated a lower transient titer (about $0.5-3.0 \times 10^3$ TU/ml) transfection efficiency and detected β-gal protein were comparable to that of the pBAG and pVLMB1 vectors in all three cell lines. The pVLBIRY and pVLSIB vectors each demonstrated transient titers of about $0.6-2.3 \times 10^3$ TU/ml. The pVLBIRY vector also exhibited a slightly reduced transfection efficiency, as determined by X-gal staining (about 10–20% blue cells compared to about 20–30% for pVLSIB, pVLMB1,2,3, pBAG, and pLN-β). Blue staining indicates positive staining for expression of β-gal, which is indicative of a functional vector that is expressing the reporter gene.

EXAMPLE 5

Transduction and Titers from Stable Packaging Cell Lines

Supernatants (as shown in Example 4) were obtained from transiently transfected PA317 cells (American Type Culture Collection, Rockville, Md.). GP+E-86 cells and PG13 cells (American Type Culture Collection, Rockville, Md.), were transduced with the supernatants from the transiently transfected PA317 cells. After selection with the drug G418 (800 μg/ml) for 6–10 days (until die-off was complete), more than 600 colonies were obtained from pVLMB1 and pBAG mass cultures. Approximately 30 to 50 colonies were observed for the pVLSIB and pVLBIRY vectors.

Staining of G418 drug-selected transduced GP+E-86 and PG13 cells indicated that approximately 80–100% of the G418-resistant cells stained blue, demonstrating that the β-gal marker gene was efficiently expressed from the pBAG, pVLMB1, pVLSIB, and pVLBIRY vectors in the GP+E-86 and PG13 packaging cell lines. Referring to Table 2, each of the four vectors generally had higher titers in stably transduced packaging cells than in the respective transiently transfected cells, with the exception of the pVLSIB vector, which was slightly lower. The infectious titer data was very reproducible, both between experiments and between experimental samples taken at the same time as shown in Table 2. Furthermore, the data were consistent when different helper cells and target cells were used.

The pBAG vector, stably integrated in GP+E-86 cells, produced a titer of $5.3 \times 10^5$ TU/ml in NIH 3T3 cells, and is representative of a typical titer for the pBAG vector. However, when the pBAG vector is packaged in PA317 cells, the vector typically demonstrated slightly lower titers in a range of about $1.0-3.0 \times 10^5$ TU/ml in NIH 3T3 cells. Surprisingly, in these experiments, the pVLMB1 vector demonstrated a titer that was approximately 6 to 14 fold higher than that of the pBAG vector. This result was in contrast to the transient transfection experiment wherein the pVLMB1 vector demonstrated a 1.7-fold reduction in titer relative to the pBAG vector.

The pVLSIB and pVLBIRY vectors indicated titers in the range of about $0.7-1.3 \times 10^4$ TU/ml after stable transduction. The pVLBIRY vector indicated a slightly higher titer than the pVLSIB vector, but the titers of these two vectors were at least 44 fold lower than that of the pBAG vector and 240 fold lower than the pVLMB1 vector.

EXAMPLE 6

RCR Marker Rescue Assay

As shown in Example 5 above, the pVLMB1 vector, which lacked all gag gene sequences, demonstrated significantly higher titer than either VL30-derived (VLSIB) or MLV-derived (BAG) vectors. This property might therefore be useful in gene therapeutic applications. Thus, to determine whether the increased titer may be the result of replication competent retrovirus (RCR), a marker rescue protocol was used to detect RCR potentially present.

RCR Assay

A marker rescue protocol was used to detect RCR. Briefly, HT1080 cells (American Type Culture Collection, Rockville, MD; Accession number CCL121) were first transduced with supernatant from PG13/pVLMB1 and selected with the drug G418 (Life Technologies). When stained with the X-gal procedure, the selected HT1080 cells showed nearly 100% blue cells (Price et al., supra) and were used as marker cells. Supernatants from the PG13/pVLMB1 cultures were continuously maintained in culture dishes for 4 months and were subsequently filtered and applied to marker-containing HT1080 cells using the Lipofectamine™ procedure. The resulting transduced marker cells were maintained for 2 weeks and split twice to permit growth and amplification of potential RCRs. The supernatants were subsequently filtered and added to fresh HT1080 target cells, and the X-gal staining procedure was used to detect infected cells. No RCR were detected, as the rescue assay was negative (<0.1 TU/ml).

EXAMPLE 7

Expression and Longevity of the pVLMB1 Vector in CD4+ T-Cells

To determine if the pVLMB1 vector could be efficiently transmitted to and expressed in CD4+ T-cells, human MOLT-4 cells (American Type Culture Collection, Rockville, Md.), were transduced with supernatants from either transiently transfected PA317 cells or stably transduced PG13 cells. X-gal staining demonstrated that 35% of the MOLT-4 cells were stained deep blue after G418 selection, and another 45% were slightly to moderately blue.

Additionally, to determine whether expression of the pVLMB1 vector in the T-cell line could be sustained, the stably transduced MOLT-4 T-helper cells were maintained in culture for seven months and subsequently stained with X-gal. The overall percentage of blue cells, either moderate or deep blue, were sustained at about 70% in the absence of G418 drug selection. Approximately 33% of the cells stained deep blue. These results demonstrated that the pVLMB1 vector was capable of sustained expression, i.e., over a seven month period, in a high percentage, about 70%, of MOLT-4 cells.

EXAMPLE 8

Comparison of pVLMB and pBAG to a Ψ+ MLV-Derived Vector

The pBAG vector contained up to bp 626 of the published MLV genome including the first two codons of the gag gene sequence, whereas the Ψ+ sequence extends from bp 620–1040. Therefore, we wished to compare VLMB1 and BAG with a Ψ+ MLV vector such as LN (Miller et al., *BioTechniques*, 7:980–990 (1989)). To do so, the vector pLN-β was constructed (FIG. 1), having the bp 215–1040 Ψ/Ψ+ packaging signal of MLV. In this set of experiments using mass cultures of transduced cells, LN-β had the highest titers (2.3–3.3×10$^6$ TU/ml), followed by VLMB1 (1.4–1.8×10$^6$ TU/ml) and BAG (0.53–0.71×10$^6$TU/ml).

EXAMPLE 9

Efficient Transmission by the Chimeric Packaging Signal of a GENSA Vector

To rule out the possibility that the efficiency of the packaging signal of the instant invention was somehow context dependent upon vector sequences other than the packaging signal, the vector GENSA981 A was constructed using Gene Self-Assembly (GENSA) technology (Hodgson et al., WO 98/38326). The GENSA981 A vector, contained the packaging signal copied in its entirety from VLMB1 using gene amplification as described in WO 98/38326. Additionally, the GENSA981A vector also combined with a number of other sequences not present in VLMB1. These sequences, which are described in WO 98/38326, were utilized to determine the GENSA981A vector's innate packaging capability in the absence of MLV env gene sequences and of mouse VL30 sequences that were in addition to the Ψ+ sequences of SEQ ID NO: 23.

The uncloned DNA assembly was transfected into PA317 cells, selected with G418 (500 μg/ml), and used to transduce PG13 cells. In two independent experiments, mass cultures of GENSA981A, obtained from transfected in vitro-assembled DNA, had titers of 3.2 and 1.6×10$^6$ TU/ml, respectively. The cells efficiently expressed a human growth hormone (hGH) gene encoded within the vector, resulting in 5.4 nanogram/milliliter (ng/ml) of hGH in the cell supernatant after 19 hours. Thus, the high titers obtained with the packaging signal of VLMB1 were not simply dependent upon the context of VLMB1, and the in vitro-assembled (uncloned) DNA efficiently transmitted and expressed two foreign genes (neo, imparting G-418 resistance, and hGH, a reporter gene that can be easily assessed by means of an immunoassay kit (Nichols Institute, Valencia, Calif.).

EXAMPLE 10

Similarity of Chimeric Vector Packaging Signals to the MLV gag Gene

To determine the degree of similarity, if any, that exists between the MLV retroviral gag gene and the sequences present in the chimeric vectors of FIG. 3, a series of similarity matrices were generated using the sequence 1-2232 of each sequence of MLV as a standard. The Ψ+ vector LNL6 (Miller et al., *BioTechniques*, 7:980–990 (1989)) was included for comparison. LNL6 has a long region of nucleic acid sequence similarity to MLV at the 5'-end of the genome (up to about 1,000 basepairs (bp), but BAG, VLMB2, VLBIRY, and VLSIB do not. This nucleic acid sequence difference represents the Ψ+ region of the MLV vector. A search for potential open reading frames (ORFs) in the chimeric packaging signals of FIG. 3, did not reveal any long open reading frames.

EXAMPLE 11

Matrix Comparison

To assess the potential for recombination between helper virus sequences and the packaging signal of the instant invention, similarity to the retroviral gag gene was determined by matrix comparison to MoMLV (FIG. 3). The half-gag gene-containing Ψ+ vector (LNL6); (Miller and Rosman, 1989) was included for comparison. LNL6 has a long region of sequence similarity to MLV at the 5'-end of the genome (up to 1,000 bp), but BAG, VLMB2, VLBIRY, and VLSIB did not. This difference represents the half-gag Ψ+ gene sequence region of the MLV vector. A search for open reading frames in the chimeric vectors revealed only short ones that did not appear to represent viral gene products. The instant invention overcomes the need for a gag gene sequence, increasing the titer ten fold over that of a non-gag gene sequence containing vector. The vectors VLMB1 & 2 are chimeras, derived from the first 222 bp (after the LTR) of MLV, and the Ψ+ region being from mouse VL30. Because the mouse VL30 Ψ+ sequence contains no viral genes, it cannot contribute viral genes to RCR.

In conclusion, an efficient packaging signal has been devised by fusing complementary portions of the essential Ψ element of MLV with the Ψ+ region of mouse VL30. The lack of gag gene sequence homology eliminates a source of recombination that has been problematic to retroviral vectors. The chimeric packaging signal can be used in mammalian type C retrovirus-derived vectors, retrotransposon vector, or chimeric vector.

TABLE 1

Molecular Origin of Vector Sequences.

| | LTR(-)PBS | | | Ψ | | | Ψ+ | | |
| --- | --- | --- | --- | --- | --- | --- | --- | --- | --- |
| | MLV | Rat VL30 | Mouse VL30 | MLV | Rat VL30 | Mouse VL30 | MLV | Rat VL30 | Mouse VL30 |
| VLSIB | | | X | | | X | | | X |
| VLMB1, 2, 3 | X | | | X | | | | | X |
| BAG | X | | | X | | | X | | |
| LN-β | X | | | X | | | X | | |
| VLBIRY | | X | | X | | | | | X |

TABLE 2

Comparison of Transfection Efficiency, Transient and Stable Titers (TU/ml) between Four Vectors in Different Packaging Cell Lines

| Cell line | Vector | Transfection efficiency (%) | Transient titers (mean ± SD) | | Titers for stable lines (mean ± SD) | |
| --- | --- | --- | --- | --- | --- | --- |
| | | | HT1080 | 3T3 | HT1080 | 3T3 |
| GP + E-86 | pBAG | 20–25 | — | $1.0 \pm 0.1 \times 10^5$ | — | $5.3 \pm 0.4 \times 10^5$ |
| | PVLMB1 | 20–25 | — | $5.8 \pm 0.4 \times 10^4$ | — | $3.1 \pm 0.8 \times 10^6$ |
| | pVLSIB | 20–30 | — | $1.2 \pm 0.4 \times 10^3$ | — | $6.6 \pm 0.3 \times 10^3$ |
| | pVLBIRY | 15–20 | — | $6.4 \pm 4.2 \times 10^2$ | — | $1.3 \pm 0.2 \times 10^4$ |
| PA317 | pBAG | 25–30 | $3.5 \pm 0.2 \times 10^5$ | $8.2 \pm 0.3 \times 10^4$ | NT | NT |
| | PVLMB1 | 20–25 | $1.0 \pm 0.8 \times 10^5$ | $5.3 \pm 0.6 \times 10^4$ | NT | NT |
| | pVLSIB | 25–30 | $3.0 \pm 0.6 \times 10^3$ | $4.6 \pm 1.6 \times 10^2$ | NT | NT |
| | pVLBIRY | 10–15 | $2.3 \pm 0.7 \times 10^3$ | $6.4 \pm 1.6 \times 10^2$ | NT | NT |
| PG13 | pBAG | 20–25 | $2.2 \pm 0.4 \times 10^5$ | — | $3.2 \pm 0.2 \times 10^5$ | — |
| | PVLMB1 | 20–25 | $7.0 \pm 0.6 \times 10^4$ | — | $4.4 \pm 0.5 \times 10^6$ | — |
| | pVLSIB | 20–30 | $2.3 \pm 0.4 \times 10^3$ | — | $1.6 \pm 0.6 \times 10^3$ | — |
| | pVLBIRY | 15–20 | $1.8 \pm 0.6 \times 10^3$ | — | $4.0 \pm 0.4 \times 10^3$ | — |

All experiments were done in triplicate, and most were repeated. Titers are expressed in transducing units/ml supernatant (TU/ml).
Legend:
(—) means not applicable;
NT, not tested;
efficiency (%), percent X-gal positive cells.

What is claimed is:

1. A chimeric viral vector comprising SEQ ID NO: 1.

\* \* \* \* \*

SEQUENCE LISTING

<160> NUMBER OF SEQ ID NOS: 26

<210> SEQ ID NO 1
<211> LENGTH: 9145
<212> TYPE: DNA
<213> ORGANISM: Artificial Sequence
<220> FEATURE:
<223> OTHER INFORMATION: Description of Artificial Sequence: vector
      construct for pVLMB1

<400> SEQUENCE: 1

```
aatgaaagac cccacctgta ggtttggcaa gctagcttaa gtaacgccat tttgcaaggc      60 atgaaaaat acataactga gaatagagaa gttcagatca aggtcaggaa cagatggaac     120
agctgaatat gggccaaaca ggatatctgt ggtaagcagt tcctgccccg gctcagggcc     180
aagaacagat ggaacagctg aatatgggcc aaacaggata tctgtggtaa gcagttcctg     240
ccccggctca gggccaagaa cagatggtcc ccagatgcgg tccagccctc agcagtttct     300
```

-continued

| | | |
|---|---|---|
| agagaaccat cagatgtttc cagggtgccc caaggacctg aaatgaccct gtgccttatt | 360 |
| tgaactaacc aatcagttcg cttctcgctt ctgttcgcgc gcttctgctc cccgagctca | 420 |
| ataaaagagc ccacaacccc tcactcgggg cgccagtcct ccgattgact gagtcgcccg | 480 |
| ggtacccgtg tatccaataa accctcttgc agttgcatcc gacttgtggt ctcgctgttc | 540 |
| cttgggaggg tctcctctga gtgattgact acccgtcagc gggggtcttt catttggggg | 600 |
| ctcgtccggg atcgggagac ccctgcccag ggaccaccga cccaccaccg ggagataagc | 660 |
| tgggtcggag acccctgccc aggaccacc gacccaccac cggggaggtaa gctggccagc | 720 |
| aacttatctg tgtctgtccg attgtctagt gtctatgact gatttatgc gcctgcgtcg | 780 |
| gtactagtta gctaactagc tctgtatctg gcggacccgt ggtggaactg acgagttcgg | 840 |
| aacacccggc cgcaaccctg ggagacgtcc caggaggaac aggggaggat cagggacgcc | 900 |
| tggtggaccc ctttgaaggc caagagacca tttgggggttg cgagatcgtg ggttcgagtc | 960 |
| ccacctcgtg cccagttgcg agatcgtggg ttcgagtccc acctcgtgtt tgttgcgag | 1020 |
| atcgtgggtt cgagtcccac ctcgcgtctg gtcacgggat cgtgggttcg agtcccacct | 1080 |
| cgtgttttgt tgcgagatcg tggggttcgag tcccacctcg cgtctggtca cgggatcgtg | 1140 |
| ggttcgagtc ccacctcgtg cagagggtct caattggccg gccttagaga ggccatctga | 1200 |
| ttcttctggt ttctcttttt gtcttagtct cgtgtccgct cttgttgtga ctactgtttt | 1260 |
| tctaaaaatg ggacaatctg tgtccactcc cctttctctg actctggttc tgtcgcttgg | 1320 |
| taattttgtt tgtttacgtt tgtttttgtg agtcgtctat gttgtctgtt actatcttgt | 1380 |
| ttttgtttgt ggtttacggt ttctgtgtgt gtcttgtgtg tctctttgtg ttcagacttg | 1440 |
| gactgatgac tgacgactgt ttttaagtta tgccttctaa aataagccta aaaatcctgt | 1500 |
| cagatcccta tgctgaccac ttcctttcag atcaacagct gcccttacgt atcgatggat | 1560 |
| ccctcgacta actaatagcc cattctccaa ggtcgagcgg gatcaattcc gcccccccc | 1620 |
| taacgttact ggccgaagcc gcttggaata aggccggtgt gcgtttgtct atatgttatt | 1680 |
| ttccaccata ttgccgtctt ttggcaatgt gagggcccgg aaacctggcc ctgtcttctt | 1740 |
| gacgagcatt cctaggggtc tttcccctct cgccaaagga atgcaaggtc tgttgaatgt | 1800 |
| cgtgaaggaa gcagttcctc tggaagcttc ttgaagacaa acaacgtctg tagcgaccct | 1860 |
| ttgcaggcag cggaaccccc cacctggcga caggtgcctc tgcggccaaa agccacgtgt | 1920 |
| ataagataca cctgcaaagg cggcacaacc ccagtgccac gttgtgagtt ggatagttgt | 1980 |
| ggaaagagtc aaatggctct cctcaagcgt attcaacaag gggctgaagg atgcccagaa | 2040 |
| ggtaccccat tgtatgggat ctgatctggg gcctcggtgc acatgcttta catgtgttta | 2100 |
| gtcgaggtta aaaaaacgtc taggccccc gaaccacggg gacgtggttt tcctttgaaa | 2160 |
| aacacgataa taatcatggg cgcggatccc gtcgttttac aacgtcgtga ctgggaaaac | 2220 |
| cctggcgtta cccaacttaa tcgccttgca gcacatcccc ctttcgccag ctggcgtaat | 2280 |
| agcgaagagg cccgcaccga tcgcccttcc caacagttgc gcagcctgaa tggcgaatgg | 2340 |
| cgctttgcct ggtttccggc accagaagcg gtgccggaaa gctggctgga gtgcgatctt | 2400 |
| cctgaggccg atactgtcgt cgtcccctca aactggcaga tgcacggtta cgatgcgccc | 2460 |
| atctacacca acgtaaccta tcccattacg gtcaatccgc cgtttgttcc cacggagaat | 2520 |
| ccgacgggtt gttactcgct cacatttaat gttgatgaaa gctggctaca ggaaggccag | 2580 |
| acgcgaatta ttttttgatgg cgttaactcg gcgtttcatc tgtggtgcaa cgggcgctgg | 2640 |
| gtcggttacg gccaggacag tcgtttgccg tctgaatttg acctgagcgc attttttacgc | 2700 |

-continued

```
gccggagaaa accgcctcgc ggtgatggtg ctgcgttgga gtgacggcag ttatctggaa    2760
gatcaggata tgtggcggat gagcggcatt ttccgtgacg tctcgttgct gcataaaccg    2820
actacacaaa tcagcgattt ccatgttgcc actcgcttta atgatgattt cagccgcgct    2880
gtactgcagg ctgaagttca gatgtgcggc gagttgcgtg actacctacg ggtaacagtt    2940
tctttatggc agggtgaaac gcaggtcgcc agcggcaccg cgcctttcgg cggtgaaatt    3000
atcgatgagc gtggtggtta tgccgatcgc gtcacactac gtctgaacgt cgaaaacccg    3060
aaactgtgga gcgccgaaat cccgaatctc tatcgtgcgg tggttgaact gcacaccgcc    3120
gacggcacgc tgattgaagc agaagcctgc gatgtcggtt ccgcgaggt gcggattgaa    3180 aatggtctgc tgctgctgaa cggcaagccg ttgctgattc gaggcgttaa ccgtcacgag    3240
catcatcctc tgcatggtca ggtcatggat gagcagacga tggtgcagga tatcctgctg    3300
atgaagcaga acaactttaa cgccgtgcgc tgttcgcatt atccgaacca tccgctgtgg    3360
tacacgctgt gcgaccgcta cggcctgtat gtggtggatg aagccaatat tgaaacccac    3420
ggcatggtgc aatgaatcg tctgaccgat gatccgcgct ggctaccggc gatgagcgaa    3480
cgcgtaacgc gaatggtgca gcgcgatcgt aatcacccga gtgtgatcat ctggtcgctg    3540
gggaatgaat caggccacgg cgctaatcac gacgcgctgt atcgctggat caaatctgtc    3600
gatccttccc gcccggtgca gtatgaaggc ggcggagccg acaccacggc caccgatatt    3660
atttgcccga tgtacgcgcg cgtggatgaa gaccagcccc tcccggctgt gccgaaatgg    3720
tccatcaaaa aatggctttc gctacctgga gagacgcgcc cgctgatcct ttgcgaatac    3780
gcccacgcga tgggtaacag tcttggcggt ttcgctaaat actggcaggc gtttcgtcag    3840
tatccccgtt tacagggcgg cttcgtctgg gactgggtgg atcagtcgct gattaaatat    3900
gatgaaaacg gcaacccgtg gtcggcttac ggcggtgatt ttggcgatac gccgaacgat    3960
cgccagttct gtatgaacgg tctggtcttt gccgaccgca cgccgcatcc agcgctgacg    4020
gaagcaaaac accagcagca gttttttccag ttccgtttat ccgggcaaac catcgaagtg    4080
accagcgaat acctgttccg tcatagcgat aacgagctcc tgcactggat ggtggcgctg    4140
gatggtaagc cgctggcaag cggtgaagtg cctctggatg tcgctccaca aggtaaacag    4200
ttgattgaac tgcctgaact accgcagccg gagagcgccg ggcaactctg gctcacagta    4260
cgcgtagtgc aaccgaacgc gaccgcatgg tcagaagccg ggcacatcag cgcctggcag    4320
cagtggcgtc tggcggaaaa cctcagtgtg acgctccccg ccgcgtccca cgccatcccg    4380
catctgacca ccagcgaaat ggatttttgc atcgagctgg gtaataagcg ttggcaattt    4440
aaccgccagt caggctttct ttcacagatg tggattggcg ataaaaaaca actgctgacg    4500
ccgctgcgcg atcagttcac ccgtgcaccg ctggataacg acattggcgt aagtgaagcg    4560
acccgcattg acctaacgc ctgggtcgaa cgctggaagg cggcgggcca ttaccaggcc    4620
gaagcagcgt tgttgcagtg cacggcagat acacttgctg atgcggtgct gattacgacc    4680
gctcacgcgt ggcagcatca ggggaaaacc ttatttatca gccggaaaac ctaccggatt    4740
gatggtagtg gtcaaatggc gattaccgtt gatgttgaag tggcgagcga tacaccgcat    4800
ccggcgcgga ttgcctgaa ctgccagctg gcgcaggtag cagagcgggt aaactggctc    4860
ggattagggc cgcaagaaaa ctatcccgac cgccttactg ccgcctgttt tgaccgctgg    4920
gatctgccat tgtcagacat gtatacccgg tacgtcttcc cgagcgaaaa cggtctgcgc    4980
tgcgggacgc gcgaattgaa ttatggccca caccagtggc gcggcgactt ccagttcaac    5040
```

```
atcagccgct acagtcaaca gcaactgatg gaaaccagcc atcgccatct gctgcacgcg    5100
gaagaaggca catggctgaa tatcgacggt ttccatatgg ggattggtgg cgacgactcc    5160
tggagcccgt cagtatcggc ggaattccag ctgagcgccg tcgctacca ttaccagttg     5220 gtctggtgtc aaaataata ataaccgggc agggggatc cgaaggcggg gacagcagtg      5280
cagtggtgga cagaaagcaa gtgatctagg ccagcagcct ccctaaaggg acttcagccc    5340
acaaagccaa acttgtggct ttaatacaag ctctgtaaat ggtaaaaaaa aaaagtcta    5400 cacggacagc aggtatgctc ttgccactgt acagagcaat atacagacaa agagaactgt    5460
tgacatctgc agagaaagac ctaagatgct gtggctaaaa gaaatcagat ggcaaatcta    5520
accgcccagg catcctaaag agcaatgatc ctgacagtct gaagactatc aagttataga    5580
caaattaaga ctggtaaaaa aaaccctgta taaaatagta aaaactgaaa aagaaaact     5640 agtcctctca tgagaagaca gacctgcat ctactgaaaa atagacttta ctggaaaaaa    5700
tatgtgtatg aataccttct agttttttgtg aacgttctca agatggataa aagcttttcc   5760
ttgtaaaacg agactgatca gatagtcatc aagaagattg ttaaagaaaa ttttccaagg    5820
ttcggagtgc caaaagcaat agtgtcagat aatggtcctg cctttgttgc ccaggtaagt    5880
cagggtgtgg ccaagtattt agaggtcaaa tgaaaattcc attgtgtgta cagacctcag    5940
agctcaggaa agataaaaaa gaataaataa aactctaaac agaccttgac aaaattaatc    6000
ctagagactg gcacagactt acttggtact ccttcccctt gccctattta gaactgagaa    6060
tactccctct tgattcggtt ttactctttt taagatcctt tatggggctc ctatgccatc    6120
actgtcttaa atgatgtgtt taaacctatg ttgttataat aatgatctat atgttaagtt    6180
aaaaggcttg caggtggtgc agaaagaagt ctggtcacaa ctggctacag tgaacaagct    6240
gggtacccca aggacatctt accagttcca gccagagatc tgatctacga tccccgggtc    6300
gacccgggtc gaccctgtgg aatgtgtgtc agttagggtg tggaaagtcc ccaggctccc    6360
cagcaggcag aagtatgcaa agcatgcatc tcaattagtc agcaaccagg tgtggaaagt    6420
ccccaggctc cccagcaggc agaagtatgc aaagcatgca tctcaattag tcagcaacca    6480
tagtcccgcc cctaactccg cccatcccgc cctaactccc gccagttcc gccattctc     6540 cgccccatgg ctgactaatt tttttatt atgcagaggc cgaggccgcc tcggcctctg      6600
agctattcca gaagtagtga ggaggctttt ttggaggcct aggcttttgc aaaaagcttc    6660
acgctgccgc aagcactcag ggcgcaaggg ctgctaaagg aagcggaaca cgtagaaagc    6720
cagtccgcag aaacggtgct gaccccggat gaatgtcagc tactgggcta tctggacaag    6780
ggaaaacgca agcgcaaaga gaaagcaggt agcttgcagt gggcttacat ggcgatagct    6840
agactgggcg gttttatgga cagcaagcga accggaattg ccagctgggg cgccctctgg    6900
taaggttggg aagcccctgca aagtaaactg gatggctttc ttgccgccaa ggatctgatg    6960
gcgcagggga tcaagatctg atcaagagac aggatgagga tcgtttcgca tgattgaaca    7020
agatggattg cacgcaggtt ctccggccgc ttgggtggag aggctattcg gctatgactg    7080
ggcacaacag acaatcggct gctctgatgc cgccgtgttc cggctgtcag cgcaggggcg    7140
cccggttctt tttgtcaaga ccgacctgtc cggtgccctg aatgaactgc aggacgaggc    7200
agcgcggcta tcgtggctgg ccacgacggg cgttccttgc gcagctgtgc tcgacgttgt    7260
cactgaagcg ggaagggact ggctgctatt gggcgaagtg ccggggcagg atcctcgtc    7320 atctcacctt gctcctgccg agaaagtatc catcatggct gatgcaatgc ggcggctgca    7380
tacgcttgat ccggctacct gcccattcga ccaccaagcg aaacatcgca tcgagcgagc    7440
```

```
acgtactcgg atggaagccg gtcttgtcga tcaggatgat ctggacgaag agcatcaggg    7500
gctcgcgcca gccgaactgt tcgccaggct caaggcgcgc atgcccgacg gcgaggatct    7560
cgtcgtgacc catggcgatg cctgcttgcc gaatatcatg gtggaaaatg gccgcttttc    7620
tggattcatc gactgtggcc ggctgggtgt ggcggaccgc tatcaggaca tagcgttggc    7680
tacccgtgat attgctgaag agcttggcgg cgaatgggct gaccgcttcc tcgtgcttta    7740
cggtatcgcc gctcccgatt cgcagcgcat cgccttctat cgccttcttg acgagttctt    7800
ctgagcggga ctctggggtt cgaaatgacc gaccaagcga cgcccaacct gccatcacga    7860
gatttcgatt ccaccgccgc cttctatgaa aggttgggct tcggaatcgt tttccgggac    7920
ggaattcgta atctgctgct tgcaaacaaa aaaaccaccg ctaccagcgg tggtttgttt    7980
gccggatcaa gagctaccaa ctcttttttcc gaaggtaact ggcttcagca gagcgcagat    8040
accaaatact gtccttctag tgtagccgta gttaggccac cacttcaaga actctgtagc    8100
accgcctaca tacctcgctc tgctaatcct gttaccagtg gctgctgcca gtggcgataa    8160
gtcgtgtctt accgggttgg actcaagacg atagttaccg gataaggcgc agcggtcggg    8220
ctgaacgggg ggttcgtgca cacagcccag cttggagcga acgacctaca ccgaactgag    8280
atacctacag cgtgagcatt gagaaagcgc cacgcttccc gaagggagaa aggcggacag    8340
gtatccggta agcggcaggg tcggaacagg agagcgcacg agggagcttc caggggggaaa    8400 cgcctggtat ctttatagtc ctgtcgggtt tcgccacctc tgacttgagc gtcgattttt    8460
gtgatgctcg tcagggggc ggagcctatg gaaaaacgcc agcaacgccg agatgcgccg    8520
cctcgagaac cctggcccta ttattgggtg gactaaccat gggggggaatt gccgctggaa    8580 taggaacagg gactactgct ctaatggcca ctcagcaatt ccagcagctc caagccgcag    8640
tacaggatga tctcagggag gttgaaaaat caatctctaa cctagaaaag tctctcactt    8700
ccctgtctga agttgtccta cagaatcgaa ggggcctaga cttgttattt ctaaaagaag    8760
gagggctgtg tgctgctcta aaagaagaat gttgcttcta tgcggaccac acaggactag    8820
tgagagacag catggccaaa ttgagagaga ggcttaatca gagacagaaa ctgtttgagt    8880
caactcaagg atggtttgag ggactgttta acagatcccc ttggtttacc accttgatat    8940
ctaccattat gggacccctc attgtactcc taatgatttt gctcttcgga ccctgcattc    9000
ttaatcgatt agtccaattt gttaaagaca ggatatcagt ggtccaggct ctagttttga    9060
ctcaacaata tcaccagctg aagcctatag agtacgagcc atagataaaa taaaagattt    9120
tatttagtct ccagaaaaag ggggg                                          9145
```

```
<210> SEQ ID NO 2
<211> LENGTH: 9093
<212> TYPE: DNA
<213> ORGANISM: Artificial Sequence
<220> FEATURE:
<223> OTHER INFORMATION: Description of Artificial Sequence: vector
      construct for pVLMB2

<400> SEQUENCE: 2
```

```
aatgaaagac cccaccctgta ggtttggcaa gctagcttaa gtaacgccat tttgcaaggc     60
atggaaaaat acataactga gaatagagaa gttcagatca aggtcaggaa cagatggaac    120
agctgaatat gggccaaaca ggatatctgt ggtaagcagt tcctgccccg gctcagggcc    180
aagaacagat ggaacagctg aatatgggcc aaacaggata tctgtggtaa gcagttcctg    240
ccccggctca gggccaagaa cagatggtcc ccagatgcgg tccagccctc agcagtttct    300
```

-continued

```
agagaaccat cagatgtttc cagggtgccc caaggacctg aaatgaccct gtgccttatt    360
tgaactaacc aatcagttcg cttctcgctt ctgttcgcgc gcttctgctc cccgagctca    420
ataaaagagc ccacaacccc tcactcgggg cgccagtcct ccgattgact gagtcgcccg    480
ggtacccgtg tatccaataa accctcttgc agttgcatcc gacttgtggt ctcgctgttc    540
cttgggaggg tctcctctga gtgattgact acccgtcagc ggggtctttt catttggggg    600
ctcgtccggg atcgggagac ccctgcccag ggaccaccga cccaccaccg ggaggtaagc    660
tggccagcaa cttatctgtg tctgtccgat tgtctagtgt ctatgactga ttttatgcgc    720
ctgcgtcggt actagttagc taactagctc tgtatctggc ggacccgtgg tggaactgac    780
gagttcggaa cacccggccg caaccctggg agacgtccca ggaggaacag gggaggatca    840
gggacgcctg gtggacccct ttgaaggcca agagaccatt tggggttgcg agatcgtggg    900
ttcgagtccc acctcgtgcc cagttgcgag atcgtgggtt cgagtcccac ctcgtgtttt    960
gttgcgagat cgtgggttcg agtcccacct cgcgtctggt cacgggatcg tgggttcgag   1020
tcccacctcg tgttttgttg cgagatcgtg ggttcgagtc ccacctcgcg tctggtcacg   1080
ggatcgtggg ttcgagtccc acctcgtgca gagggtctca attggccggc cttagagagg   1140
ccatctgatt cttctggttt ctcttttgt cttagtctcg tgtccgctct tgttgtgact   1200
actgttttc taaaaatggg acaatctgtg tccactcccc tttctctgac tctggttctg   1260
tcgcttggta attttgtttg tttacgtttg ttttgtgag tcgtctatgt tgtctgttac   1320
tatcttgttt ttgtttgtgg tttacggttt ctgtgtgtgt cttgtgtgtc tctttgtgtt   1380
cagacttgga ctgatgactg acgactgttt ttaagttatg ccttctaaaa taagcctaaa   1440
aatcctgtca gatccctatg ctgaccactt cctttcagat caacagctgc ccttacgtat   1500
cgatggatcc ctcgactaac taatagccca ttctccaagg tcgagcggga tcaattccgc   1560
cccccccta acgttactgg ccgaagccgc ttggaataag gccggtgtgc gtttgtctat   1620
atgttatttt ccaccatatt gccgtctttt ggcaatgtga gggcccggaa acctggccct   1680
gtcttcttga cgagcattcc tagggtcttt tcccctctcg ccaaaggaat gcaaggtctg   1740
ttgaatgtcg tgaaggaagc agttcctctg gaagcttctt gaagacaaac aacgtctgta   1800
gcgacccttt gcaggcagcg gaaccccca cctggcgaca ggtgcctctg cggccaaaag   1860
ccacgtgtat aagatacacc tgcaaaggcg gcacaacccc agtgccacgt tgtgagttgg   1920
atagttgtgg aaagagtcaa atggctctcc tcaagcgtat tcaacaaggg gctgaaggat   1980
gcccagaagg tacccattg tatgggatct gatctgggc ctcggtgcac atgctttaca   2040
tgtgtttagt cgaggttaaa aaaacgtcta ggccccccga accacgggga cgtggttttc   2100
ctttgaaaaa cacgataata atcatgggcg cggatcccgt cgttttacaa cgtcgtgact   2160
gggaaaaccc tggcgttacc caacttaatc gccttgcagc acatcccct ttcgccagct   2220
ggcgtaatag cgaagaggcc cgcaccgatc gcccttccca acagttgcgc agcctgaatg   2280
gcgaatggcg ctttgcctgg tttccggcac cagaagcggt gccggaaagc tggctggagt   2340
gcgatcttcc tgaggccgat actgtcgtcg tcccctcaaa ctggcagatg cacggttacg   2400
atgcgcccat ctacaccaac gtaacctatc ccattacggt caatccgccg tttgttccca   2460
cggagaatcc gacgggttgt tactcgctca catttaatgt tgatgaaagc tggctacagg   2520
aaggccagac gcgaattatt tttgatggcg ttaactcggc gtttcatctg tggtgcaacg   2580
ggcgctgggt cggttacggc caggacagtc gtttgccgtc tgaatttgac ctgagcgcat   2640
```

-continued

| | |
|---|---|
| ttttacgcgc cggagaaaac cgcctcgcgg tgatggtgct gcgttggagt gacggcagtt | 2700 |
| atctggaaga tcaggatatg tggcggatga gcggcatttt ccgtgacgtc tcgttgctgc | 2760 |
| ataaaccgac tacacaaatc agcgatttcc atgttgccac tcgctttaat gatgatttca | 2820 |
| gccgcgctgt actggaggct gaagttcaga tgtgcggcga gttgcgtgac tacctacggg | 2880 |
| taacagtttc tttatggcag ggtgaaacgc aggtcgccag cggcaccgcg cctttcggcg | 2940 |
| gtgaaattat cgatgagcgt ggtggttatg ccgatcgcgt cacactacgt ctgaacgtcg | 3000 |
| aaaacccgaa actgtggagc gccgaaatcc gaatctcta tcgtgcggtg gttgaactgc | 3060 |
| acaccgccga cggcacgctg attgaagcag aagcctgcga tgtcggtttc cgcgaggtgc | 3120 |
| ggattgaaaa tggtctgctg ctgctgaacg caagccgtt gctgattcga ggcgttaacc | 3180 |
| gtcacgagca tcatcctctg catggtcagg tcatggatga gcagacgatg gtgcaggata | 3240 |
| tcctgctgat gaagcagaac aactttaacg ccgtgcgctg ttcgcattat ccgaaccatc | 3300 |
| cgctgtggta cacgctgtgc gaccgctacg gcctgtatgt ggtggatgaa gccaatattg | 3360 |
| aaacccacgg catggtgcca atgaatcgtc tgaccgatga tccgcgctgg ctaccggcga | 3420 |
| tgagcgaacg cgtaacgcga atggtgcagc gcgatcgtaa tcacccgagt gtgatcatct | 3480 |
| ggtcgctggg gaatgaatca ggccacggcg ctaatcacga cgcgctgtat cgctggatca | 3540 |
| aatctgtcga tccttcccgc ccggtgcagt atgaaggcgg cggagccgac accacggcca | 3600 |
| ccgatattat ttgcccgatg tacgcgcgcg tggatgaaga ccagcccttc ccggctgtgc | 3660 |
| cgaaatggtc catcaaaaaa tggctttcgc tacctggaga gacgcgcccg ctgatccttt | 3720 |
| gcgaatacgc ccacgcgatg ggtaacagtc ttggcggttt cgctaaatac tggcaggcgt | 3780 |
| tcgtcagta tccccgttta cagggcggct tcgtctggga ctgggtggat cagtcgctga | 3840 |
| ttaaatatga tgaaaacggc aacccgtggt cggcttacgg cggtgatttt ggcgatacgc | 3900 |
| cgaacgatcg ccagttctgt atgaacgtc tggtctttgc cgaccgcacg ccgcatccag | 3960 |
| cgctgacgga agcaaaacac cagcagcagt ttttccagtt ccgtttatcc gggcaaacca | 4020 |
| tcgaagtgac cagcgaatac ctgttccgtc atagcgataa cgagctcctg cactggatgg | 4080 |
| tggcgctgga tggtaagccg ctggcaagcg gtgaagtgcc tctggatgtc gctccacaag | 4140 |
| gtaaacagtt gattgaactg cctgaactac cgcagccgga gagcgccggg caactctggc | 4200 |
| tcacagtacg cgtagtgcaa ccgaacgcga ccgcatggtc agaagccggg cacatcagcg | 4260 |
| cctggcagca gtgcgtctg gcggaaaacc tcagtgtgac gctccccgcc gcgtcccacg | 4320 |
| ccatcccgca tctgaccacc agcgaaatgg attttttgcat cgagctgggt aataagcgtt | 4380 |
| ggcaatttaa ccgccagtca ggctttcttt cacagatgtg gattggcgat aaaaacaac | 4440 |
| tgctgacgcc gctgcgcgat cagttcaccc gtgcaccgct ggataacgac attggcgtaa | 4500 |
| gtgaagcgac ccgcattgac cctaacgcct gggtcgaacg ctggaaggcg gcgggccatt | 4560 |
| accaggccga agcagcgttg ttgcagtgca cggcagatac acttgctgat gcggtgctga | 4620 |
| ttacgaccgc tcacgcgtgg cagcatcagg ggaaaaccct attatcagc cggaaaacct | 4680 |
| accggattga tggtagtggt caaatggcga ttaccgttga tgttgaagtg cgcagcgata | 4740 |
| caccgcatcc ggcgcggatt ggcctgaact gccagctggc gcaggtagca gagcgggtaa | 4800 |
| actggctcgg attagggccg caagaaaact atcccgaccg ccttactgcc gcctgttttg | 4860 |
| accgctggga tctgccattg tcagacatgt atacccgta cgtcttcccg agcgaaaacg | 4920 |
| gtctgcgctg cgggacgcgc gaattgaatt atggcccaca ccagtggcgc ggcgacttcc | 4980 |
| agttcaacat cagccgctac agtcaacagc aactgatgga accagccat cgccatctgc | 5040 |

```
tgcacgcgga agaaggcaca tggctgaata tcgacggttt ccatatgggg attggtggcg    5100
acgactcctg gagcccgtca gtatcggcgg aattccagct gagcgccggt cgctaccatt    5160
accagttggt ctggtgtcaa aataataat aaccgggcag gggggatccg aaggcgggga    5220
cagcagtgca gtggtggaca gaaagcaagt gatctaggcc agcagcctcc ctaaagggac    5280
ttcagcccac aaagccaaac ttgtggcttt aatacaagct ctgtaaatgg taaaaaaaa    5340 aaagtctaca cggacagcag gtatgctctt gccactgtac agagcaatat acagacaaag    5400
agaactgttg acatctgcag agaaagacct aagatgctgt ggctaaaaga atcagatgg    5460 caaatctaac cgcccaggca tcctaaagag caatgatcct gacagtctga agactatcaa    5520
gttatagaca aattaagact ggtaaaaaaa accctgtata aaatagtaaa aactgaaaaa    5580
agaaaactag tcctctcatg agaagacaga cctgacatct actgaaaaat agactttact    5640
ggaaaaaata tgtgtatgaa taccttctag tttttgtgaa cgttctcaag atggataaaa    5700
gcttttcctt gtaaaacgag actgatcaga tagtcatcaa gaagattgtt aaagaaaatt    5760
ttccaaggtt cggagtgcca aaagcaatag tgtcagataa tggtcctgcc tttgttgccc    5820
aggtaagtca gggtgtggcc aagtatttag aggtcaaatg aaaattccat tgtgtgtaca    5880
gacctcagag ctcaggaaag ataaaaaaga ataaataaaa ctctaaacag accttgacaa    5940
aattaatcct agagactggc acagacttac ttggtactcc ttccccttgc cctatttaga    6000
actgagaata ctccctcttg attcggtttt actctttta agatccttta tggggctcct    6060
atgccatcac tgtcttaaat gatgtgttta aacctatgtt gttataataa tgatctatat    6120
gttaagttaa aaggcttgca ggtggtgcag aaagaagtct ggtcacaact ggctacagtg    6180
aacaagctgg gtaccccaag gacatcttac cagttccagc cagagatctg atctacgatc    6240
cccgggtcga cccgggtcga ccctgtggaa tgtgtgtcag ttagggtgtg aaaagtcccc    6300
aggctcccca gcaggcagaa gtatgcaaag catgcatctc aattagtcag caaccaggtg    6360
tggaaagtcc ccaggctccc cagcaggcag aagtatgcaa agcatgcatc tcaattagtc    6420
agcaaccata gtcccgcccc taactccgcc catcccgccc ctaactccgc ccagttccgc    6480
ccattctccg ccccatggct gactaatttt ttttatttat gcagaggccg aggccgcctc    6540
ggcctctgag ctattccaga agtagtgagg aggcttttt ggaggcctag gcttttgcaa    6600
aaagcttcac gctgccgcaa gcactcaggg cgcaagggct gctaaaggaa gcggaacacg    6660
tagaaagcca gtccgcagaa acggtgctga ccccggatga atgtcagcta ctgggctatc    6720
tggacaaggg aaaacgcaag cgcaaagaga agcaggtag cttgcagtgg gcttacatgg    6780
cgatagctag actgggcggt tttatggaca gcaagcgaac cggaattgcc agctggggcg    6840
ccctctggta aggttgggaa gccctgcaaa gtaaactgga tggctttctt gccgccaagg    6900
atctgatggc gcagggatc aagatctgat caagagacag gatgaggatc gtttcgcatg    6960
attgaacaag atggattgca cgcaggttct ccggccgctt gggtggagag gctattcggc    7020
tatgactggg cacaacagac aatcggctgc tctgatgccg ccgtgttccg gctgtcagcg    7080
caggggcgcc cggttctttt tgtcaagacc gacctgtccg gtgccctgaa tgaactgcag    7140
gacgaggcag cgcggctatc gtggctggcc acgacgggc ttccttgcgc agctgtgctc    7200
gacgttgtca ctgaagcggg aagggactgg ctgctattgg gcgaagtgcc ggggcaggat    7260
ctcctgtcat ctcaccttgc tcctgccgag aaagtatcca tcatggctga tgcaatgcgg    7320
cggctgcata cgcttgatcc ggctacctgc ccattcgacc accaagcgaa acatcgcatc    7380
```

-continued

```
gagcgagcac gtactcggat ggaagccggt cttgtcgatc aggatgatct ggacgaagag      7440 catcagggc tcgcgccagc cgaactgttc gccaggctca aggcgcgcat gcccgacggc      7500
gaggatctcg tcgtgaccca tggcgatgcc tgcttgccga atatcatggt ggaaaatggc     7560
cgcttttctg gattcatcga ctgtggccgg ctgggtgtgg cggaccgcta tcaggacata     7620
gcgttggcta cccgtgatat tgctgaagag cttggcggcg aatgggctga ccgcttcctc     7680
gtgctttacg gtatcgccgc tcccgattcg cagcgcatcg ccttctatcg ccttcttgac     7740
gagttcttct gagcgggact ctggggttcg aaatgaccga ccaagcgacg cccaacctgc     7800
catcacgaga tttcgattcc accgccgcct tctatgaaag gttgggcttc ggaatcgttt     7860
tccgggacgg aattcgtaat ctgctgcttg caaacaaaaa aaccaccgct accagcggtg     7920
gtttgtttgc cggatcaaga gctaccaact cttttccga aggtaactgg cttcagcaga      7980
gcgcagatac caaatactgt ccttctagtg tagccgtagt taggccacca cttcaagaac     8040
tctgtagcac cgcctacata cctcgctctg ctaatcctgt taccagtggc tgctgccagt     8100
ggcgataagt cgtgtcttac cgggttggac tcaagacgat agttaccgga taaggcgcag    8160
cggtcgggct gaacggggg ttcgtgcaca cagcccagct tggagcgaac gacctacacc     8220
gaactgagat acctacagcg tgagcattga gaaagcgcca cgcttcccga agggagaaag    8280
gcggacaggt atccggtaag cggcagggtc ggaacaggag agcgcacgag ggagcttcca    8340
gggggaaacg cctggtatct ttatagtcct gtcgggtttc gccacctctg acttgagcgt     8400
cgatttttgt gatgctcgtc aggggggcgg agcctatgga aaaacgccag caacgccgag    8460
atgcgccgcc tcgagaaccc tggcctatt attgggtgga ctaaccatgg ggggaattgc     8520
cgctggaata ggaacaggga ctactgctct aatggccact cagcaattcc agcagctcca    8580
agccgcagta caggatgatc tcagggaggt tgaaaatca atctctaacc tagaaaagtc     8640
tctcacttcc ctgtctgaag ttgtcctaca gaatcgaagg ggcctagact tgttatttct    8700
aaaagaagga gggctgtgtg ctgctctaaa agaagaatgt tgcttctatg cggaccacac    8760
aggactagta agagacagca tggccaaatt gagagagagg cttaatcaga gacagaaact    8820
gtttgagtca actcaaggat ggtttgaggg actgttaac agatcccctt ggtttaccac     8880
cttgatatct accattatgg gacccctcat tgtactccta atgattttgc tcttcggacc    8940
ctgcattctt aatcgattag tccaatttgt taaagacagg atatcagtgg tccaggctct   9000
agttttgact caacaatatc accagctgaa gcctatagag tacgagccat agataaaata    9060 aaagattta tttagtctcc agaaaaggg ggg                                    9093
```

<210> SEQ ID NO 3
<211> LENGTH: 8574
<212> TYPE: DNA
<213> ORGANISM: Artificial Sequence
<220> FEATURE:
<223> OTHER INFORMATION: Description of Artificial Sequence: vector construct for pVLMB3

<400> SEQUENCE: 3

```
aatgaaagac cccacctgta ggtttggcaa gctagcttaa gtaacgccat tttgcaaggc       60
atggaaaaat acataactga gaatagaaa gttcagatca aggtcaggaa cagatggaac      120
agctgaatat gggccaaaca ggatatctgt ggtaagcagt tcctgccccg gctcagggcc     180
aagaacagat ggaacagctg aatatgggcc aaacaggata tctgtggtaa gcagttcctg    240
ccccggctca gggccaagaa cagatggtcc ccagatgcgg tccagccctc agcagtttct    300
```

-continued

| | |
|---|---|
| agagaaccat cagatgtttc cagggtgccc caaggacctg aaatgaccct gtgccttatt | 360 |
| tgaactaacc aatcagttcg cttctcgctt ctgttcgcgc gcttctgctc cccgagctca | 420 |
| ataaaagagc ccacaacccc tcactcgggg cgccagtcct ccgattgact gagtcgcccg | 480 |
| ggtacccgtg tatccaataa accctcttgc agttgcatcc gacttgtggt ctcgctgttc | 540 |
| cttgggaggg tctcctctga gtgattgact acccgtcagc gggggtcttt catttggggg | 600 |
| ctcgtccggg atcgggagac ccctgcccag ggaccaccga cccaccaccg ggagataagc | 660 |
| tgggtcggag acccctgccc agggaccacc gacccaccac cgggaggtaa gctgccagc | 720 |
| aacttatctg tgtctgtccg attgtctagt gtctatgact gattttatgc gcctgcgtcg | 780 |
| gtactagtta gctaactagc tctgtatctg gcggacccgt ggtggaactg acgagttcgg | 840 |
| aacacccggc cgcaaccctg ggagacgtcc caggaggaac aggggaggat cagggacgcc | 900 |
| tggtggaccc ctttgaaggc caagagacca tttggggttg cgagatcgtg ggttcgagtc | 960 |
| ccaccatcga tggttacgta tcgatggatc cctcgactaa ctaatagccc attctccaag | 1020 |
| gtcgagcggg atcaattccg cccccccct aacgttactg gccgaagccg cttggaataa | 1080 |
| ggccggtgtg cgtttgtcta tatgttattt tccaccatat tgccgtcttt tggcaatgtg | 1140 |
| agggcccgga aacctggccc tgtcttcttg acgagcattc ctaggggtct ttcccctctc | 1200 |
| gccaaaggaa tgcaaggtct gttgaatgtc gtgaaggaag cagttcctct ggaagcttct | 1260 |
| tgaagacaaa caacgtctgt agcgacccct tgcaggcagc ggaaccccc acctggcgac | 1320 |
| aggtgcctct gcggccaaaa gccacgtgta taagatacac ctgcaaaggc ggcacaaccc | 1380 |
| cagtgccacg ttgtgagttg gatagttgtg gaaagagtca aatggctctc ctcaagcgta | 1440 |
| ttcaacaagg ggctgaagga tgcccagaag gtaccccatt gtatgggatc tgatctgggg | 1500 |
| cctcggtgca catgctttac atgtgtttag tcgaggttaa aaaacgtct aggcccccg | 1560 |
| aaccacgggg acgtggtttt cctttgaaaa acacgataat aatcatgggc gcggatcccg | 1620 |
| tcgttttaca acgtcgtgac tgggaaaacc ctggcgttac ccaacttaat cgccttgcag | 1680 |
| cacatccccc tttcgccagc tggcgtaata gcgaagaggc ccgcaccgat cgcccttccc | 1740 |
| aacagttgcg cagcctgaat ggcgaatggc gctttgcctg gtttccggca ccagaagcgg | 1800 |
| tgccggaaag ctggctggag tgcgatcttc ctgaggccga tactgtcgtc gtccctcaa | 1860 |
| actggcagat gcacggttac gatgcgccca tctacaccaa cgtaacctat cccattacgg | 1920 |
| tcaatccgcc gtttgttccc acggagaatc cgacgggttg ttactcgctc acatttaatg | 1980 |
| ttgatgaaag ctggctacag gaaggccaga cgcgaattat ttttgatggc gttaactcgg | 2040 |
| cgtttcatct gtggtgcaac gggcgctggg tcggttacgg ccaggacagt cgtttgccgt | 2100 |
| ctgaatttga cctgagcgca ttttacgcg ccggagaaaa ccgcctcgcg gtgatggtgc | 2160 |
| tgcgttggag tgacggcagt tatctggaag atcaggatat gtggcggatg agcggcattt | 2220 |
| tccgtgacgt ctcgttgctg cataaaccga ctacacaaat cagcgatttc catgttgcca | 2280 |
| ctcgctttaa tgatgatttc agccgcgctg tactggaggc tgaagttcag atgtgcggcg | 2340 |
| agttgcgtga ctacctacgg gtaacagttt ctttatggca gggtgaaacg caggtcgcca | 2400 |
| gcggcaccgc gcctttcggc ggtgaaatta tcgatgagcg tggtggttat gccgatcgcg | 2460 |
| tcacactacg tctgaacgtc gaaaacccga aactgtggag cgccgaaatc cgaatctct | 2520 |
| atcgtgcggt ggttgaactg cacaccgccg acggacgct gattgaagca gaagcctgcg | 2580 |
| atgtcggttt ccgcgaggtg cggattgaaa atggtctgct gctgctgaac ggcaagccgt | 2640 |
| tgctgattcg aggcgttaac cgtcacgagc atcatcctct gcatggtcag gtcatggatg | 2700 |

-continued

```
agcagacgat ggtgcaggat atcctgctga tgaagcagaa caactttaac gccgtgcgct  2760
gttcgcatta tccgaaccat ccgctgtggt acacgctgtg cgaccgctac ggcctgtatg  2820
tggtggatga agccaatatt gaaacccacg gcatggtgcc aatgaatcgt ctgaccgatg  2880
atccgcgctg gctaccggcg atgagcgaac gcgtaacgcg aatggtgcag cgcgatcgta  2940
atcacccgag tgtgatcatc tggtcgctgg ggaatgaatc aggccacggc gctaatcacg  3000
acgcgctgta tcgctggatc aaatctgtcg atccttcccg cccggtgcag tatgaaggcg  3060
gcggagccga caccacggcc accgatatta tttgcccgat gtacgcgcgc gtggatgaag  3120
accagccctt cccggctgtg ccgaaatggt ccatcaaaaa atggctttcg ctacctggag  3180
agacgcgccc gctgatcctt tgcgaatacg cccacgcgat gggtaacagt cttggcggtt  3240
tcgctaaata ctggcaggcg tttcgtcagt atccccgttt acagggcggc ttcgtctggg  3300
actgggtgga tcagtcgctg attaaatatg atgaaaacgg caacccgtgg tcggcttacg  3360
gcggtgattt tggcgatacg ccgaacgatc gccagttctg tatgaacggt ctggtctttg  3420
ccgaccgcac gccgcatcca gcgctgacgg aagcaaaaca ccagcagcag tttttccagt  3480
tccgtttatc cgggcaaacc atcgaagtga ccagcgaata cctgttccgt catagcgata  3540
acgagctcct gcactggatg gtggcgctgg atggtaagcc gctggcaagc ggtgaagtgc  3600
ctctggatgt cgctccacaa ggtaaacagt tgattgaact gcctgaacta ccgcagccgg  3660
agagcgccgg gcaactctgg ctcacagtac gcgtagtgca accgaacgcg accgcatggt  3720
cagaagccgg gcacatcagc gcctggcagc agtggcgtct ggcggaaaac ctcagtgtga  3780
cgctcccgc cgcgtcccac gccatcccgc atctgaccac cagcgaaatg gattttgca  3840
tcgagctggg taataagcgt tggcaattta accgccagtc aggctttctt tcacagatgt  3900
ggattggcga taaaaaacaa ctgctgacgc cgctgcgcga tcagttcacc cgtgcaccgc  3960
tggataacga cattggcgta agtgaagcga cccgcattga ccctaacgcc tgggtcgaac  4020
gctggaaggc ggcgggccat taccaggccg aagcagcgtt gttgcagtgc acggcagata  4080
cacttgctga tgcggtgctg attacgaccg ctcacgcgtg gcagcatcag gggaaaacct  4140
tatttatcag ccgaaaaacc taccggattg atggtagtgg tcaaatggcg attaccgttg  4200
atgttgaagt ggcgagcgat acaccgcatc cggcgcggat tggcctgaac tgccagctgg  4260
cgcaggtagc agagcgggta aactggctcg gattagggcc gcaagaaaac tatcccgacc  4320
gccttactgc cgcctgtttt gaccgctggg atctgccatt gtcagacatg tatacccgt  4380
acgtcttccc gagcgaaaac ggtctgcgct gcgggacgcg cgaattgaat tatggcccac  4440
accagtggcg cggcgacttc cagttcaaca tcagccgcta cagtcaacag caactgatgg  4500
aaaccagcca tcgccatctg ctgcacgcgg aagaaggcac atggctgaat atcgacggtt  4560
tccatatggg gattggtggc gacgactcct ggagcccgtc agtatcggcg gaattccagc  4620
tgagcgccgg tcgctaccat taccagttgg tctggtgtca aaaataataa taaccgggca  4680
gggggggatcc gaaggcgggg acagcagtgc agtggtggca agaaagcaag tgatctaggc  4740
cagcagcctc cctaaaggga cttcagccca caaagccaaa cttgtggctt taatacaagc  4800
tctgtaaatg gtaaaaaaaa aaagtctac acggacagca ggtatgctct tgccactgta  4860
cagagcaata tacagacaaa gagaactgtt gacatctgca gagaaagacc taagatgctg  4920
tggctaaaag aaatcagatg gcaaatctaa ccgcccaggc atcctaaaga gcaatgatcc  4980
tgacagtctg aagactatca agttatagac aaattaagac tggtaaaaaa aaccctgtat  5040
```

```
aaaatagtaa aaactgaaaa aagaaaacta gtcctctcat gagaagacag acctgacatc    5100
tactgaaaaa tagactttac tggaaaaaat atgtgtatga ataccttcta gttttttgtga   5160 acgttctcaa gatggataaa agcttttcct tgtaaaacga gactgatcag atagtcatca   5220
agaagattgt taaagaaaat tttccaaggt tcggagtgcc aaaagcaata gtgtcagata   5280
atggtcctgc ctttgttgcc caggtaagtc agggtgtggc caagtattta gaggtcaaat   5340
gaaaattcca ttgtgtgtac agacctcaga gctcaggaaa gataaaaaag aataaataaa   5400
actctaaaca gaccttgaca aaattaatcc tagagactgg cacagactta cttggtactc   5460
cttccccttg ccctatttag aactgagaat actccctctt gattcggttt tactcttttt   5520
aagatccttt atgggctccc tatgccatca ctgtcttaaa tgatgtgttt aaacctatgt   5580
tgttataata atgatctata tgttaagtta aaaggcttgc aggtggtgca gaaagaagtc   5640
tggtcacaac tggctacagt gaacaagctg ggtaccccaa ggacatctta ccagttccag   5700
ccagagatct gatctacgat ccccgggtcg acccgggtcg accctgtgga atgtgtgtca   5760
gttagggtgt ggaaagtccc caggctcccc agcaggcaga agtatgcaaa gcatgcatct   5820
caattagtca gcaaccaggt gtggaaagtc cccaggctcc ccagcaggca agtatgca    5880 aagcatgcat ctcaattagt cagcaaccat agtcccgccc ctaactccgc ccatcccgcc   5940
cctaactccg cccagttccg cccattctcc gccccatggc tgactaattt ttttttattta  6000 tgcagaggcc gaggccgcct cggcctctga gctattccag aagtagtgag gaggcttttt   6060
tggaggccta ggcttttgca aaaagcttca cgctgccgca agcactcagg cgcaagggc    6120 tgctaaagga agcggaacac gtagaaagcc agtccgcaga aacggtgctg accccggatg   6180
aatgtcagct actgggctat ctggacaagg gaaaacgcaa gcgcaaagag aaagcaggta   6240
gcttgcagtg ggcttacatg gcgatagcta gactgggcgg tttatggac agcaagcgaa    6300 ccggaattgc cagctgggc gccctctggt aaggttggga agccctgcaa agtaaactgg    6360
atggctttct gccgccaag gatctgatgg cgcagggat caagatctga tcaagagaca    6420
ggatgaggat cgtttcgcat gattgaacaa gatggattgc acgcaggttc tccggccgct   6480
tgggtggaga ggctattcgg ctatgactgg gcacaacaga caatcggctg ctctgatgcc   6540
gccgtgttcc ggctgtcagc gcaggggcgc ccggttcttt ttgtcaagac cgacctgtcc   6600
ggtgccctga atgaactgca ggacgaggca gcgcggctat cgtggctggc cacgacgggc   6660
gttccttgcg cagctgtgct cgacgttgtc actgaagcgg gaagggactg gctgctattg   6720
ggcgaagtgc cggggcagga tctcctgtca tctcaccttg ctcctgccga gaaagtatcc   6780
atcatggctg atgcaatgcg gcggctgcat acgcttgatc cggctacctg cccattcgac   6840
caccaagcga aacatcgcat cgagcgagca cgtactcgga tggaagccgg tcttgtcgat   6900
caggatgatc tggacgaaga gcatcagggg ctcgcgccag ccgaactgtt cgccaggctc   6960
aaggcgcgca tgcccgacgg cgaggatctc gtcgtgaccc atggcgatgc ctgcttgccg   7020
aatatcatgg tggaaaatgg ccgcttttct ggattcatcg actgtggccg ctgggtgtg    7080 gcggaccgct atcaggacat agcgttggct acccgtgata ttgctgaaga gcttggcggc   7140
gaatgggctg accgcttcct cgtgctttac ggtatcgccg ctcccgattc gcagcgcatc   7200
gccttctatc gccttcttga cgagttcttc tgagcggac tctgggttc gaaatgaccg    7260 accaagcgac gcccaacctg ccatcacgag atttcgattc caccgccgcc ttctatgaaa   7320
ggttgggctt cggaatcgtt ttccgggacg gaattcgtaa tctgctgctt gcaaacaaaa   7380
aaaccaccgc taccagcggt ggtttgtttg ccggatcaag agctaccaac tcttttttccg   7440
```

```
aaggtaactg gcttcagcag agcgcagata ccaaatactg tccttctagt gtagccgtag    7500
ttaggccacc acttcaagaa ctctgtagca ccgcctacat acctcgctct gctaatcctg    7560
ttaccagtgg ctgctgccag tggcgataag tcgtgtctta ccgggttgga ctcaagacga    7620
tagttaccgg ataaggcgca gcggtcgggc tgaacggggg gttcgtgcac acagcccagc    7680
ttggagcgaa cgacctacac cgaactgaga tacctacagc gtgagcattg agaaagcgcc    7740
acgcttcccg aagggagaaa ggcggacagg tatccggtaa gcggcagggt cggaacagga    7800
gagcgcacga gggagcttcc aggggaaac gcctggtatc tttatagtcc tgtcgggttt    7860
cgccacctct gacttgagcg tcgattttg tgatgctcgt caggggggcg gagcctatgg    7920
aaaaacgcca gcaacgccga gatgcgccgc ctcgagaacc ctggccctat tattgggtgg    7980
actaaccatg gggggaattg ccgctggaat aggaacaggg actactgctc taatggccac    8040
tcagcaattc cagcagctcc aagccgcagt acaggatgat ctcagggagg ttgaaaaatc    8100
aatctctaac ctagaaaagt ctctcacttc cctgtctgaa gttgtcctac agaatcgaag    8160
gggcctagac ttgttatttc taaaagaagg agggctgtgt gctgctctaa agaagaatg    8220 ttgcttctat gcggaccaca caggactagt gagagacagc atggccaaat tgagagagag    8280
gcttaatcag agacagaaac tgtttgagtc aactcaagga tggtttgagg gactgtttaa    8340
cagatcccct tggtttacca ccttgatatc taccattatg ggacccctca ttgtactcct    8400
aatgattttg ctcttcggac cctgcattct taatcgatta gtccaatttg ttaaagacag    8460
gatatcagtg gtccaggctc tagttttgac tcaacaatat caccagctga agcctataga    8520
gtacgagcca tagataaaat aaaagatttt atttagtctc cagaaaaagg gggg    8574
```

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 4
cacccagagg tcctagaccc accaccggga ggcaagccgg ccgg                      44

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 5
tccaaccacg cttgggacgt ctcccagggc tgcggggag aa                         42

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 6
gattccagct cttcgtaatc tgctgcttgc aaacaaaaaa accacc                    46

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 7
gattccagct cttcatctgg cgttgctggc gtttttccat agg         43

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 8
gattccagct cttccagagc atgcctgcag gtcgactcta gagga         45

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 9
gattccagct cttcaccgtt cccggccaat gcaccaaatg aa         42

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 10
gattccagct cttctcggga gacccctgcc cagggacca         39

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 11
gattccagct cttcacgtct cccaggggttg cggccgggt         39

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: oligonucleotide primer

<400> SEQUENCE: 12
gattccagct cttcgacgtc ccaggaggaa caggggatca         40

<210> SEQ ID NO 13

```
<211> LENGTH: 35
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 13
gattccagct cttcgtccag atcatcctga tcgac                          35

<210> SEQ ID NO 14
<211> LENGTH: 46
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 14
gattccagct cttcaggacg aggagcatca ggggctcgcg ccagcc              46

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 15
gattccagct cttcagcaat atcacgggta gccaac                         36

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 16
gattccagct cttcttgctg aggagcttgg cggcgaatgg gctgaccg            48

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 17
gattccagct cttcagacaa ataattctaa tcttagaatt tcagaagtct agcg      54

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 18
gattccagct cttcggtcga gcgggatcaa ttccgcccc                      39

<210> SEQ ID NO 19
<211> LENGTH: 45
```

```
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 19
gattccagct cttctgcccg gttattatta tttttgacac cagac          45

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 20
gattccagct cttcaggctg aaattctaag attagaatta tttacaagaa gaa          53

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence:
      oligonucleotide primer

<400> SEQUENCE: 21
gattccagct cttcagggag accggaattc gagctcggta cc          42

<210> SEQ ID NO 22
<211> LENGTH: 677
<212> TYPE: DNA
<213> ORGANISM: Murine leukemia virus

<400> SEQUENCE: 22
tcccaggagg aacaggggag gatcagggac gcctggtgga cccctttgaa ggccaagaga          60
ccatttgggg ttgcgagatc gtgggttcga gtcccacctc gtgcccagtt gcagatcgt         120 gggttcgagt cccacctcgt gttttgttgc gagatcgtgg gttcgagtcc cacctcgcgt        180
ctggtcacgg gatcgtgggt tcgagtccca cctcgtgttt tgttgcgaga tcgtgggttc        240
gagtcccacc tcgcgtctgg tcacgggatc gtgggttcga gtcccacctc gtgcagaggg        300
tctcaattgg ccggccttag agaggccatc tgattcttct ggtttctctt tttgtcttag        360
tctcgtgtcc gctcttgttg tgactactgt ttttctaaaa atgggacaat ctgtgtccac        420 tccccttttct ctgactctgg ttctgtcgct tggtaatttt gtttgtttac gtttgttttt      480
gtgagtcgtc tatgttgtct gttactatct tgttttttgtt tgtggtttac ggtttctgtg       540
tgtgtcttgt gtgtctcttt gtgttcagac ttggactgat gactgacgac tgttttttaag      600 ttatgccttc taaaataagc ctaaaaatcc tgtcagatcc ctatgctgac cacttccttt       660
cagatcaaca gctgccc                                                       677

<210> SEQ ID NO 23
<211> LENGTH: 222
<212> TYPE: DNA
<213> ORGANISM: Murine leukemia virus

<400> SEQUENCE: 23
tttgggggct cgtccgggat cgggagaccc ctgcccaggg accaccgacc caccaccggg          60
aggtaagctg gccagcaact tatctgtgtc tgtccgattg tctagtgtct atgactgatt        120
```

```
ttatgcgcct gcgtcggtac tagttagcta actagctctg tatctggcgg acccgtggtg    180
gaactgacga gttcggaaca cccggccgca accctgggag ac                      222
```

<210> SEQ ID NO 24
<211> LENGTH: 678
<212> TYPE: DNA
<213> ORGANISM: Murine leukemia virus

<400> SEQUENCE: 24

```
gtcccaggag gaacagggga ggatcaggga cgcctggtgg accccttga  aggccaagag    60
accatttggg gttgcgagat cgtgggttcg agtcccacct cgtgcccagt tgcgagatcg   120
tgggttcgag tccacctcg  tgttttgttg cgagatcgtg ggttcgagtc ccacctcgcg   180
tctggtcacg ggatcgtggg ttcgagtccc acctcgtgtt tgttgcgag  atcgtgggtt   240
cgagtcccac ctcgcgtctg gtcacgggat cgtgggttcg agtcccacct cgtgcagagg   300
gtctcaattg gccggcctta gagaggccat ctgattcttc tggtttctct ttttgtctta   360
gtctcgtgtc cgctcttgtt gtgactactg tttttctaaa aatgggacaa tctgtgtcca   420
ctccccttc  tctgactctg gttctgtcgc ttggtaattt tgtttgttta cgtttgtttt   480
tgtgagtcgt ctatgttgtc tgttactatc ttgttttttgt ttgtggttta cggtttctgt   540
gtgtgtcttg tgtgtctctt tgtgttcaga cttggactga tgactgacga ctgtttttaa   600
gttatgcctt ctaaaataag cctaaaaatc ctgtcagatc cctatgctga ccacttcctt   660
tcagatcaac agctgccc                                                  678
```

<210> SEQ ID NO 25
<211> LENGTH: 8332
<212> TYPE: RNA
<213> ORGANISM: Murine leukemia virus

<400> SEQUENCE: 25

```
gcgccagucc uccgauugac ugagucgccc ggguacccgu guauccaaua aacccucuug    60
caguugcauc cgacuugugg ucucgcuguu ccuugggagg gucuccucug agugauugac   120
uacccgucag cggggucuu  ucauuugggg gcucgccgg  gaucgggaga ccccugccca   180
gggaccaccg acccaccacc gggagguaag cuggccagca acuuaucugu gucuguccga   240
uugucuagug ucuaugacug auuuuaugcg ccugcgucgg uacuaguuag cuaacuagcu   300
cuguaucugg cggacccgug guggaacuga cgaguucgga acaccggcc  gcaacccugg   360
gagacgucc  aggacuucg  ggggccguuu ugugggcccg accugagucc aaaaauccccg   420
aucguuuugg acucuuuggu gcaccccccu uagaggaggg auaugugguu cugguaggag   480
acgagaaccu aaaacaguuc cgccuccgu  cugaauuuuu gcuuucgguu ugggaccgaa   540
gccgcgccgc gcgucuuguc ugcugcagca ucguucugu  uugucucugu cugacugugu   600
uucuguauuu gucugagaau augggccaga cuguuaccac ucccuuaagu uugaccuuag   660
gucacuggaa agaugucgag cggaucgcuc acaaccaguc gguagaugue aagaagagac   720
guuggguuac cuucugcucu gcagaauggc caaccuuuaa cgucggaugg ccgcgagacg   780
gcaccuuuaa ccgagaccuc aucacccagg uuaagaucaa ggucuuuuca ccuggccgc   840
auggacaccc agaccaggu  cccuacaucg ugaccuggga agccuuggcu uugaccccc   900
cucccugggu caagcccuuu guacaccua  agccucgcc  uccucuuccu ccauccgcc   960
cgcucucccc ccuugaaccu ccucguucga ccccgccucg auccucccuu uauccagccc  1020
```

-continued

```
ucacuccuuc ucuaggcgcc aaaccuaaac cucaaguucu uucugacagu gggggccgc      1080
ucaucgaccu acuuacagaa gacccccgc cuuauaggga cccaagacca cccccuuccg      1140
acagggacgg aaauggugga gaagcgaccc cugcgggaga ggcaccggac ccccuccccaa    1200
uggcaucucg ccuacguggg agacgggagc ccccugugc cgacuccacu accucgcagg      1260
cauuccccu ccgcgcagga ggaaacggac agcuucaaua cuggccguuc uccucuucug      1320
accuuuacaa cuggaaaaau aauaacccuu cuuuucuga agauccaggu aaacugacag      1380
cucugaucga gucuguucuc aucacccauc agcccaccug ggacgacugu cagcagcugu    1440
uggggacucu gcugaccgga gaagaaaaac aacggugcu cuuagaggcu agaaaggcgg      1500
ugcggggcga ugaugggcgc cccacucaac ugcccaauga agucgaugcc gcuuuucccc    1560
ucgagcgccc agacugggau uacaccaccc aggcagguag gaaccaccua guccacuauc    1620
gccaguugcu ccuagcgggu ucccaaaacg cgggcagaag ccccaccaau uggccaagg     1680
uaaaaggaau aacacaaggg cccaaugagu cucccucggc cuuccuagag agacuuaagg    1740
aagccuaucg cagguacacu ccuuaugacc cugaggaccc agggcaagaa acuaaugugu    1800
cuaugucuuu cauuuggcag ucugccccag acauuggag aaaguuagag agguuagaag     1860
auuuaaaaaa caagacgcuu ggagauuugg uuagagaggc agaaaagauc uuuaauaaac    1920
gagaaacccc ggaagaaaga gaggaacgua ucaggagaga aacagaggaa aaagaagaac    1980
gccguaggac agaggaugag cagaaagaga aagaaagaga ucguaggaga cauagagaga    2040
ugagcaagcu auuggccacu gucguuagug gacagaaaca ggauagacag ggaggagaac    2100
gaaggagguc ccaacucgau cgcgaccagu gugccuacug caaagaaaag gggcacuggg    2160
cuaaagauug ucccaagaaa ccacgaggac cucgggggacc aagaccccag accucccucc   2220
ugacccuaga ugacuaggga ggucagagguc aggagccccc cccugaaccc aggauaaccc   2280
ucaaagucgg gggcaaccc gucaccuucc ugguagauac uggggcccaa cacuccgugc     2340
ugacccaaaa uccuggaccc cuaagugaua agucugccug gguccaaggg gcuacuggag    2400
gaaagcggua ucgcuggacc acggaucgca aaguacaucu agcuaccggu aaggucaccc    2460
acucuuuccu ccauguacca gacugucccu auccucuguu aggaagagau uugcugacua    2520
aacuaaaagc ccaaauccac uuugaggau caggagcuca gguuauggga ccaauggggc     2580
agccccugca aguguugacc cuaaauauag aagaugagca ucggcuacau gagaccucaa    2640
aagagccaga uguuucucua gguccacau ggcugcuca uuuccucag gccugggcgg       2700
aaaccgggg caugggacug gcaguucgcc aagcucccucu gaucauaccu cugaaagcaa    2760
ccucuacccc cguguccaua aaacaauacc ccaugucaca agaagccaga cugggggauca  2820
agccccacau acagagacug uuggaccagg gaauacuggu acccugccag uccccccugga  2880
acacgccccu gcuaccgguu aagaaaccag ggacuaauga uuuauaggccu guccaggauc   2940
ugagagaagu caacaagcgg guggaagaca uccacccac cgugcccaac ccuuacaacc    3000
ucuugagcgg gcucccaccg ucccaccagu gguacacugu gcuugauuua aaggaugccu   3060
uuuucugccu gagacuccac cccaccaguc agccucucuu cgccuuugag uggagagauc    3120
cagagauggg aaucucagga caauugaccu ggaccagacu cccacagggu ucaaaaaaca    3180
gucccacccu guuugaugag gcacugcaca gagaccuagc agacuuccgg auccagcacc    3240
cagacuugau ccugcuacag uacguggaug acuuacugcu ggccgccacu ucugagcuag    3300
acugccaaca agguacucgg gcccguuac aaacccuagg gaaccucggg uaucgggccu     3360
cggccaagaa agcccaaauu ugccagaaac aggucaagua ucuggggua cuucuaaaag    3420
```

```
agggucagag auggcugacu gaggccagaa aagagacugu gaugggggcag ccuacuccga    3480 agaccccucg acaacuaagg gaguuccuag ggacggcagg cuucugucgc cucuggaucc    3540
cugguuuugc agaaauggca gcccccuugu acccucucac caaaacgggg acucuguuua    3600 auugggccc agaccaacaa aaggccuauc aagaaaucaa gcaagcucuu cuaacugccc     3660
cagcccuggg guugccagau uugacuaagc ccuuugaacu cuuugucgac gagaagcagg    3720
gcuacgccaa aggguguccua acgcaaaaac ugggaccuug gcgucggccg guggccuacc   3780
uguccaaaaa gcuagaccca guagcagcug gguggccccc uugccuacgg augguagcag    3840
ccauugccgu acugacaaag gaugcaggca agcuaaccau gggacagcca cuagucauuc    3900
uggcccccca ugcaguagag gcacuaguca acaaccccc cgaccgcugg cuuccaacg      3960 cccggaugac ucacuaucag gccuugcuuu uggacacgga ccggguccag uucggaccgg    4020
ugguagcccu gaacccggcu acgcugcucc cacugccuga ggaagggcug caacacaacu    4080
gccuugauau ccuggccgaa gcccacggaa cccgacccga ccuaacggac cagccgcucc    4140
cagacgccga ccacaccugg uacacggaug gaagcagucu cuuacaagag ggacagcgua    4200
aggcgggagc ugcggugacc accgagaccg agguaaucug ggcuaaagcc cugccagccg    4260
ggacauccgc ucagcgggcu gaacugauag cacucaccca ggcccuaaag auggcagaag    4320
guaagaagcu aaauguuuau acugauagcc guuaugcuuu ugcuacugcc cauauccaug    4380
gagaaauaua cagaaggcgu ggguugcuca caucagaagg caaagagauc aaaaauaaag    4440
acgagaucuu ggcccuacua aaagcccucu uucugcccaa aagacuuagc auaauccauu    4500
guccaggaca ucaaaaggga cacagcgccg aggcuagagg caaccggaug gcugaccaag    4560
cggcccgaaa ggcagccauc acagagacuc cagacaccuc uacccuccuc auagaaaauu    4620
caucacccua caccucagaa cauuuucauu acacagugac ugauauaaag gaccuaacca    4680 aguuggggc cauuuaugau aaaacaaaga aguauugggu cuaccaagga aaaccuguga    4740
ugccugacca guuuacuuuu gaauuauuag acuuucuuca ucagcugacu caccucagcu    4800
ucucaaaaau gaaggcucuc cuagagagaa gccacagucc cuacuacaug cugaaccggg    4860
aucgaacacu caaaaauauc acugagaccu gcaaagcuug ugcacaaguc aacgccagca    4920
agucugccgu uaaacaggga acuagggucc gcgggcaucg gcccggcacu cauggggaga    4980
ucgauuucac cgagauaaag cccggauugu auggcuauaa auaucuucua guuuuuauag    5040
auaccuuuuc uggcugggua gaagccuucc caaccaagaa agaaaccgcc aaggucguaa    5100
ccaagaagcu acuagaggag aucuuccccca gguucggcau gccucagguu uugggaacug   5160
acaaugggcc ugccuucguc uccaagguga gucagacagu ggccgaucug uuggggauug    5220
auugggaauu acauugugca uacagacccc aaagcucagg ccaguagaa agaaugaaua    5280 gaaccaucaa ggagacuuua acuaaauuaa cgcuugcaac uggcucuaga gacugggugc    5340
uccuacuccc cuuagcccug uaccgagccc gcaacacgcc ggggccccau ggccucaccc    5400
cauaugagau cuuuauggg gcaccccgc cccuuguaaa cuucccugac ccugacauga    5460
caagaguuac uaacagcccc ucucuccaag cucacuuaca ggcucucuac uuaguccagc    5520
acgaagucug gagaccucug gcggcagccu accaagaaca acuggaccga ccggugguac    5580
cucacccuua ccgagucggc gacacagugu ggguccgccg acaccagacu aagaaccuag    5640
aaccucgcug gaaaggaccu uacacaguc ugcugaccac ccccaccgcc cucaaaguag     5700
acggcaucgc agcuuggaua cacgccgccc acgugaaggc ugccgacccc ggggguggac    5760
```

-continued

```
cauccucuag acugacaugg cgcguucaac gcucucaaaa ccccuuaaaa auaagguuaa    5820
cccgcgaggc ccccuaauuc ccuuaauucu ucugaugcuc agaggggca guacugcuuc    5880
gcccggcucc aguccucauc aagucuauaa uaucaccugg gagguaacca auggagaucg    5940
ggagacggua ugggcaacuu cuggcaacca cccucugugg accggguggc cugaccuuac    6000
cccagauuua uguauguuag cccaccaugg accaucuuau uggggcuag aauaucaauc     6060
cccuuuucu ucucccccgg ggccccuug uugcucaggg ggcagcagcc caggcuguuc     6120
cagagacugc gaagaaccuu uaaccucccu caccccucgg ugcaacacug ccuggaacag    6180
acucaagcua gaccagacaa cucauaaauc aaaugaggga uuuuauguuu gccccgggcc    6240
ccaccgcccc cgagaaucca agucauguqg gguccagac uccuucuacu ugccuauug     6300
gggcugugag acaaccggua gagcuuacug gaagcccucc ucaucauggg auuucaucac    6360
aguaaacaac aaucucaccu cugaccaggc uguccaggua ugcaaagaua auaaguggug    6420
caaccccuua guuauucggu uuacagacgc cgggagacgg guuacuuccu ggaccacagg    6480
acauuacugg ggcuuacguu uguaugucuc ggacaagau ccagggcuua cauuuggau     6540
ccgacucaga uaccaaaauc uaggaccccg cgucccaaua gggccaaacc ccguucuggc    6600
agaccaacag ccacucucca agcccaaacc uguuaagucg ccuucaguca ccaaaccacc    6660
caguggqacu ccucucuccc cuacccaacu uccaccggcg ggaacggaaa auaggcugcu    6720
aaacuuagua gacggagccu accaagcccu caaccucacc aguccugaca aaacccaaga    6780
gugcuggugu ugucuaguag cgggaccccc cuacuacgaa ggguugccg uccuggguac     6840
cuacuccaac cauaccucug ucccagccaa cugcuccgug gccucccaac acaaguugac    6900
ccuguccgaa gugaccggac aggacucug cauaggagca guucccaaaa cacaucaggc    6960
ccuauguaau accacccaga caagcagucg aggguccuau uaucuaguug ccccuacagg    7020
uaccaugugg gcuuguagua ccgggcuuac uccaugcauc uccaccacca uacugaaccu    7080
uaccacugau uauuguguuc uugucgaacu cuggccaaga gucaccuauc auuccccag     7140
cuauguuuac ggccguuuug agagauccaa ccgacacaaa agagaaccgg ugucguuaac    7200
ccuggcccua uuauggggug gacuaaccau gggggqaauu gccgcuggaa uaggaacagg    7260
gacuacugcu cuaauggcca cucagcaauu ccagcagcuc caagccgcag uacaggauga    7320
ucucagggag guugaaaaau caaucucuaa ccuagaaaag ucucucacuu cccugucuga    7380
aguuguccua cagaaucgaa ggggccuaga cuuguuauuu cuaaaagaag gagggcugug    7440
ugcugcucua aaagaagaau guugcuucua ugcggaccac acaggacuag ugagagacag    7500
cauggccaaa uugagagaga ggcuuaauca gagacagaaa cuguuugagu caacucaagg    7560
augguuugag ggacuguuua acagauccc uuggguuacc accugauau cuaccauuau     7620
gggacccuc auguacucc uaaugauuuu gcucuucgga cccugcauuc uuaaucgauu      7680
agccaauuu guuaaagaca ggauaucagu ggccaggcu cuaguuuuga cucaacaaua     7740
ucaccagcug aagccuauag aguacgagcc auagauaaaa uaaagauuu uauuuagucu    7800
ccagaaaaag gggggaauga aagaccccac cuguaggguu ggcaagcuag cuuaaguaac    7860
gccauuugc aaggcaugga aaauacauaa acugagaaua gagaaguuca gaucaagguc    7920
aggaacagau ggaacagcug aauaugggcc aaacaggaua ucuggguaa gcaguccug     7980
ccccggcuca gggccaagaa cagauggaac agcugaauau gggccaaaca ggauaucuguu    8040
gguaagcagu uccugcccg gcucagggcc aagaacagau ggucccaga ugcgguccag    8100
cccucagcag uuucuagaga accaucagau guuuccaggg ugccccaagg accugaaaug    8160
```

-continued

```
acccugugcc uuauuugaac uaaccaauca guucgcuucu cgcuucuguu cgcgcgcuuc        8220
ugcuccccga gcucaauaaa agagcccaca accccucacu cggggcgcca guccuccgau        8280
ugacugaguc gcccggguac ccguguaucc aauaaacccu cuugcaguug ca                8332
```

<210> SEQ ID NO 26
<211> LENGTH: 1312
<212> TYPE: PRT
<213> ORGANISM: Murine leukemia virus

<400> SEQUENCE: 26

```
Leu Thr Ser Ser Val Ser Gly Gly Pro Val Val Glu Leu Thr Ser Ser
 1               5                  10                  15

Glu His Pro Ala Ala Thr Leu Gly Asp Val Pro Gly Thr Ser Gly Ala
             20                  25                  30

Val Phe Val Ala Arg Pro Glu Ser Lys Asn Pro Asp Ala Phe Gly Leu
         35                  40                  45

Phe Gly Ala Pro Pro Leu Glu Glu Gly Tyr Val Val Leu Val Gly Asp
     50                  55                  60

Glu Asn Leu Lys Gln Phe Pro Pro Ser Glu Phe Leu Leu Ser Val
 65                  70                  75                  80

Trp Asp Arg Ser Arg Ala Ala Arg Leu Val Cys Cys Ser Ile Val Leu
                 85                  90                  95

Cys Cys Leu Cys Leu Thr Val Phe Leu Tyr Leu Ser Glu Asn Met Gly
            100                 105                 110

Gln Thr Val Thr Thr Pro Leu Ser Leu Thr Leu Gly His Trp Lys Asp
        115                 120                 125

Val Glu Arg Ile Ala His Asn Gln Ser Val Asp Val Lys Lys Arg Arg
    130                 135                 140

Trp Val Thr Phe Cys Ser Ala Glu Trp Pro Thr Phe Asn Val Gly Trp
145                 150                 155                 160

Pro Arg Asp Gly Thr Phe Asn Arg Asp Leu Ile Thr Gln Val Lys Ile
                165                 170                 175

Lys Val Phe Ser Pro Gly Pro His Gly His Pro Asp Gln Val Pro Tyr
            180                 185                 190

Ile Val Thr Trp Glu Ala Leu Ala Phe Asp Pro Pro Trp Val Lys
        195                 200                 205

Pro Phe Val His Pro Lys Pro Pro Pro Leu Pro Pro Ser Ala Pro
    210                 215                 220

Ser Leu Pro Leu Glu Pro Pro Arg Ser Thr Pro Pro Arg Ser Ser Leu
225                 230                 235                 240

Tyr Pro Ala Leu Thr Pro Ser Leu Gly Ala Lys Pro Lys Pro Gln Val
                245                 250                 255

Leu Ser Asp Ser Gly Gly Pro Leu Ile Asp Leu Leu Thr Glu Asp Pro
            260                 265                 270

Pro Pro Tyr Arg Asp Pro Arg Pro Pro Pro Ser Asp Arg Asp Gly Asn
        275                 280                 285

Gly Gly Glu Ala Thr Pro Ala Gly Glu Ala Pro Asp Pro Ser Pro Met
    290                 295                 300

Ala Ser Arg Leu Arg Gly Arg Arg Glu Pro Pro Val Ala Asp Ser Thr
305                 310                 315                 320

Thr Ser Gln Ala Phe Pro Leu Arg Ala Gly Gly Asn Gly Gln Leu Gln
                325                 330                 335

Tyr Trp Pro Phe Ser Ser Ser Asp Leu Tyr Asn Trp Lys Asn Asn Asn
```

-continued

```
            340                 345                 350
Pro Ser Phe Ser Glu Asp Pro Gly Lys Leu Thr Ala Leu Ile Glu Ser
            355                 360                 365
Val Leu Ile Thr His Gln Pro Thr Trp Asp Asp Cys Gln Gln Leu Leu
370                 375                 380
Gly Thr Leu Leu Thr Gly Glu Glu Lys Gln Arg Val Leu Leu Glu Ala
385                 390                 395                 400
Arg Lys Ala Val Arg Gly Asp Asp Gly Arg Pro Thr Gln Leu Pro Asn
                405                 410                 415
Glu Val Asp Ala Ala Phe Pro Leu Glu Arg Pro Asp Trp Asp Tyr Thr
            420                 425                 430
Thr Gln Ala Gly Arg Asn His Leu Val His Tyr Arg Gln Leu Leu Leu
            435                 440                 445
Ala Gly Leu Gln Asn Ala Gly Arg Ser Pro Thr Asn Leu Ala Lys Val
450                 455                 460
Lys Gly Ile Thr Gln Gly Pro Asn Glu Ser Pro Ser Ala Phe Leu Glu
465                 470                 475                 480
Arg Leu Lys Glu Ala Tyr Arg Arg Tyr Thr Pro Tyr Asp Pro Glu Asp
                485                 490                 495
Pro Gly Gln Glu Thr Asn Val Ser Met Ser Phe Ile Trp Gln Ser Ala
            500                 505                 510
Pro Asp Ile Gly Arg Lys Leu Glu Arg Leu Glu Asp Leu Lys Asn Lys
            515                 520                 525
Thr Leu Gly Asp Leu Val Arg Glu Ala Glu Lys Ile Phe Asn Lys Arg
            530                 535                 540
Glu Thr Pro Glu Glu Arg Glu Glu Arg Ile Arg Arg Glu Thr Glu Glu
545                 550                 555                 560
Lys Glu Glu Arg Arg Arg Thr Glu Asp Glu Gln Lys Glu Lys Glu Arg
                565                 570                 575
Asp Arg Arg Arg His Arg Glu Met Ser Lys Leu Leu Ala Thr Val Val
            580                 585                 590
Ser Gly Gln Lys Gln Asp Arg Gln Gly Gly Glu Arg Arg Ser Leu
            595                 600                 605
Asp Arg Asp Gln Cys Ala Tyr Cys Lys Glu Lys Gly His Trp Ala Lys
            610                 615                 620
Asp Cys Pro Lys Pro Arg Gly Pro Arg Gly Pro Arg Pro Gln Thr
625                 630                 635                 640
Ser Leu Leu Thr Leu Asp Asp Met Ala Arg Ser Thr Leu Ser Lys Pro
                645                 650                 655
Leu Lys Asn Lys Val Asn Pro Arg Gly Pro Leu Ile Pro Leu Ile Leu
                660                 665                 670
Leu Met Leu Arg Gly Val Ser Thr Ala Ser Pro Gly Ser Ser Pro His
            675                 680                 685
Gln Val Tyr Asn Ile Thr Trp Glu Val Thr Asn Gly Asp Arg Glu Thr
            690                 695                 700
Val Trp Ala Thr Ser Gly Asn His Pro Leu Trp Thr Trp Trp Pro Asp
705                 710                 715                 720
Leu Thr Pro Asp Leu Cys Met Leu Ala His His Gly Pro Ser Tyr Trp
                725                 730                 735
Gly Leu Glu Tyr Gln Ser Pro Phe Ser Ser Pro Gly Pro Pro Cys
            740                 745                 750
Cys Ser Gly Gly Ser Ser Pro Gly Cys Ser Arg Asp Cys Glu Glu Pro
            755                 760                 765
```

```
Leu Thr Ser Leu Thr Pro Arg Cys Asn Thr Ala Trp Asn Arg Leu Lys
    770                 775                 780

Leu Asp Gln Thr Thr His Lys Ser Asn Glu Gly Phe Tyr Val Cys Pro
785                 790                 795                 800

Gly Pro His Arg Pro Arg Glu Ser Lys Ser Cys Gly Gly Pro Asp Ser
            805                 810                 815

Phe Tyr Cys Ala Tyr Trp Gly Cys Glu Thr Thr Gly Arg Ala Tyr Trp
                820                 825                 830

Lys Pro Ser Ser Ser Trp Asp Phe Ile Thr Val Asn Asn Asn Leu Thr
            835                 840                 845

Ser Asp Gln Ala Val Gln Val Cys Lys Asp Asn Lys Trp Cys Asn Pro
850                 855                 860

Leu Val Ile Arg Phe Thr Asp Ala Gly Arg Arg Val Thr Ser Trp Thr
865                 870                 875                 880

Thr Gly His Tyr Trp Gly Leu Arg Leu Tyr Val Ser Gly Gln Asp Pro
                885                 890                 895

Gly Leu Thr Phe Gly Ile Arg Leu Arg Tyr Gln Asn Leu Gly Pro Arg
                900                 905                 910

Val Pro Ile Gly Pro Asn Pro Val Leu Ala Asp Gln Gln Pro Leu Ser
            915                 920                 925

Lys Pro Lys Pro Val Lys Ser Pro Ser Val Thr Lys Pro Pro Ser Gly
    930                 935                 940

Thr Pro Leu Ser Pro Thr Gln Leu Pro Pro Ala Gly Thr Glu Asn Arg
945                 950                 955                 960

Leu Leu Asn Leu Val Asp Gly Ala Tyr Gln Ala Leu Asn Leu Thr Ser
            965                 970                 975

Pro Asp Lys Thr Gln Glu Cys Trp Leu Cys Leu Val Ala Gly Pro Pro
            980                 985                 990

Tyr Tyr Glu Gly Val Ala Val Leu Gly Thr Tyr Ser Asn His Thr Ser
            995                 1000                1005

Ala Pro Ala Asn Cys Ser Val Ala Ser Gln His Lys Leu Thr Leu Ser
    1010                1015                1020

Glu Val Thr Gly Gln Gly Leu Cys Ile Gly Ala Val Pro Lys Thr His
1025                1030                1035                1040

Gln Ala Leu Cys Asn Thr Thr Gln Thr Ser Ser Arg Gly Ser Tyr Tyr
            1045                1050                1055

Leu Val Ala Pro Thr Gly Thr Met Trp Ala Cys Ser Thr Gly Leu Thr
                1060                1065                1070

Pro Cys Ile Ser Thr Thr Ile Leu Asn Leu Thr Thr Asp Tyr Cys Val
    1075                1080                1085

Leu Val Glu Leu Trp Pro Arg Val Thr Tyr His Ser Pro Ser Tyr Val
    1090                1095                1100

Tyr Gly Leu Phe Glu Arg Ser Asn Arg His Lys Arg Glu Pro Val Ser
1105                1110                1115                1120

Leu Thr Leu Ala Leu Leu Leu Gly Gly Leu Thr Met Gly Gly Ile Ala
            1125                1130                1135

Ala Gly Ile Gly Thr Gly Thr Thr Ala Leu Met Ala Thr Gln Gln Phe
            1140                1145                1150

Gln Gln Leu Gln Ala Ala Val Gln Asp Asp Leu Arg Glu Val Glu Lys
    1155                1160                1165

Ser Ile Ser Asn Leu Glu Lys Ser Leu Thr Ser Leu Ser Glu Val Val
    1170                1175                1180
```

```
Leu Gln Asn Arg Arg Gly Leu Asp Leu Leu Phe Leu Lys Glu Gly Gly
1185                1190                1195                1200

Leu Cys Ala Ala Leu Lys Glu Glu Cys Cys Phe Tyr Ala Asp His Thr
            1205                1210                1215

Gly Leu Val Arg Asp Ser Met Ala Lys Leu Arg Glu Arg Leu Asn Gln
            1220                1225                1230

Arg Gln Lys Leu Phe Glu Ser Thr Gln Gly Trp Phe Glu Gly Leu Phe
        1235                1240                1245

Asn Arg Ser Pro Trp Phe Thr Thr Leu Ile Ser Thr Ile Met Gly Pro
    1250                1255                1260

Leu Ile Val Leu Leu Met Ile Leu Leu Phe Gly Pro Cys Ile Leu Asn
1265                1270                1275                1280

Arg Leu Val Gln Phe Val Lys Asp Arg Ile Ser Val Val Gln Ala Leu
            1285                1290                1295

Val Leu Thr Gln Gln Tyr His Gln Leu Lys Pro Ile Glu Tyr Glu Pro
            1300                1305                1310
```